US008524702B2

(12) United States Patent (10) Patent No.: US 8,524,702 B2
Howbert et al. (45) Date of Patent: Sep. 3, 2013

(54) SUBSTITUTED BENZOAZEPINES AS TOLL-LIKE RECEPTOR MODULATORS

(75) Inventors: James Jeffry Howbert, Redmond, WA (US); Gregory Dietsch, Snohomish, WA (US); Robert Hershberg, Seattle, WA (US); Laurence E. Burgess, Boulder, CO (US); George A. Doherty, Boulder, CO (US); C. Todd Eary, Boulder, CO (US); Robert D. Groneberg, Boulder, CO (US); Zachary Jones, Boulder, CO (US)

(73) Assignees: VentiRx Pharmaceuticals, Inc., Seattle, WA (US); Array BioPharma, Inc., Boulder, CO (US)

( * ) Notice: Subject to any disclaimer, the term of this patent is extended or adjusted under 35 U.S.C. 154(b) by 220 days.

(21) Appl. No.: 12/859,182

(22) Filed: Aug. 18, 2010

(65) Prior Publication Data
US 2011/0118235 A1 May 19, 2011

Related U.S. Application Data

(60) Provisional application No. 61/234,971, filed on Aug. 18, 2009.

(51) Int. Cl.
*A61P 35/00* (2006.01)
*A61K 31/55* (2006.01)
*C07D 223/16* (2006.01)

(52) U.S. Cl.
USPC ..................................... 514/213.01; 540/593

(58) Field of Classification Search
USPC ..................................... 514/213.01; 540/593
See application file for complete search history.

(56) References Cited

U.S. PATENT DOCUMENTS

| 4,002,610 | A | 1/1977 | Mohrbacher et al. |
| 6,043,238 | A | 3/2000 | Cooper et al. |
| 2002/0128208 | A1 | 9/2002 | Snyder et al. |
| 2007/0197478 | A1 | 8/2007 | Jones et al. |
| 2008/0008682 | A1 | 1/2008 | Chong et al. |
| 2008/0057074 | A1 | 3/2008 | Takaoka et al. |
| 2008/0234251 | A1 | 9/2008 | Doherty et al. |
| 2008/0306050 | A1 | 12/2008 | Doherty et al. |
| 2010/0216988 | A1 | 8/2010 | Alonso et al. |
| 2011/0092485 | A1 | 4/2011 | Howbert et al. |

FOREIGN PATENT DOCUMENTS

| EP | 0825186 A1 | 2/1998 |
| EP | 0825186 B1 | 4/2002 |
| EP | 1790637 A1 | 5/2007 |
| EP | 1849781 A1 | 10/2007 |
| WO | WO-9612493 A1 | 5/1996 |
| WO | WO-9855148 A1 | 12/1998 |
| WO | WO-03007955 A2 | 1/2003 |
| WO | WO-2004096134 A2 | 11/2004 |
| WO | WO-2005009973 A1 | 2/2005 |
| WO | WO-2005035534 A1 | 4/2005 |
| WO | WO-2007024612 A2 | 3/2007 |
| WO | WO-2007040840 A2 | 4/2007 |
| WO | WO-2007096151 A2 | 8/2007 |
| WO | WO-2007128460 A1 | 11/2007 |
| WO | WO-2008024892 A2 | 2/2008 |
| WO | WO-2008109177 A2 | 9/2008 |
| WO | WO-2008109180 A2 | 9/2008 |
| WO | WO-2008109181 A2 | 9/2008 |
| WO | WO-2009000412 A1 | 12/2008 |

OTHER PUBLICATIONS

Agrawal, et al., "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos" *J. Immunol.*, 171:4984-4989 (2003).
Czarniecki, M. "Small Molecule Modulators of Toll-like Receptors". *J Medicinal Chem.* vol. 51, No. 21, Nov. 13, 2008, pp. 6621-6626.
Kiechl, et al., "Toll-Like Receptor 4 Polymorphisms and Atherogenesis" *N. Engl. J. Med.*, 347(3):185-192 (2002).
Breslin, H.J. et al., "Synthesis and Anti-HIV Activity of 1,3,4,5-Tetrahydro-2H-1,4-benzodiazepin-2-one (TBO) Derivatives. Truncated 4,5,6,7-Tetrahydro-5-methylimidazo [4,5,1-jk] [1,4] benzodiazepin-2(1H)-ones (TIBO) Analogues," *Bioorganic & Medicinal Chemistry*, 7, (1999), pp. 2427-2436.
Hemmi, H. et al., "Small anti-viral compounds activate immune cells via the TLR7 MyD88-dependant signaling pathway," *Nature Immunology*, vol. 3, No. 2, Feb. 2002, pp. 196-200.
Jurk, M. et al., "Human TLR7 or TLR8 independently confer responsiveness to the antiviral compound R-848," *Nature Immunology*, vol. 3, No. 6, Jun. 2002, p. 499.
Papageorgiou, C. and Borer, X., "A Non-Peptide Ligand for the Somatostatin Receptor Having a Benzodiazepinone Structure," *Bioorganic & Medicinal Chemistry Letters*, Vo. 6, No. 3, 1996, pp. 267-272.

*Primary Examiner* — Brenda Coleman
(74) *Attorney, Agent, or Firm* — Mintz Levin Cohn Ferris Glovsky and Popeo, P.C.; Heidi A. Erlacher; Lian Ouyang

(57) ABSTRACT

Provided are compositions and methods useful for modulation of signaling through the Toll-like receptors TLR7 and/or TLR8. The compositions and methods have use in treating or preventing disease, including cancer, autoimmune disease, infectious disease, inflammatory disorder, graft rejection, and graft-verses-host disease.

20 Claims, No Drawings

SUBSTITUTED BENZOAZEPINES AS TOLL-LIKE RECEPTOR MODULATORS

RELATED APPLICATIONS

This application claims priority to U.S. Provisional Patent Application No. 61/234,971 filed on Aug. 18, 2009. The contents of the aforementioned application are hereby incorporated by reference in their entirety.

BACKGROUND OF THE INVENTION

1. Field of the Invention

This invention relates to methods and compositions for modulating immune function. More specifically, this invention relates to compositions and methods for modulating TLR7- and/or TLR8-mediated signaling.

2. Description of the State of the Art

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen associated molecular patterns (PAMPs). Compositions and methods useful for modulating innate immunity are therefore of great interest, as they may affect therapeutic approaches to conditions involving autoimmunity, inflammation, allergy, asthma, graft rejection, graft versus host disease (GvHD), infection, cancer, and immunodeficiency.

Toll-like receptors (TLRs) are type I transmembrane proteins that allow organisms (including mammals) to detect microbes and initiate an innate immune response (Beutler, B., *Nature* 2004, 430:257-263). They contain homologous cytoplasmic domains and leucine-rich extracellular domains and typically form homodimers that sense extracellular (or internalized) signals and subsequently initiate a signal transduction cascade via adaptor molecules such as MyD88 (myeloid differentiation factor 88). There is such high homology in the cytoplasmic domains of the TLRs that, initially, it was suggested that similar signaling pathways exist for all TLRs (Re, F., Strominger, J. L., *Immunobiology* 2004, 209:191-198). Indeed, all TLRs can activate NF-kB and MAP kinases; however, the cytokine/chemokine release profiles derived from TLR activation appears unique to each TLR. Additionally, the signaling pathway that TLRs stimulate is very similar to the pathway that the cytokine receptor IL-1R induces. This may be due to the homology that these receptors share, i.e., TIR (Toll/IL-1R homology) domains. Once the TIR domain is activated in TLRs and MyD88 is recruited, activation of the IRAK family of serine/threonine kinases results which eventually promotes the degradation of Ik-B and activation of NF-kB (Means T. K., et al. *Life Sci.* 2000, 68:241-258). While it appears that this cascade is designed to allow extracellular stimuli to promote intracellular events, there is evidence that some TLRs migrate to endosomes where signaling can also be initiated. This process may allow for intimate contact with engulfed microbes and fits with the role that these receptors play in the innate immune response (Underhill, D. M., et al., *Nature* 1999, 401:811-815). This process might also allow host nucleic acids, released by damaged tissues (for example, in inflammatory disease) or apoptosis to trigger a response via endosomal presentation. Among mammals, there are 11 TLRs that coordinate this rapid response. A hypothesis put forward years ago (Janeway, C. A., Jr., *Cold Spring Harb. Symp. Quant. Biol.* 1989, 54:1-13) that the innate immune response initiates the adaptive immune response through the pattern of TLR activation caused by microbes has now been substantiated. Thus, the pathogen-associated molecular patterns (PAMPs) presented by a diverse group of infectious organisms results in a innate immune response involving certain cytokines, chemokines and growth factors followed by a precise adaptive immune response tailored to the infectious pathogen via antigen presentation resulting in antibody production and cytotoxic T cell generation.

Gram-negative bacterial lipopolysaccharide (LPS) has long been appreciated as an adjuvant and immune-stimulant and as a pharmacological tool for inducing an inflammatory reaction in mammals similar to septic shock. Using a genetic approach, TLR4 was identified as the receptor for LPS. The discovery that LPS is an agonist of TLR4 illustrates the usefulness of TLR modulation for vaccine and human disease therapy (Aderem, A.; Ulevitch, R. J., *Nature* 2000, 406:782-787). It is now appreciated that various TLR agonists can activate B cells, neutrophils, mast cells, eosinophils, endothelial cells and several types of epithelia in addition to regulating proliferation and apoptosis of certain cell types.

To date, TLR7 and TLR8, which are somewhat similar, have been characterized as receptors for single-stranded RNA found in endosomal compartments and thus thought to be important for the immune response to viral challenge. Imiquimod, an approved topical anti-viral/anti-cancer drug, has recently been described as a TLR7 agonist that has demonstrated clinical efficacy in certain skin disorders (Miller R. L., et al., *Int. J. Immunopharm.* 1999, 21:1-14). This small molecule drug has been described as a structural mimetic of ssRNA. TLR8 was first described in 2000 (Du, X., et al., *European Cytokine Network* 2000 (September), 11(3):362-371) and was rapidly ascribed to being involved with the innate immune response to viral infection (Miettinen, M., et al., *Genes and Immunity* 2001 (October), 2(6):349-355).

Recently it was reported that certain imidazoquinoline compounds having antiviral activity are ligands of TLR7 and TLR8 (Hemmi H., et al. (2002) *Nat. Immunol.* 3:196-200; Jurk M., et al. (2002) *Nat. Immunol.* 3:499). Imidazoquinolines are potent synthetic activators of immune cells with antiviral and antitumor properties. Using macrophages from wildtype and MyD88-deficient mice, Hemmi et al. recently reported that two imidazoquinolines, imiquimod and resiquimod (R848), induce tumor necrosis factor (TNF) and interleukin-12 (IL-12) and activate NF-icB only in wildtype cells, consistent with activation through a TLR (Hemmi H., et al. (2002) *Nat. Immunol.* 3:196-200). Macrophages from mice deficient in TLR7 but not other TLRs produced no detectable cytokines in response to these imidazoquinolines. In addition, the imidazoquinolines induced dose-dependent proliferation of splenic B cells and the activation of intracellular signaling cascades in cells from wildtype but not TLR7-/- mice. Luciferase analysis established that expression of human TLR7, but not TLR2 or TLR4, in human embryonic kidney cells results in NF-KB activation in response to resiquimod. The findings of Hemmi et al. thus suggest that these imidazoquinoline compounds are non-natural ligands of TLR7 that can induce signaling through TLR7. Recently it was reported that R848 is also a ligand for human TLR8 (Jurk M., et al. (2002) Nat. Immunol. 3:499).

In view of the great therapeutic potential for compounds that modulate toll-like receptors, and despite the work that

SUMMARY OF THE INVENTION

The compositions described herein are useful for modulating immune responses in vitro and in vivo. Such compositions will find use in a number of clinical applications, such as in methods for treating or preventing conditions involving unwanted immune activity, including inflammatory and autoimmune disorders.

Specifically, the invention relates to a compound having the formula I:

(I)

or a tautomer, enantiomer or salt thereof, wherein:
Y is substituted aryl, heteroaryl, or substituted heteroaryl, wherein said substituted aryl or substituted heteroaryl is substituted with one or more groups independently selected from CN, OH, —C(=O)$R^9$, halogen, and —CH=CHC(=O)$R^9$;
  $R^9$ is selected from alkyl, $OR^{15}$, and $NR^{10}R^{11}$;
  $R^{15}$ is selected from H, alkyl, and —CH$_2$O(alkyl),
  $R^{10}$ and $R^{11}$ are each independently alkyl, wherein said alkyl is optionally substituted with —OH or $R^{10}$ and $R^{11}$ together with the nitrogen atom to which they are attached form a heterocyclic ring, wherein said heterocyclic ring is optionally substituted with one or more —OH;
  $R^2$ is selected from $OR^{14}$ and $NR^6R^7$;
  $R^6$ and $R^7$ are each independently selected from H, alkyl, cycloalkyl, heterocycloalkyl or benzyl, wherein said alkyl, cycloalkyl, or benzyl is optionally substituted with one or more groups independently selected from —F, —$OR^8$, —$NR^{12}SO_2R^{13}$, —C(=O)$NR^{12}R^{13}$ or $R^6$ and $R^7$ together with the nitrogen atom to which they are attached form a heterocyclic ring, further wherein said heterocyclic ring is optionally substituted with one or more —OH;
  $R^8$ is selected from hydrogen and alkyl, and
  $R^{12}$, $R^{13}$ and $R^{14}$ are each independently selected from H and alkyl, wherein said alkyl is optionally substituted with —OH;
provided that
a) when Y is aryl substituted with or, then $R^2$ is not —OCH$_2$CH$_3$ (-OEt), or
b) when Y is aryl substituted with —C(=O)$R^9$, and $R^9$=$NR^{10}R^{11}$, and $R^{10}$ and $R^{11}$ together with the nitrogen atom to which they are attached form an unsubstituted pyrrolidine ring, then $R^2$ is not -OEt or —N(propyl)$_2$.

The invention also relates to a compound having the formula II:

(II)

or a tautomer, enantiomer or salt thereof, wherein W is H or —OH; Z is H or —OH; n is 1 or 2, and $R^2$ is as defined in formula I; provided that when W and Z are both H and n is 1, then $R^2$ is not -OEt or —N(propyl)$_2$.

The invention also relates to a compound having the formula III:

(III)

or a tautomer, enantiomer or salt thereof, wherein
  T is CH, CZ, or N;
  U is CH, CZ, or N;
  V is CH, CZ, or N;
  X is CH, CZ, or N;
  W is CH, CZ, or N;
  Z is selected from halogen, —CN, —CONR$^{16}$R$^{17}$, —COOR$^{18}$, —CH=CHCOOR$^{18}$, and —OR$^{19}$;
  $R^{16}$, $R^{17}$, $R^{18}$, and $R^{19}$ are each independently selected from H, alkyl, and —CH$_2$O(alkyl); and $R^2$ is as defined in formula I.

The invention also relates to a compound having the formula IV:

(IV)

or a tautomer, enantiomer or salt thereof, wherein $R^2$ is as defined in formula I.

The invention also relates to a compound having the formula V:

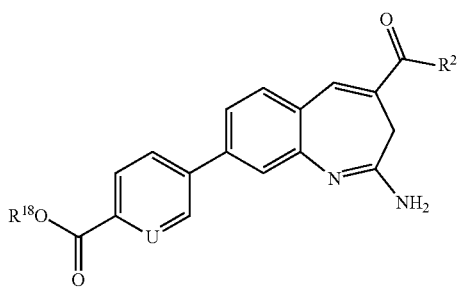

(V)

or a tautomer, enantiomer or salt thereof, wherein U is N or CZ, and Z is halogen; and $R^2$ is as defined in formula I.

The invention also relates to a compound having the formula VI:

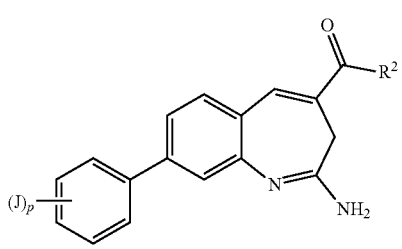

(VI)

or a tautomer, enantiomer or salt thereof, wherein

J is independently selected from halogen, —C(=O)$R^9$ and —CH=CHC(=O)$R^9$;

p is selected from 1, 2, and 3; and $R^2$ is as defined in formula I; provided that when p is 1 and J is

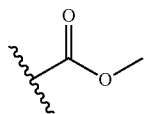

attached at the 4-position of the aryl ring, then $R^2$ is not -OEt, and further provided that when p is 1 and J is

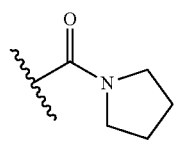 [SMILES: *C(=O)N1CCCC1]

attached at the 4-position of the aryl ring, then $R^2$ is not -OEt or —N(propyl)$_2$.

The invention also relates to a compound having the formula VII:

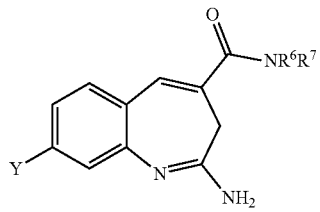

(VII)

or a tautomer, enantiomer or salt thereof, wherein:

Y is substituted aryl or substituted heteroaryl, wherein said aryl or heteroaryl is substituted with one or more groups independently selected from —C(=O)$R^9$, halogen, and —CH=CHC(=O)$R^9$;

$R^9$ is selected from alkyl, $OR^{15}$, and $NR^{10}R^{11}$;

$R^{15}$ is selected from H, alkyl, and —CH$_2$O(alkyl);

$R^{10}$ and $R^{11}$ are each independently alkyl, wherein said alkyl is optionally substituted with —OH or $R^{10}$ and $R^{11}$ together with the nitrogen atom to which they are attached form a heterocyclic ring, wherein said heterocyclic ring is optionally substituted with one or more —OH; and $R^6$ and $R^7$ are each independently selected from H, alkyl or alkenyl, wherein said alkyl or alkenyl is optionally substituted with one or more groups independently selected from —F or —OH; provided that when Y is aryl substituted with —C(=O)$R^9$, and $R^9$=$NR^{10}R^{11}$, and $R^{10}$ and $R^{11}$ together with the nitrogen atom to which they are attached form an unsubstituted pyrrolidine ring, then $R^6$ and $R^7$ are not both propyl.

The compounds of the invention may be used in combination with other known therapeutic agents. Accordingly, this invention also relates to pharmaceutical compositions comprising a therapeutically effective amount of a compound of the invention or a salt thereof, in combination with a second therapeutic agent.

This invention further provides methods of modulating TLR7- and/or TLR8-mediated signaling, comprising contacting a cell expressing TLR7 and/or TLR8 with an effective amount of a compound of the invention, or a salt thereof. In one aspect, the method inhibits TLR7- and/or TLR8-mediated immunostimulatory signaling.

This invention further provides methods of modulating TLR7- and/or TLR8-mediated immunostimulation in a subject, comprising administering to a patient having or at risk of developing TLR7- and/or TLR8-mediated immunostimulation a compound of the invention, or a salt thereof, in an amount effective to inhibit TLR7- and/or TLR8-mediated immunostimulation in the subject.

This invention further provides methods of modulating TLR7- and/or TLR8-mediated immunostimulation in a subject, comprising administering to a patient having or at risk of developing TLR7- and/or TLR8-mediated immunostimulation a compound of the invention, or a salt thereof, in an amount effective to promote TLR7- and/or TLR8-mediated immunostimulation in the subject.

This invention further provides methods of treating or preventing a disease or condition by modulation of TLR7- and/or TLR8-mediated cellular activities, comprising administering to a warm-blooded animal, such as a mammal, for example a human, having or at risk of developing said disease or condition, a compound of the invention, or a salt thereof.

This invention further provides methods of modulating the immune system of a mammal, comprising administering to a mammal a compound of the invention, or a salt thereof, in an amount effective to modulate said immune system.

Further provided is a compound of the invention, or a salt thereof for use as a medicament in the treatment of the diseases or conditions described herein (e.g., cancer, autoimmune disease, infectious disease, inflammatory disorder, graft rejection, and graft-verses-host disease) in a mammal, for example, a human, suffering from such disease or condition. Also provided is the use of a compound of the invention, a salt thereof, in the preparation of a medicament for the treatment of the diseases and conditions described herein (e.g., cancer, autoimmune disease, infectious disease, inflammatory disorder, graft rejection, and graft-verses-host disease) in a mammal, for example a human, suffering from such disease or condition.

Further provided is a compound of the invention, or a salt thereof for use as a medicament in the prevention of the diseases or conditions described herein (e.g., cancer, autoimmune disease, infectious disease, inflammatory disorder, graft rejection, and graft-verses-host disease) in a mammal, for example, a human, exposed to or predisposed to the disease or condition, but the mammal does not yet experience or display symptoms of such disease or condition. Also provided is the use of a compound of the invention, a salt thereof, in the preparation of a medicament for the treatment of the diseases and conditions described herein (e.g., cancer, autoimmune disease, infectious disease, inflammatory disorder, graft rejection, and graft-verses-host disease) in a mammal, for example a human, suffering from such disease or condition.

The disease or condition is selected from, for example, cancer, autoimmune disease, infectious disease, inflammatory disorder, graft rejection, and graft-verses-host disease.

This invention further provides kits comprising one or more compounds of the invention, or a salt thereof. The kit may further comprise a second compound or formulation comprising a second pharmaceutical agent.

Another aspect provides intermediates for preparing compounds of formula I. Certain compounds of formula I may be used as intermediates for other compounds of formula I.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

In certain aspects, the invention provides compositions and methods useful for modulating TLR7- and/or TLR8-mediated signaling. More specifically, one aspect of this invention provides a compound having the formula I:

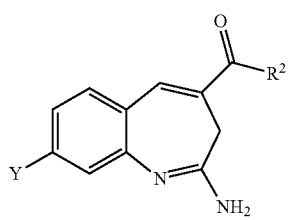

(I)

or a tautomer, enantiomer, or salt thereof, wherein:
Y is substituted aryl, heteroaryl, or substituted heteroaryl, wherein said substituted aryl or substituted heteroaryl is substituted with one or more groups independently selected from CN, OH, —C(=O)$R^9$, halogen, and —CH=CHC(=O)$R^9$;
$R^9$ is selected from alkyl, $OR^{15}$, and $NR^{10}R^{11}$;
$R^{15}$ is selected from H, alkyl, and —CH$_2$O(alkyl),
$R^{10}$ and $R^{11}$ are each independently alkyl, wherein said alkyl is optionally substituted with —OH or $R^{10}$ and $R^{11}$ together with the nitrogen atom to which they are attached form a heterocyclic ring, wherein said heterocyclic ring is optionally substituted with one or more —OH;
$R^2$ is selected from $OR^{14}$ and $NR^6R^7$;
$R^6$ and $R^7$ are each independently selected from H, alkyl, cycloalkyl, heterocycloalkyl or benzyl, wherein said alkyl, cycloalkyl, or benzyl is optionally substituted with one or more groups independently selected from —F, —$OR^8$, —$NR^{12}SO_2R^{13}$, —C(=O)$NR^{12}R^{13}$ or $R^6$ and $R^7$ together with the nitrogen atom to which they are attached form a heterocyclic ring, further wherein said heterocyclic ring is optionally substituted with one or more —OH;
$R^8$ is selected from hydrogen and alkyl, and
$R^{12}$, $R^{13}$ and $R^{14}$ are each independently selected from H and alkyl, wherein said alkyl is optionally substituted with —OH;
provided that
a) when Y is aryl substituted with

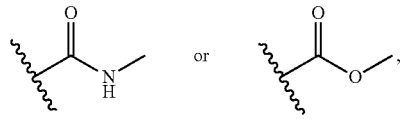

then $R^2$ is not —OCH$_2$CH$_3$ (-OEt), or
b) when Y is aryl substituted with —C(=O)$R^9$, and $R^9$=$NR^{10}R^{11}$, and $R^{10}$ and $R^{11}$ together with the nitrogen atom to which they are attached form an unsubstituted pyrrolidine ring, then $R^2$ is not -OEt or —N(propyl)$_2$.

For example, a compound of the invention is a compound of formula I, where Y is aryl substituted with

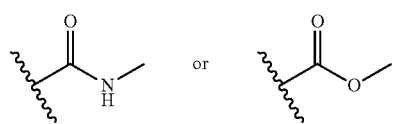

and $R^2$ is not -OEt.

In another embodiment, a compound of the invention is a compound of formula I, where Y is aryl substituted with —C(=O)$R^9$, $R^9$ is $NR^{10}R^{11}$, and $R^{10}$ and $R^{11}$ together with the nitrogen atom to which they are attached form a pyrrolidine ring, and $R^2$ is not -OEt or —N(propyl)$_2$.

In another embodiment, a compound of the invention is a compound of formula I, where Y is substituted aryl, heteroaryl, or substituted heteroaryl, wherein said substituted aryl or substituted heteroaryl is substituted with one or more groups independently selected from —C(=O)$R^9$ and —CH=CHC(=O)$R^9$. In another embodiment, a compound of the invention is a compound of formula I, wherein Y is substituted aryl, heteroaryl, or substituted heteroaryl, wherein said substituted aryl or substituted heteroaryl is substituted with —C(=O)$R^9$. In another embodiment, a compound of the invention is a compound of formula I, wherein Y is substituted aryl, heteroaryl, or substituted heteroaryl, wherein said substituted aryl or substituted heteroaryl is substituted with —CH=CHC(=O)$R^9$.

One aspect of the invention relates to a compound having the formula II:

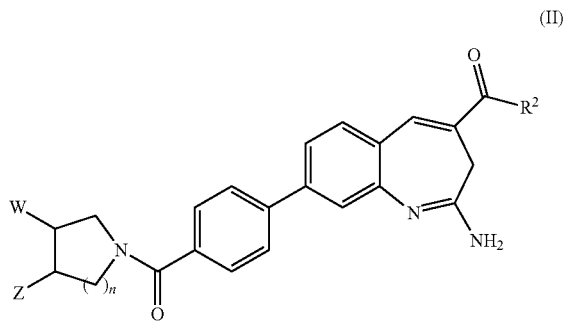

(II)

or a tautomer, enantiomer, or salt thereof, wherein W is H or —OH; Z is H or —OH; n is 1 or 2 and $R^2$ is as described for formula I. In one embodiment, the invention relates to a compound or salt thereof, having the formula II, provided that when W and Z are both H, n is 1, then $R^2$ is not -OEt or —N(propyl)$_2$.

In one embodiment, the invention relates to a compound having formula IIa:

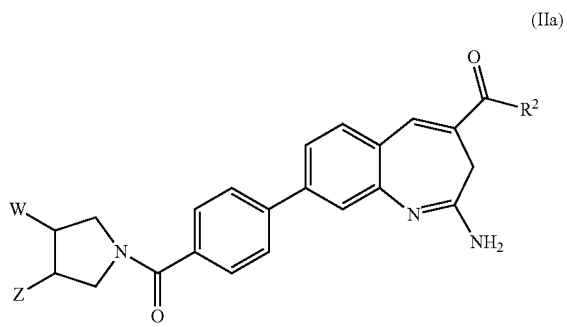

(IIa)

or a tautomer, enantiomer, or salt thereof, wherein W is H or —OH; Z is H or —OH, and $R^2$ is as described for formula I. In one embodiment, the invention relates to a compound or salt thereof, having the formula IIa, provided that when W and Z are both H, then $R^2$ is not -OEt or —N(propyl)$_2$.

In one embodiment, the invention relates to a compound having formula IIb:

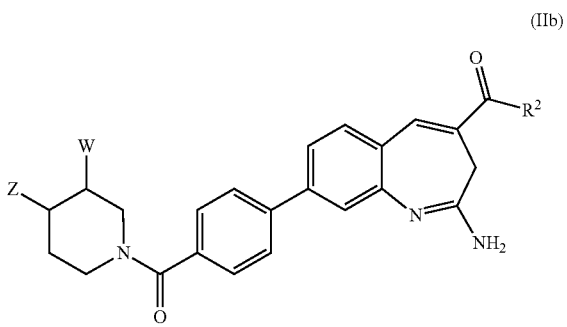

(IIb)

or a tautomer, enantiomer, or salt thereof, wherein W is H or —OH; Z is H or —OH and $R^2$ is as described for formula I.

In one embodiment, the invention relates to a compound or salt thereof, having the formula II or IIa, wherein W is H and Z is H. In one embodiment, the invention relates to a compound or salt thereof, wherein one of W or Z is H and the other is —OH. In one embodiment, the invention relates to a compound or salt thereof, wherein W is H and Z is —OH. In one embodiment, the invention relates to a compound or salt thereof, wherein W is —OH and Z is H. In one embodiment, the invention relates to a compound or salt thereof, wherein W is —OH and Z is —OH.

In one embodiment, the invention relates to a compound or salt thereof, having the formula II or IIa, wherein the stereochemistry of the stereogenic center adjacent to Z is the R-configuration. In one embodiment, the invention relates to a compound or salt thereof, wherein the stereochemistry of the stereogenic center adjacent to Z is the S-configuration. In one embodiment, the invention relates to a compound or salt thereof, wherein the stereochemistry of the stereogenic center adjacent to W is the R-configuration. In one embodiment, the invention relates to a compound or salt thereof, wherein the stereochemistry of the stereogenic center adjacent to W is the S-configuration. In one embodiment, the invention relates to a compound or salt thereof, wherein the stereochemistry of the stereogenic center adjacent to Z is the R-configuration and the stereocenter adjacent to W is the S-configuration. In one embodiment, the invention relates to a compound or salt thereof, wherein the stereochemistry of the stereogenic center adjacent to Z is the R-configuration and the stereocenter adjacent to W is the R-configuration. In one embodiment, the invention relates to a compound or salt thereof, wherein the stereochemistry of the stereogenic center adjacent to Z is the S-configuration and the stereocenter adjacent to W is the R-configuration. In one embodiment, the invention relates to a compound or salt thereof, wherein the stereochemistry of the stereogenic center adjacent to Z is the S-configuration and the stereocenter adjacent to W is the S-configuration.

One aspect of the invention relates to a compound having the formula III:

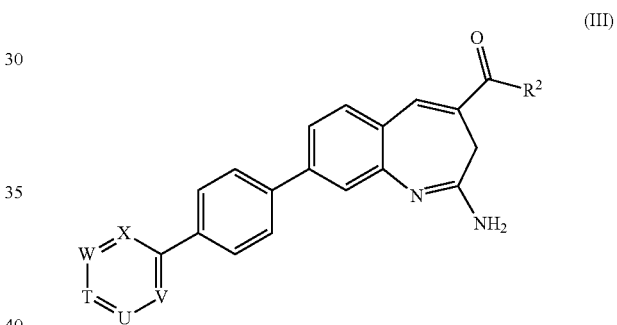

(III)

or a tautomer, enantiomer, or salt thereof, wherein
T is CH, CZ, or N;
U is CH, CZ, or N;
V is CH, CZ, or N,
X is CH, CZ, or N,
W is CH, CZ, or N,
Z is selected from halogen, —CN, —CONR$^{16}$R$^{17}$, —COOR$^{18}$, —CH=CHCOOR$^{18}$, and —OR$^{19}$; R$^{16}$, R$^{17}$, R$^{18}$, and R$^{19}$ are each independently selected from H, alkyl, and —CH$_2$O(alkyl); and R$^2$ is as described for formula I.

In one embodiment, the invention relates to a compound having the formula IIIa:

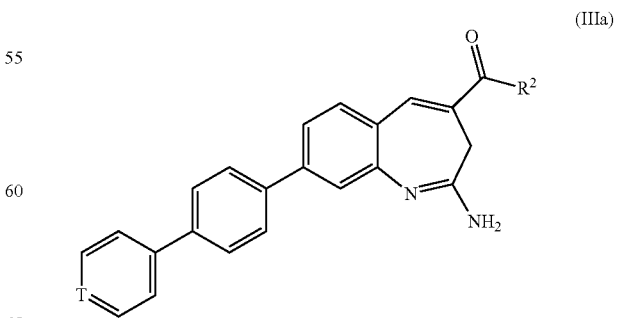

(IIIa)

or a tautomer, enantiomer, or salt thereof, wherein T is CH, CZ, or N; Z is selected from halogen, —CN, —CONR$^{16}$R$^{17}$, —COOR[18], —CH=CHCOOR[18], and —OR[19]; R[16], R[17], R[18], and R[19] are each independently selected from H, alkyl, and —CH$_2$O(alkyl); and R[2] is as described for formula I.

In one embodiment, the invention relates to a compound, having the formula IIIb:

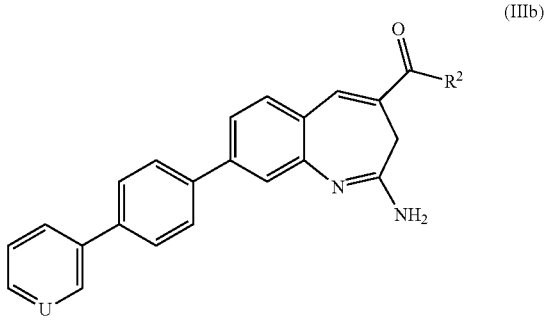

(IIIb)

or a tautomer, enantiomer, or salt thereof, wherein U is CH, CZ, or N; Z is selected from halogen, —CN, —CONR[16]R[17], —COOR[18], —CH=CHCOOR[18], and —OR[19]; R[16], R[17], R[18], and R[19] are each independently selected from H, alkyl, and —CH$_2$O(alkyl); and R[2] is as described for formula I.

In one embodiment, the invention relates to a compound having the formula IIIc:

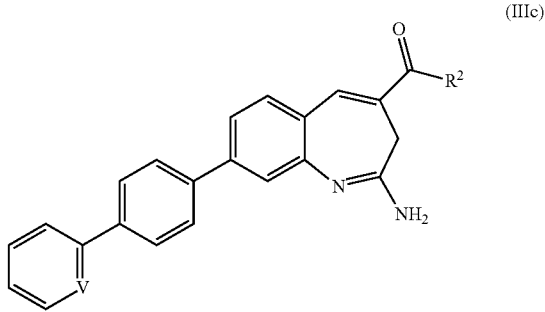

(IIIc)

or a tautomer, enantiomer, or salt thereof, wherein V is CH, CZ, or N; Z is selected from halogen, —CN, —CONR[16]R[17], —COOR[18], —CH=CHCOOR[18], and —OR[19]; R[16], R[17], R[18], and R[19] are each independently selected from H, alkyl, and —CH$_2$O(alkyl); and R[2] is as described for formula I.

In one embodiment, the invention relates to a compound having the formula IIId:

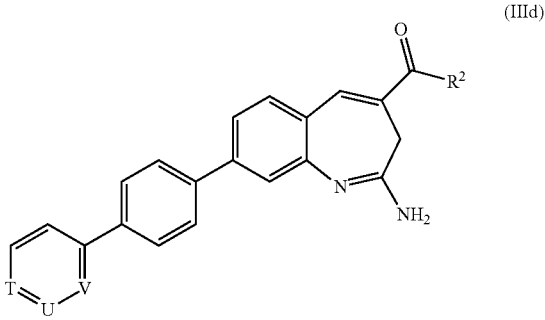

(IIId)

or a tautomer, enantiomer, or salt thereof, wherein T, U and V are each independently selected from CH, CZ, or N; Z is selected from halogen, —CN, —CONR[16]R[17], —COOR[18], —CH=CHCOOR[18], and —OR[19]; R[16], R[17], R[18], and a R[19] are each independently selected from H, alkyl, and —CH$_2$O (alkyl); and R[2] is as described for formula I.

In one embodiment, the invention relates to a compound or salt thereof, having the formula III, IIIa, IIIb, IIIc, IIId or salt thereof, wherein Z is CN.

In one embodiment, the invention relates to a compound or salt thereof, having the formula III, IIIa, IIIb, IIIc, IIId or salt thereof, wherein Z is CONR[16]R[17]. In one embodiment, the invention relates to a compound or salt thereof, wherein R[16] and R[17] are both alkyl. In one embodiment, the invention relates to a compound or salt thereof, wherein alkyl is selected from methyl and ethyl. In one embodiment, the invention relates to a compound or salt thereof, wherein alkyl is methyl. In one embodiment, the invention relates to a compound or salt thereof, wherein alkyl is ethyl.

In one embodiment, the invention relates to a compound or salt thereof, having the formula III, IIIa, IIIb, IIIc, IIId or salt thereof, wherein Z is COOR[18]. In one embodiment, the invention relates to a compound or salt thereof, wherein R[18] is H. In one embodiment, the invention relates to a compound or salt thereof, wherein R[18] is alkyl. In one embodiment, the invention relates to a compound or salt thereof, wherein alkyl is selected from methyl and ethyl.

In one embodiment, the invention relates to a compound or salt thereof, having the formula III, IIIa, IIIb, IIIc, IIId or salt thereof, wherein Z is OR[19]. In one embodiment, the invention relates to a compound or salt thereof, wherein R[19] is H.

In one embodiment, the invention relates to a compound or salt thereof, having the formula III, IIIa, IIIb, IIIc, IIId or salt thereof, wherein Z is —CH$_2$O(alkyl). In one embodiment, the invention relates to a compound or salt thereof, wherein alkyl is ethyl.

In one embodiment, the invention relates to a compound or salt thereof, having the formula III, IIIa, IIIb, IIIc, IIId or salt thereof, wherein Z is halogen.

In one embodiment, the invention relates to a compound or salt thereof, having the formula III, IIIa, IIIb, IIIc, IIId or salt thereof, wherein Z is —CH=CHCOOR[18].

One aspect of the invention relates to a compound having the formula IV:

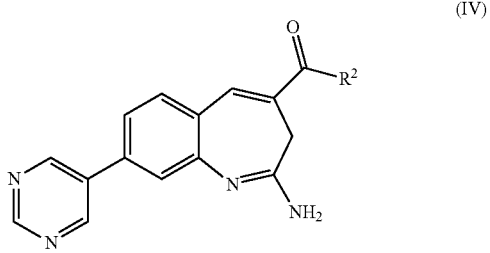

(IV)

or a tautomer, enantiomer, or salt thereof, wherein R[2] is as described for formula I.

One aspect of the invention relates to a compound having the formula V:

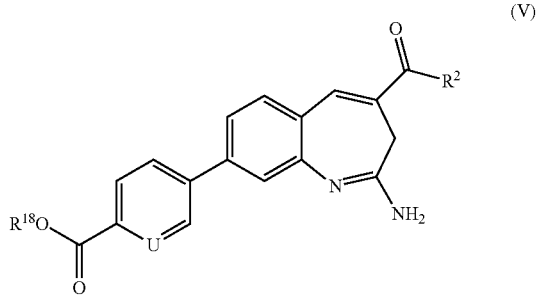

(V)

or a tautomer, enantiomer, or salt thereof, wherein U is N or CZ; Z is halogen; R[18] is selected from H, alkyl, and —CH$_2$O (alkyl); and R[2] is as described for formula I. In one embodiment, the invention relates to a compound or salt thereof, wherein R[18] is ethyl or methyl.

One aspect of the invention relates to a compound having the formula VI:

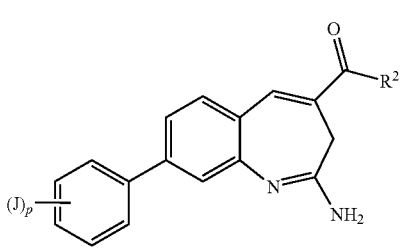

or a tautomer, enantiomer, or salt thereof, wherein
J is independently selected from halogen, —C(=O)R$^9$ and —CH=CHC(=O)R$^9$;
p is selected from 1, 2, and 3;
R$^2$ is selected from OR$^{14}$ and NR$^6$R$^7$;
R$^6$ and R$^7$ are each independently selected from H, alkyl, cycloalkyl, heterocycloalkyl or benzyl, wherein said alkyl, cycloalkyl, or benzyl is optionally substituted with one or more groups independently selected from —F, —OR$^8$, —NR$^{12}$SO$_2$R$^{13}$, —C(=O)NR$^{12}$R$^{13}$, or R$^6$ and R$^7$ together with the nitrogen atom to which they are attached form a heterocyclic ring, further wherein said heterocyclic ring is optionally substituted with one or more —OH;
R$^8$ is selected from hydrogen and alkyl;
R$^9$ is selected from alkyl, OR$^{15}$, and NR$^{10}$R$^{11}$;
R$^{10}$ and R$^{11}$ are each independently alkyl, wherein said alkyl is optionally substituted with —OH or R$^{10}$ and R$^{11}$ together with the nitrogen atom to which they are attached form a heterocyclic ring, wherein said heterocyclic ring is optionally substituted with one or more —OH;
R$^{12}$, R$^{13}$ and R$^{14}$ are each independently selected from H and alkyl; and
R$^{15}$ is selected from H, alkyl, and —CH$_2$O(alkyl). In one embodiment, the invention relates to a compound or a salt thereof, having the formula VI, provided that when p is 1 and J is

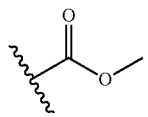

attached at the 4-position of the aryl ring, then R$^2$ is not -OEt, and further provided that when p is 1 and J is

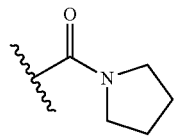 [SMILES: *C(=O)N1CCCC1]

attached at the 4-position of the aryl ring, then R$^2$ is not -OEt or —N(propyl)$_2$.

In one embodiment, the invention relates to a compound or salt thereof, having the formula VI, wherein J is attached at the 4-position of the aryl ring. In one embodiment, the invention relates to a compound or salt thereof, wherein J is attached at the 3-position of the aryl ring. In one embodiment, the invention relates to a compound or salt thereof, wherein J is attached at the 2-position of the aryl ring. In one embodiment, the invention relates to a compound or salt thereof, wherein J is —CH=CHC(=O)R$^9$.

In one embodiment, the invention relates to a compound or salt thereof, having the formula VI, wherein J is —C(=O)R$^9$. In one embodiment, the invention relates to a compound or salt thereof, wherein p is 2, one J is —C(=O)R$^9$, and the other J is halogen. In one embodiment, the invention relates to a compound or salt thereof, wherein R$^9$ is OR$^{15}$. In one embodiment, the invention relates to a compound or salt thereof, wherein R$^{15}$ is alkyl. In one embodiment, the invention relates to a compound or salt thereof, wherein R$^{15}$ is selected from ethyl and methyl. In one embodiment, the invention relates to a compound or salt thereof, wherein one J is —C(=O)R$^9$ and the other J is F. In one embodiment, the invention relates to a compound or salt thereof, wherein R$^9$ is OR$^{15}$. In one embodiment, the invention relates to a compound or salt thereof, wherein R$^{15}$ is —CH$_2$O(alkyl).

One aspect of the invention relates to a compound having the formula VII:

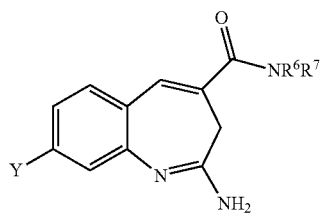

or a tautomer, enantiomer or salt thereof, wherein:
Y is substituted aryl or substituted heteroaryl, wherein said aryl or heteroaryl is substituted with one or more groups independently selected from —C(~O)R$^9$, halogen, and —CH=CHC(=O)R$^9$;
R$^9$ is selected from alkyl, OR$^{15}$, and NR$^{10}$R$^{11}$;
R$^{15}$ is selected from H, alkyl, and —CH$_2$O(alkyl);
R$^{10}$ and R$^{11}$ are each independently alkyl, wherein said alkyl is optionally substituted with —OH or R$^{10}$ and R$^{11}$ together with the nitrogen atom to which they are attached form a heterocyclic ring, wherein said heterocyclic ring is optionally substituted with one or more —OH; and
R$^6$ and R$^7$ are each independently selected from H, alkyl or alkenyl, wherein said alkyl or alkenyl is optionally substituted with one or more groups independently selected from —F or —OH;
provided that when Y is aryl substituted with —C(=O)R$^9$, and R$^9$=NR$^{10}$R$^{11}$, and R$^{10}$ and R$^{11}$ together with the nitrogen atom to which they are attached form an unsubstituted pyrrolidine ring, then R$^6$ and R$^7$ are not both propyl.

In another embodiment, the invention relates to a compound having the formula VII, wherein:
Y is substituted aryl or substituted heteroaryl, wherein said aryl or heteroaryl is substituted with one or more groups independently selected from —C(=O)R$^9$, halogen, and —CH=CHC(=O)R$^9$;
R$^9$ is OR$^{15}$;
R$^{15}$ is selected from H, alkyl, and —CH$_2$O(alkyl); and
R$^6$ and R$^7$ are each independently selected from H, alkyl or alkenyl, wherein said alkyl or alkenyl is optionally substituted with one or more groups independently selected from —F or —OH.

In another embodiment, the invention relates to a compound having the formula VII, wherein:
Y is substituted aryl, wherein said aryl is substituted with —C(=O)R$^9$;
R$^9$ is selected from alkyl, OR$^{15}$, and NR$^{10}$R$^{11}$;
R$^{15}$ is selected from H, alkyl, and —CH$_2$O(alkyl), $R^{10}$ and $R^{11}$ together with the nitrogen atom to which they are attached form a heterocyclic ring, wherein said heterocyclic ring is optionally substituted with one or more —OH; and $R^6$ and $R^7$ are each independently selected from H, alkyl or alkenyl, wherein said alkyl or alkenyl is optionally substituted with one or more groups independently selected from —F or —OH;

provided that when $R^9$=$NR^{10}R^{11}$, and $R^{10}$ and $R^{11}$ together with the nitrogen atom to which they are attached form an unsubstituted pyrrolidine ring, then $R^6$ and $R^7$ are not both propyl.

In another embodiment, the invention relates to a compound having the formula VII, wherein $R^6$ and $R^7$ are each independently alkyl, wherein said alkyl is substituted with one or more groups independently selected from —F and —OH. In another embodiment, the invention relates to a compound having the formula VII, wherein $R^6$ and $R^7$ are each independently alkyl, wherein said alkyl is unsubstituted. In another embodiment, the invention relates to a compound having the formula VII, wherein Y is substituted aryl. In another embodiment, the invention relates to a compound having the formula VII, wherein Y is substituted phenyl. In another embodiment, the invention relates to a compound having the formula VII, wherein Y is substituted heteroaryl.

In another embodiment, the invention relates to a compound having the formula VIIa:

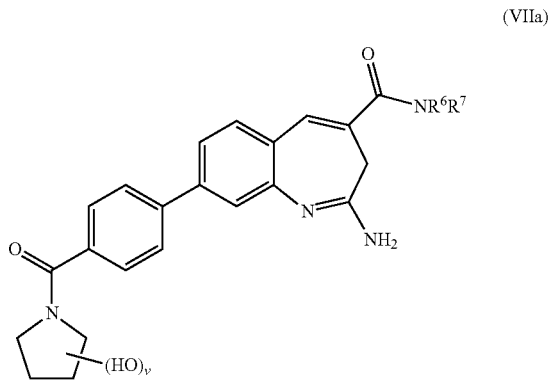

(VIIa)

or a tautomer, enantiomer or salt thereof, wherein:

v is 0, 1, or 2;

$R^6$ is selected from H, allyl, prop-1-enyl, and propyl, wherein said propyl is optionally substituted with one or more —OH;

$R^7$ is selected from allyl, prop-1-enyl, and propyl, wherein said propyl is optionally substituted with one or more —OH;

provided that when v is 0, then $R^6$ and $R^7$ are not both propyl.

In another embodiment, the invention relates to a compound having the formula VIIa wherein $R^6$ and $R^7$ are each independently propyl, wherein said propyl is optionally substituted with one or more —OH. In another embodiment, the invention relates to a compound having the formula VIIa wherein $R^6$ and $R^7$ are each independently propyl, wherein one of $R^6$ or $R^7$ is substituted with one or more —OH and the other is unsubstituted. In another embodiment, the invention relates to a compound having the formula VIIa wherein $R^6$ and $R^7$ are each unsubstituted propyl. In another embodiment, the invention relates to a compound having the formula VIIa wherein v is 0. In another embodiment, the invention relates to a compound having the formula VIIa wherein v is 1 or 2.

One aspect of the invention relates to a compound or salt thereof, having the formula I, II, IIa, IIb, III, IIIa, IIIb, IIIc, IIId, IV, V, or VI, wherein $R^2$ is —$OR^{14}$. In one embodiment, the invention relates to a compound or a salt thereof, wherein $R^{14}$ is alkyl. In one embodiment, the invention relates to a compound or a salt thereof, wherein alkyl is ethyl.

One aspect of the invention relates to a compound or a salt thereof, having the formula I, II, IIa, IIb, III, IIIa, IIIb, IIIc, IIId, IV, V, or VI, wherein $R^2$ is —$NR^6R^7$. In one embodiment, the invention relates to a compound or a salt thereof, wherein one of $R^6$ or $R^7$ is H and the other is alkyl. In one embodiment, the invention relates to a compound or a salt thereof, wherein both $R^6$ and $R^7$ are each independently alkyl. In one embodiment, the invention relates to a compound or a salt thereof, wherein each alkyl is independently selected from isopropyl, propyl, isobuytyl, and secbutyl. In one embodiment, the invention relates to a compound or a salt thereof, wherein alkyl is optionally substituted with one or more —OH. In one embodiment, the invention relates to a compound or a salt thereof, wherein alkyl is substituted with one —OH. In one embodiment, the invention relates to a compound or a salt thereof, wherein the stereocenter adjacent to the —OH group is the S-configuration.

In one embodiment, the invention relates to a compound or a salt thereof, wherein the stereocenter adjacent to the OH group is the R-configuration. In one embodiment, the invention relates to a compound or a salt thereof, wherein alkyl is substituted with two —OH. In one embodiment, the invention relates to a compound or a salt thereof, wherein alkyl is optionally substituted with one or more —O(alkyl). In one embodiment, the invention relates to a compound or a salt thereof, wherein alkyl is substituted with one —O(alkyl). In one embodiment, the invention relates to a compound or a salt thereof, wherein alkyl is substituted two —O(alkyl).

One aspect of the invention relates to a compound or a salt thereof, having the formula I, II, IIa, IIb, III, IIIa, IIIb, IIIc, IIId, IV, V, or VI, wherein $R^2$ is —$NR^6R^7$. In one embodiment, the invention relates to a compound or a salt thereof, wherein one of $R^6$ or $R^7$ is alkyl, and the other is benzyl. In one embodiment, the invention relates to a compound or a salt thereof, wherein benzyl is substituted with —OH.

One aspect of the invention relates to a compound or a salt thereof, having the formula I, II, IIa, IIb, III, IIIa, IIIb, IIIc, IIId, IV, V, or VI, wherein $R^2$ is —$NR^6R^7$. In one embodiment, the invention relates to a compound or a salt thereof, wherein at least one of $R^6$ or $R^7$ is alkyl. In one embodiment, the invention relates to a compound or a salt thereof, wherein one alkyl is substituted with —$NR^{12}SO_2R^{13}$. In one embodiment, the invention relates to a compound or a salt thereof, wherein $R^{12}$ is H. In one embodiment, the invention relates to a compound or a salt thereof, wherein $R^{13}$ is methyl.

One aspect of the invention relates to a compound or a salt thereof, having the formula I, II, IIa, IIb, III, IIIa, IIIb, IIIc, IIId, IV, V, or VI, wherein $R^2$ is —$NR^6R^7$. In one embodiment, the invention relates to a compound or a salt thereof, wherein at least one of $R^6$ or $R^7$ is alkyl. In one embodiment, the invention relates to a compound or a salt thereof, wherein one alkyl is substituted with —C(=O)$NR^{12}R^{13}$. In one embodiment, the invention relates to a compound or a salt thereof, wherein $R^{12}$ and $R^{13}$ are both H.

One aspect of the invention relates to a compound or a salt thereof, having the formula I, II, IIa, IIb, III, IIIa, IIIb, IIIc, IIId, IV, V, or VI, wherein $R^2$ is —$NR^6R^7$. In one embodiment, the invention relates to a compound or a salt thereof, wherein at least one of $R^6$ or $R^7$ is alkyl. In one embodiment, the invention relates to a compound or a salt thereof, wherein alkyl is substituted with halogen.

One aspect of the invention relates to a compound or a salt thereof, having the formula I, II, IIa, IIb, III, IIIa, IIIb, IIIc, IIId, IV, V, or VI, wherein $R^2$ is —$NR^6R^7$. In one embodiment, the invention relates to a compound or a salt thereof, wherein $R^6$ and $R^7$ are both propyl. In one embodiment, the invention relates to a compound or a salt thereof, wherein, wherein one of $R^6$ or $R^7$ is cycloalkyl and the other is heterocycloalkyl. In one embodiment, the invention relates to a compound or a salt thereof, wherein cycloalkyl is cyclopropyl. In one embodiment, the invention relates to a compound or a salt thereof, wherein heterocycloalkyl is piperidine.

One aspect of the invention relates to a compound or a salt thereof, having the formula I, II, IIa, IIb, III, IIIa, IIIb, IIIc, IIId, IV, V, or VI, wherein $R^2$ is —$NR^6R^7$. In one embodiment, the invention relates to a compound or a salt thereof, wherein $R^6$ and $R^7$ together with the nitrogen atom to which they are attached form a heterocyclic ring. In one embodiment, the invention relates to a compound, wherein the heterocyclic ring is selected from pyrrolidine and piperidine.

One aspect of the invention relates to a compound or a salt thereof, selected from a compound in Table 1 (formula I). In one embodiment, the invention relates to a compound or a salt thereof, selected from Compound 156, 101, 102, 103, 104, 105, 106, 107, 109, 110, 112, 117, 119, 120, 174, 176, 178, 127, 128, 129, 130, 182, 115, 121, 122, 126, and 202 (formula II). In one embodiment, the invention relates to a compound or a salt thereof, selected from Compound 101, 102, 103, 104, 105, 106, 107, 109, 110, 112, 117, 119, 120, 174, 176, 178, 127, 128, 129, 130, 182, 115, 121, 122, and 202 (formula IIa). In one embodiment, the invention relates to a compound or a salt thereof selected from Compound 126 and 156 (formula IIb). In one embodiment, the invention relates to a compound or a salt thereof; selected from Compound 143, 146, 154, 155, 124, 125, 134, 137, 139, 188, 190, 195, 202, 206, 207, 208, 209, and 220 (formula IIIa). In one embodiment, the invention relates to a compound or a salt thereof, selected from Compound 142, 145, 147, 133, 136, 138, 186, 187, and 194 (formula IIIb). In one embodiment, the invention relates to a compound or a salt thereof, selected from Compound 141, 203, and 204 (formula IIIc). In one embodiment, the invention relates to a compound or a salt thereof, selected from Compound 144 and 135 (formula IV). In one embodiment, the invention relates to a compound or a salt thereof; selected from Compound 210, 211, and 212 (formula V). In one embodiment, the invention relates to a compound or a salt thereof, selected from Compound 139, 220, 211, 187, 190, 203, 204, 206, 207, 208, 212, and 210 (formula VI). In one embodiment, the invention relates to a compound or a salt thereof, selected from Compound 101, 102, 103, 104, 105, 106, 107, 109, 110, 117, 124, 125, 126, 127, 128, 129, 130, 138, 139, 220, 186, 182, 187, 188, 190, 202, 203, 204, 206, 207, 208, 209, 212, 227, 228, 229, 230, 231, 232, 233, 234, 235, 236, 237, 238, and 239 (formula VII). In one embodiment, the invention relates to a compound or a salt thereof, selected from Compound 101, 104, 105, 106, 109, 110, 127, 128, 129, 130, 182, 227, 228, 229, 230, 231, 232, 233, 234, 235, 236, 237, 238, and 239 (formula VIIa).

One aspect of the invention relates to a salt of a compound of the invention, wherein the salt is a pharmaceutically acceptable salt.

One aspect of the invention relates to a kit for treating a TLR7- and/or TLR8-mediated condition, comprising:

a) a first pharmaceutical composition comprising a compound of the invention or a salt thereof; and b) optionally instructions for use.

In one embodiment, the invention relates to the kit further comprising (c) a second pharmaceutical composition, wherein the second pharmaceutical composition comprises a second compound for treating a TLR7- and/or TLR8-mediated condition. In one embodiment, the invention relates to the kit, further comprising instructions for the simultaneous, sequential or separate administration of said first and second pharmaceutical compositions to a patient in need thereof.

One aspect of the invention relates to a pharmaceutical composition, which comprises a compound of the invention or a salt thereof, together with a pharmaceutically acceptable diluent or carrier.

One aspect of the invention relates to a compound of the invention for use as a medicament for treating a TLR7 and/or TLR8-mediated condition in a human or animal. In one embodiment, the invention relates to a compound of the invention or a salt thereof, in the manufacture of a medicament for the treatment of an abnormal cell growth condition in a human or animal.

One aspect of the invention relates to a method of treating a TLR7- and/or TLR8-mediated condition, comprising administering to a patient in need thereof an effective amount of a compound of the invention or a salt thereof.

One aspect of the invention relates to a method of modulating a patient's immune system, comprising administering to a patient in need thereof an effective amount of a compound of the invention or a salt thereof.

The invention includes a compound selected from the compounds listed in Table 1.

TABLE 1

| # | Chemical Structure |
|---|---|
| 101 | 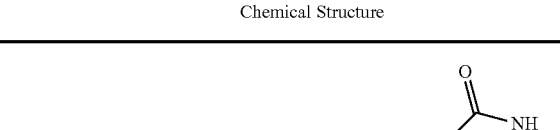 |

TABLE 1-continued

| # | Chemical Structure |
|---|---|
| 102 | 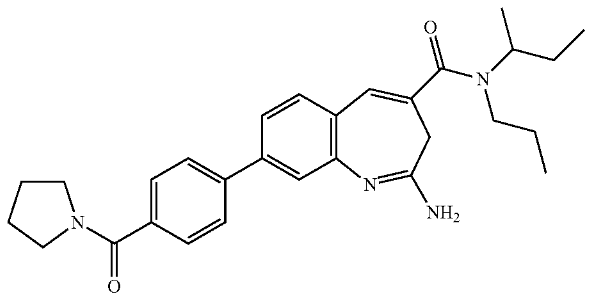 [SMILES: CCCN(C(=O)C1=Cc2ccc(-c3ccc(C(=O)N4CCCC4)cc3)cc2N=C(N)C1)C(C)CC] |
| 103 | 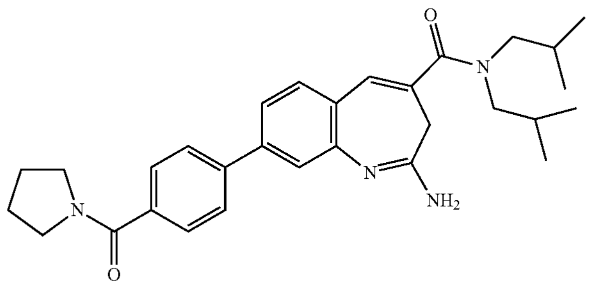 [SMILES: CC(C)CN(CC(C)C)C(=O)C1=Cc2ccc(-c3ccc(C(=O)N4CCCC4)cc3)cc2N=C(N)C1] |
| 104 | 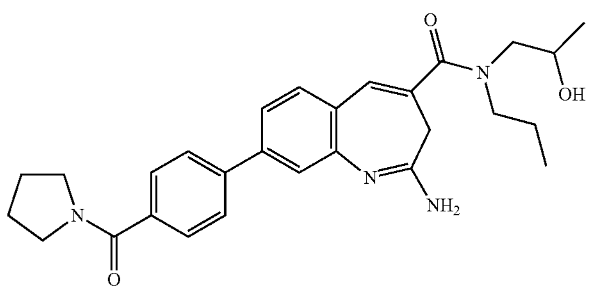 [SMILES: CCCN(CC(C)O)C(=O)C1=Cc2ccc(-c3ccc(C(=O)N4CCCC4)cc3)cc2N=C(N)C1] |
| 105 | 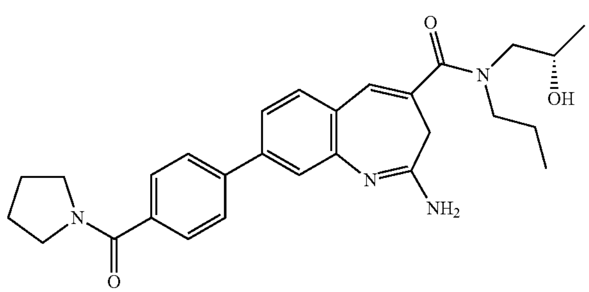 [SMILES: CCCN(C[C@H](C)O)C(=O)C1=Cc2ccc(-c3ccc(C(=O)N4CCCC4)cc3)cc2N=C(N)C1] |
| 106 | 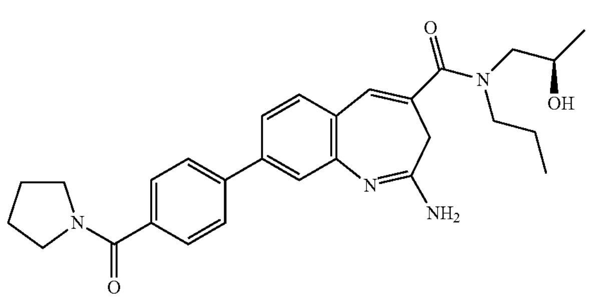 [SMILES: CCCN(C[C@@H](C)O)C(=O)C1=Cc2ccc(-c3ccc(C(=O)N4CCCC4)cc3)cc2N=C(N)C1] |

TABLE 1-continued

| # | Chemical Structure |
|---|---|
| 107 | (structure) |
| 112 | (structure) |
| 109 | (structure) |
| 110 | (structure) |
| 115 | (structure) |

TABLE 1-continued
| # | Chemical Structure |
|---|---|
| 117 | 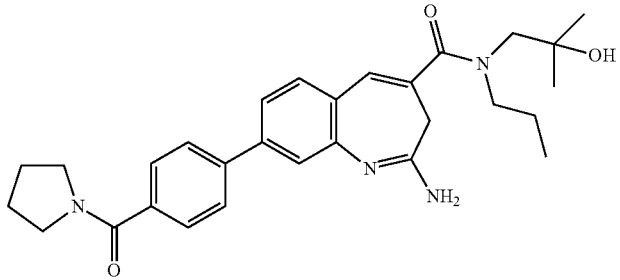 [SMILES: CCCN(CC(C)(C)O)C(=O)C1=Cc2ccc(-c3ccc(C(=O)N4CCCC4)cc3)cc2N=C(N)C1] |
| 119 | 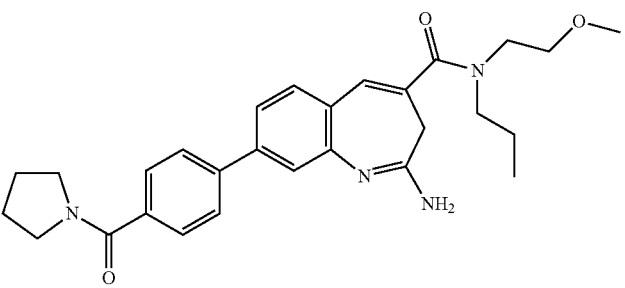 |
| 120 | 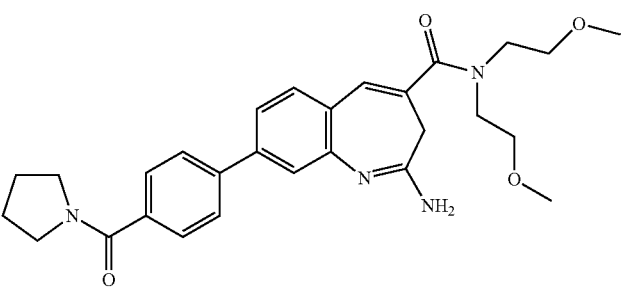 [SMILES: COCCN(CCOC)C(=O)C1=Cc2ccc(-c3ccc(C(=O)N4CCCC4)cc3)cc2N=C(N)C1] |
| 121 | 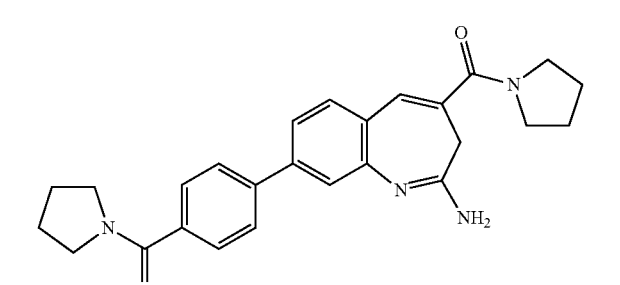 |
| 122 | 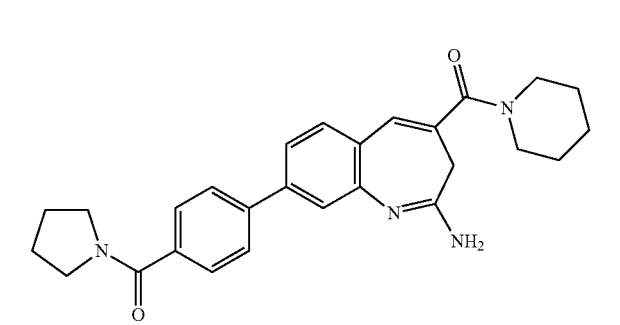 [SMILES: NC1=Nc2cc(-c3ccc(C(=O)N4CCCC4)cc3)ccc2C=C(C(=O)N2CCCCC2)C1] |

TABLE 1-continued
| # | Chemical Structure |
|---|---|
| 132 | 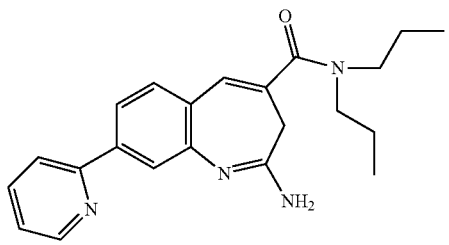 [SMILES: CCCN(CCC)C(=O)C1=Cc2ccc(-c3ccccn3)cc2N=C(N)C1] |
| 124 | 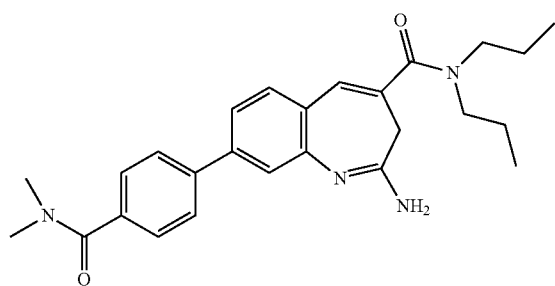 [SMILES: CCCN(CCC)C(=O)C1=Cc2ccc(-c3ccc(C(=O)N(C)C)cc3)cc2N=C(N)C1] |
| 125 | 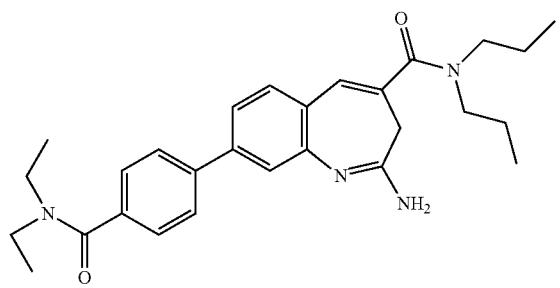 [SMILES: CCCN(CCC)C(=O)C1=Cc2ccc(-c3ccc(C(=O)N(CC)CC)cc3)cc2N=C(N)C1] |
| 126 | 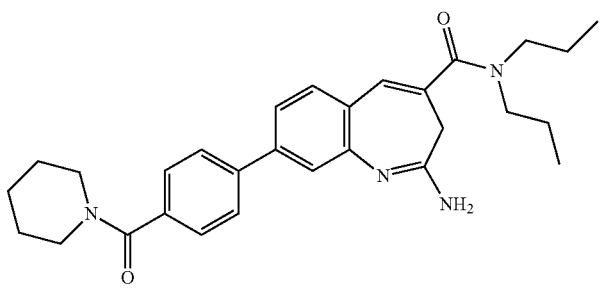 [SMILES: CCCN(CCC)C(=O)C1=Cc2ccc(-c3ccc(C(=O)N4CCCCC4)cc3)cc2N=C(N)C1] |
| 127 | 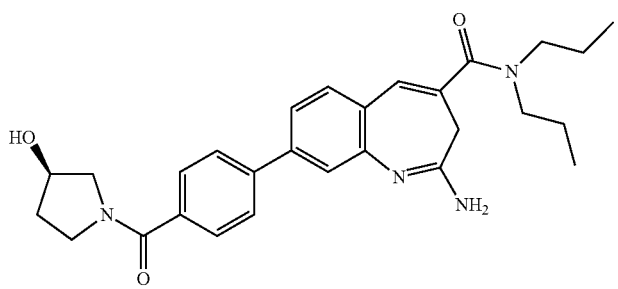 [SMILES: CCCN(CCC)C(=O)C1=Cc2ccc(-c3ccc(C(=O)N4CC[C@@H](O)C4)cc3)cc2N=C(N)C1] |

TABLE 1-continued

| # | Chemical Structure |
|---|---|
| 128 | 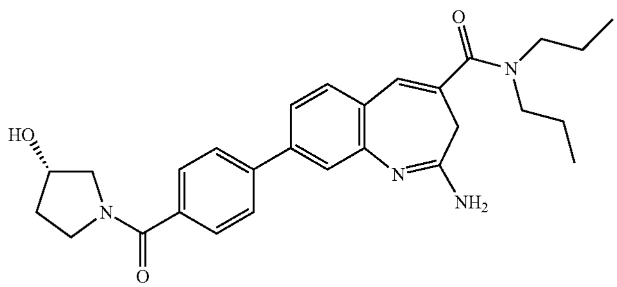 [SMILES: CCCN(CCC)C(=O)C1=Cc2ccc(-c3ccc(C(=O)N4CC[C@H](O)C4)cc3)cc2N=C(N)C1] |
| 129 | 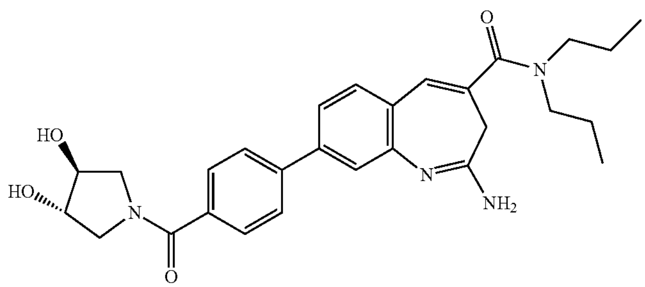 [SMILES: CCCN(CCC)C(=O)C1=Cc2ccc(-c3ccc(C(=O)N4C[C@H](O)[C@@H](O)C4)cc3)cc2N=C(N)C1] |
| 130 | 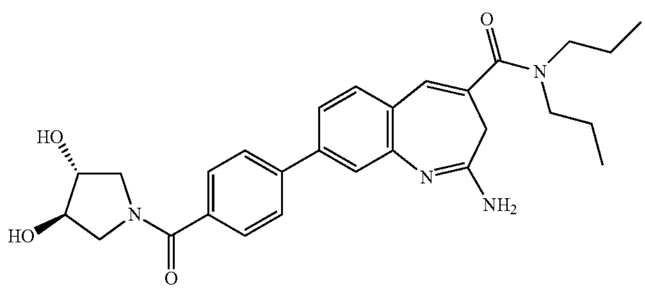 [SMILES: CCCN(CCC)C(=O)C1=Cc2ccc(-c3ccc(C(=O)N4C[C@@H](O)[C@H](O)C4)cc3)cc2N=C(N)C1] |
| 133 | 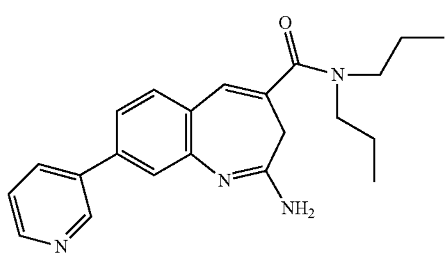 [SMILES: CCCN(CCC)C(=O)C1=Cc2ccc(-c3cccnc3)cc2N=C(N)C1] |
| 134 | 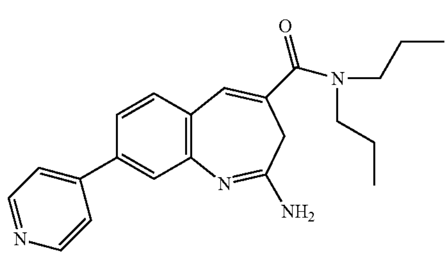 [SMILES: CCCN(CCC)C(=O)C1=Cc2ccc(-c3ccncc3)cc2N=C(N)C1] |

TABLE 1-continued

| # | Chemical Structure |
|---|---|
| 135 | 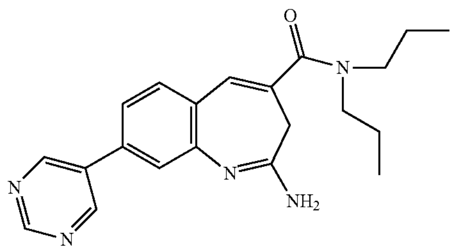 [SMILES: CCCN(CCC)C(=O)C1=Cc2ccc(-c3cncnc3)cc2N=C(N)C1] |
| 136 | 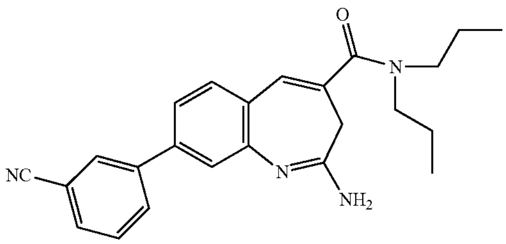 [SMILES: CCCN(CCC)C(=O)C1=Cc2ccc(-c3cccc(C#N)c3)cc2N=C(N)C1] |
| 137 | 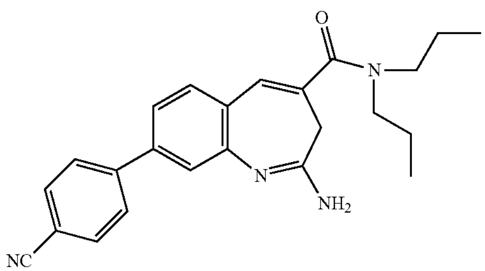 [SMILES: CCCN(CCC)C(=O)C1=Cc2ccc(-c3ccc(C#N)cc3)cc2N=C(N)C1] |
| 138 | 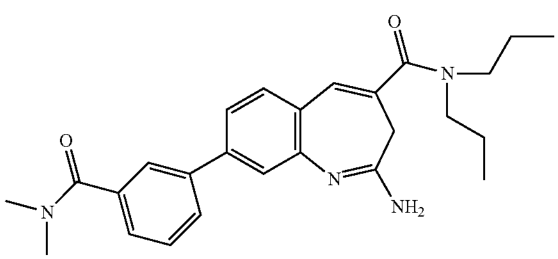 [SMILES: CCCN(CCC)C(=O)C1=Cc2ccc(-c3cccc(C(=O)N(C)C)c3)cc2N=C(N)C1] |
| 139 | 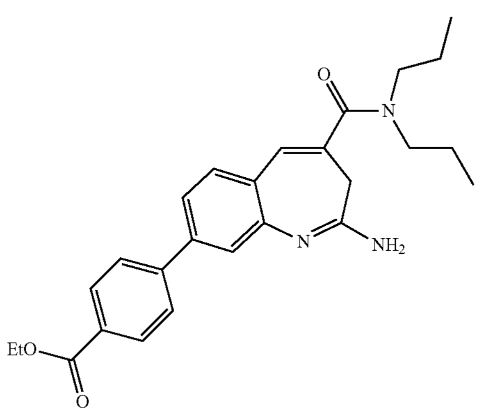 [SMILES: CCCN(CCC)C(=O)C1=Cc2ccc(-c3ccc(C(=O)OCC)cc3)cc2N=C(N)C1] |

TABLE 1-continued
| # | Chemical Structure |
|---|---|
| 154 | 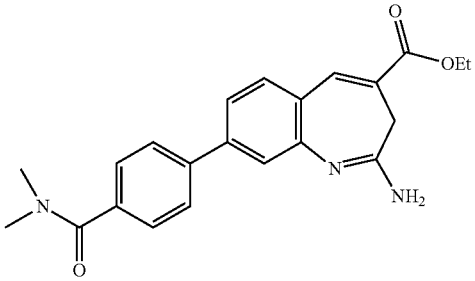 [SMILES: CCOC(=O)C1=Cc2ccc(-c3ccc(C(=O)N(C)C)cc3)cc2N=C(N)C1] |
| 141 | 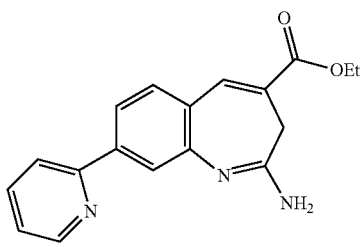 [SMILES: CCOC(=O)C1=Cc2ccc(-c3ccccn3)cc2N=C(N)C1] |
| 142 | 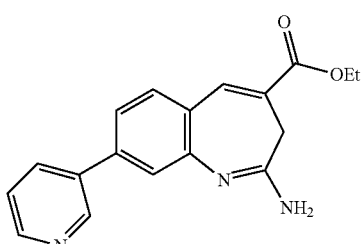 |
| 143 | 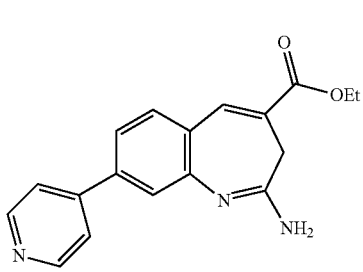 [SMILES: CCOC(=O)C1=Cc2ccc(-c3ccncc3)cc2N=C(N)C1] |
| 144 | 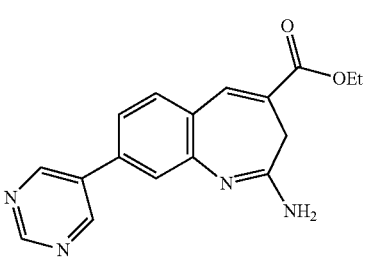 [SMILES: CCOC(=O)C1=Cc2ccc(-c3cncnc3)cc2N=C(N)C1] |
| 145 | 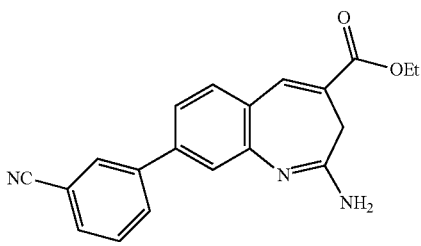 [SMILES: CCOC(=O)C1=Cc2ccc(-c3cccc(C#N)c3)cc2N=C(N)C1] |

TABLE 1-continued

| # | Chemical Structure |
|---|---|
| 146 | ethyl 2-amino-8-(4-cyanophenyl)-3H-benzo[b]azepine-4-carboxylate |
| 147 | ethyl 2-amino-8-(3-(dimethylcarbamoyl)phenyl)-3H-benzo[b]azepine-4-carboxylate |
| 220 | (E)-ethyl 3-(4-(2-amino-4-(N-(3-hydroxypropyl)-N-propylcarbamoyl)-3H-benzo[b]azepin-8-yl)phenyl)acrylate |
| 155 | ethyl 2-amino-8-(4-(diethylcarbamoyl)phenyl)-3H-benzo[b]azepine-4-carboxylate |
| 156 | ethyl 2-amino-8-(4-(piperidine-1-carbonyl)phenyl)-3H-benzo[b]azepine-4-carboxylate |

TABLE 1-continued
| # | Chemical Structure |
|---|---|
| 174 | 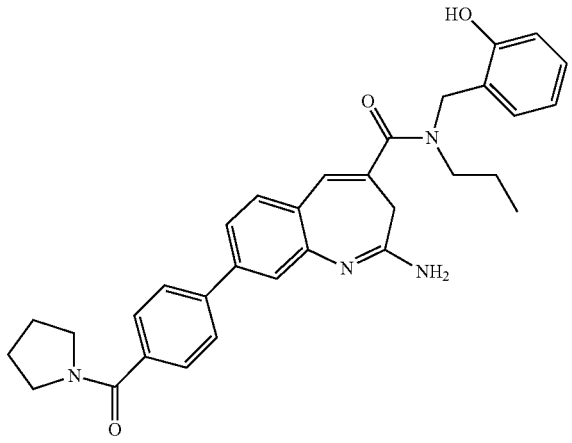 [SMILES: CCCN(Cc1ccccc1O)C(=O)C1=Cc2ccc(-c3ccc(C(=O)N4CCCC4)cc3)cc2N=C(N)C1] |
| 176 | 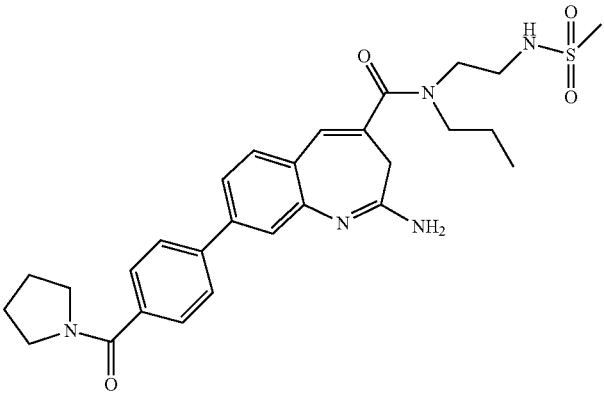 [SMILES: CCCN(CCNS(C)(=O)=O)C(=O)C1=Cc2ccc(-c3ccc(C(=O)N4CCCC4)cc3)cc2N=C(N)C1] |
| 186 | 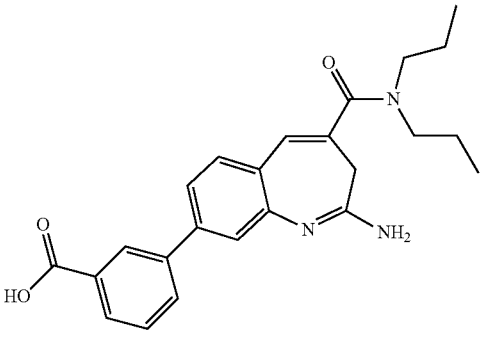 [SMILES: CCCN(CCC)C(=O)C1=Cc2ccc(-c3cccc(C(=O)O)c3)cc2N=C(N)C1] |
| 178 | 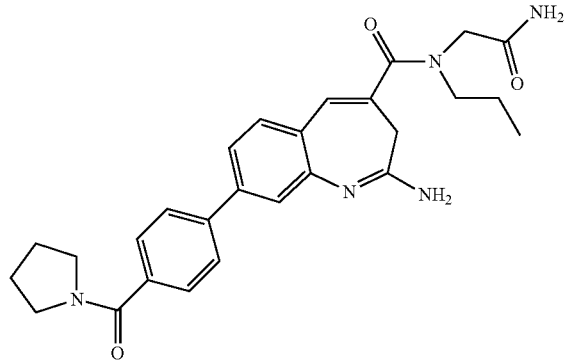 [SMILES: CCCN(CC(N)=O)C(=O)C1=Cc2ccc(-c3ccc(C(=O)N4CCCC4)cc3)cc2N=C(N)C1] |

TABLE 1-continued

| # | Chemical Structure |
|---|---|
| 211 | 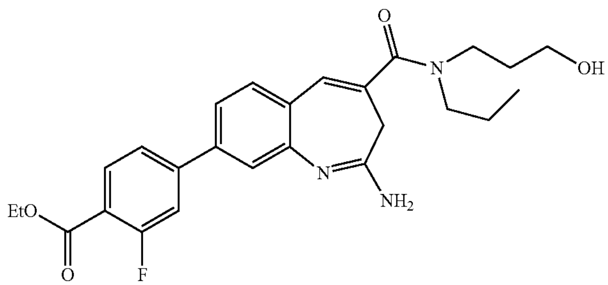 [SMILES: CCCN(CCCO)C(=O)C1=Cc2ccc(-c3ccc(C(=O)OCC)c(F)c3)cc2N=C(N)C1] |
| 182 | 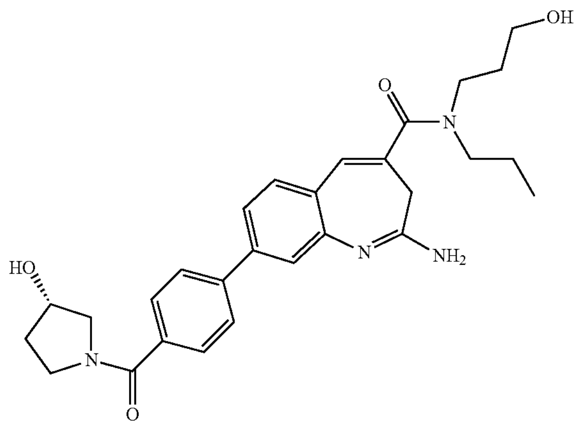 [SMILES: CCCN(CCCO)C(=O)C1=Cc2ccc(-c3ccc(C(=O)N4CC[C@H](O)C4)cc3)cc2N=C(N)C1] |
| 187 | 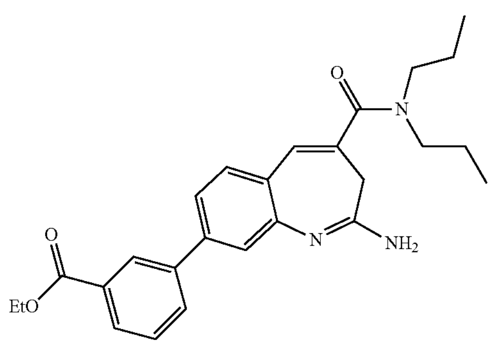 |
| 188 | 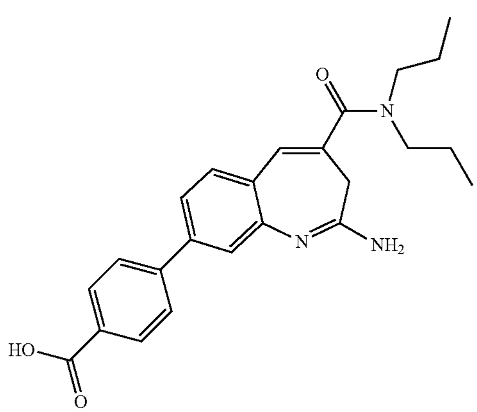 [SMILES: CCCN(CCC)C(=O)C1=Cc2ccc(-c3ccc(C(=O)O)cc3)cc2N=C(N)C1] |

TABLE 1-continued
| # | Chemical Structure |
|---|---|
| 194 | 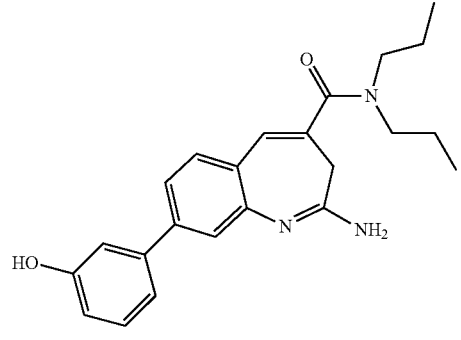 [SMILES: CCCN(CCC)C(=O)C1=Cc2ccc(-c3cccc(O)c3)cc2N=C(N)C1] |
| 190 | 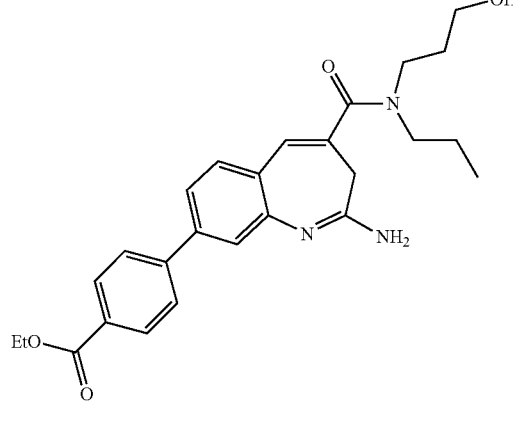 |
| 195 | 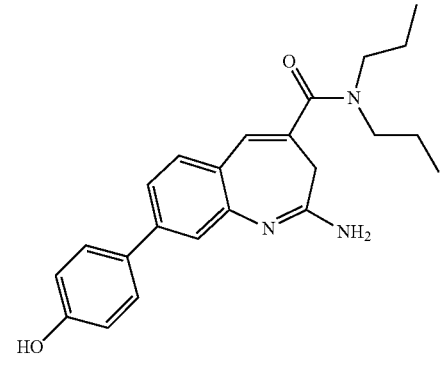 [SMILES: CCCN(CCC)C(=O)C1=Cc2ccc(-c3ccc(O)cc3)cc2N=C(N)C1] |
| 202 | 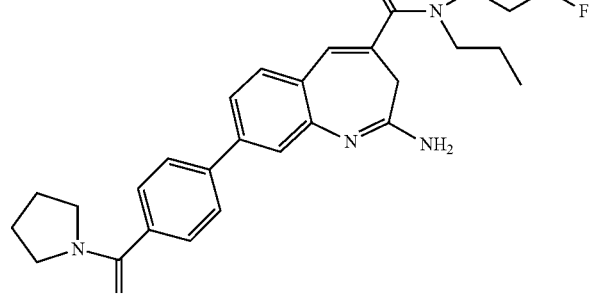 |

TABLE 1-continued

| # | Chemical Structure |
|---|---|
| 203 | 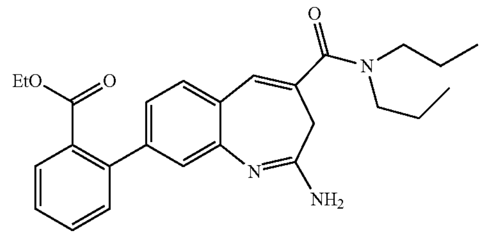 [SMILES: CCCN(CCC)C(=O)C1=Cc2ccc(-c3ccccc3C(=O)OCC)cc2N=C(N)C1] |
| 204 | 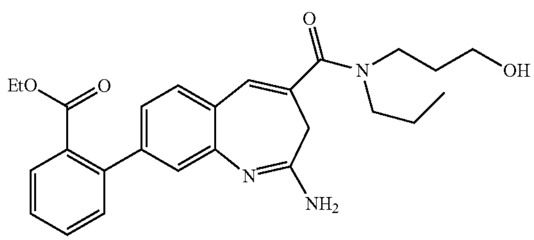 [SMILES: CCCN(CCCO)C(=O)C1=Cc2ccc(-c3ccccc3C(=O)OCC)cc2N=C(N)C1] |
| 206 | 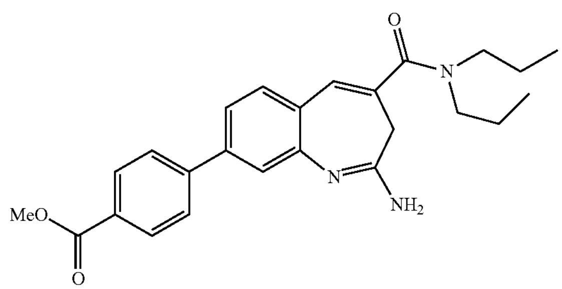 [SMILES: CCCN(CCC)C(=O)C1=Cc2ccc(-c3ccc(C(=O)OC)cc3)cc2N=C(N)C1] |
| 207 | 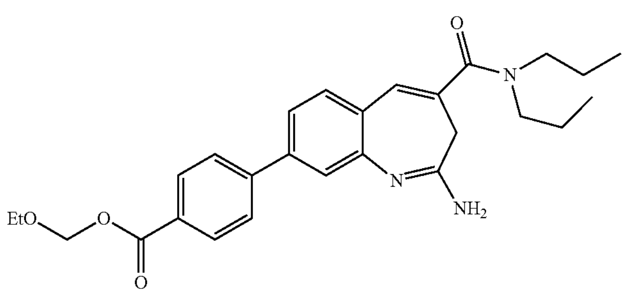 [SMILES: CCCN(CCC)C(=O)C1=Cc2ccc(-c3ccc(C(=O)OCOCC)cc3)cc2N=C(N)C1] |
| 208 | 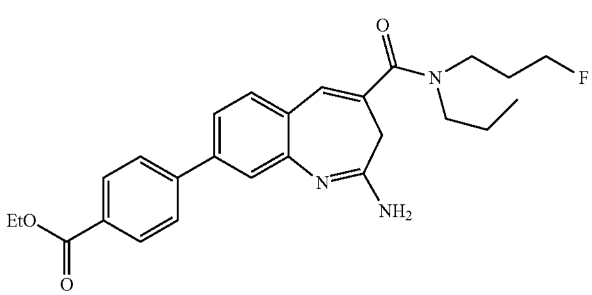 [SMILES: CCCN(CCCF)C(=O)C1=Cc2ccc(-c3ccc(C(=O)OCC)cc3)cc2N=C(N)C1] |

TABLE 1-continued

| # | Chemical Structure |
|---|---|
| 209 | 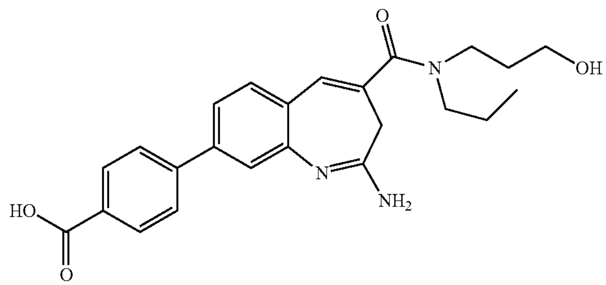 [SMILES: CCCN(CCCO)C(=O)C1=Cc2ccc(-c3ccc(C(=O)O)cc3)cc2N=C(N)C1] |
| 212 | 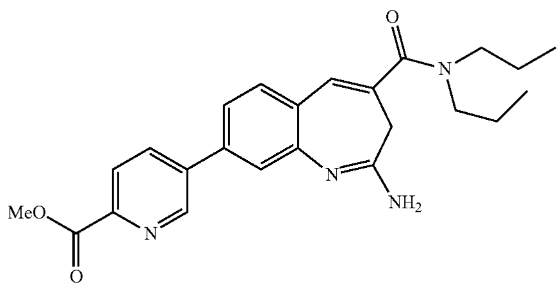 |
| 210 | 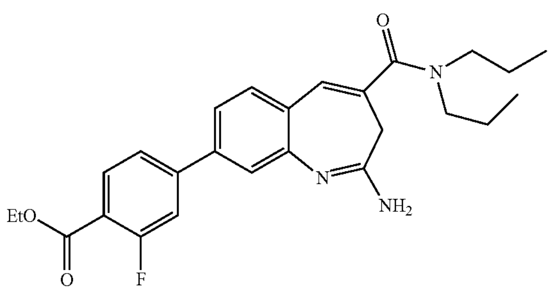 [SMILES: CCCN(CCC)C(=O)C1=Cc2ccc(-c3ccc(C(=O)OCC)c(F)c3)cc2N=C(N)C1] |
| 227 | 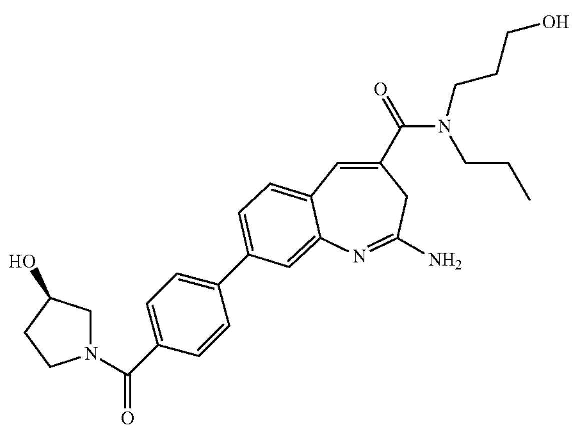 [SMILES: CCCN(CCCO)C(=O)C1=Cc2ccc(-c3ccc(C(=O)N4CC[C@@H](O)C4)cc3)cc2N=C(N)C1] |
| 228 | 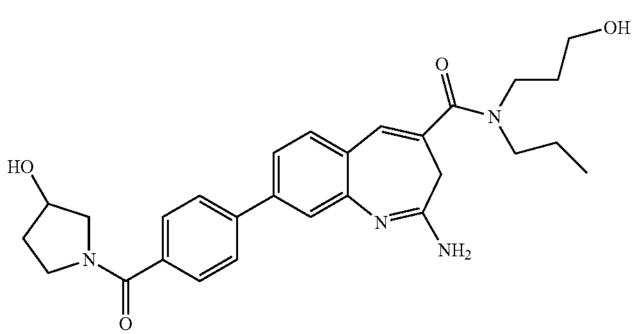 [SMILES: CCCN(CCCO)C(=O)C1=Cc2ccc(-c3ccc(C(=O)N4CCC(O)C4)cc3)cc2N=C(N)C1] |

TABLE 1-continued

| # | Chemical Structure |
|---|---|
| 229 | 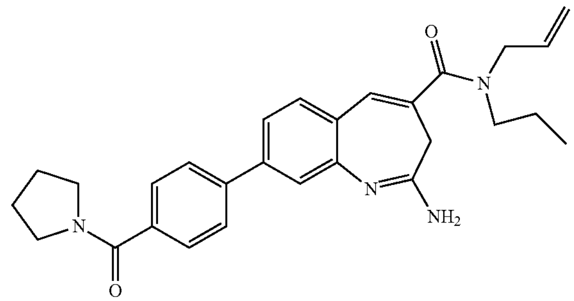 [SMILES: C=CCN(CCC)C(=O)C1=Cc2ccc(-c3ccc(C(=O)N4CCCC4)cc3)cc2N=C(N)C1] |
| 230 | 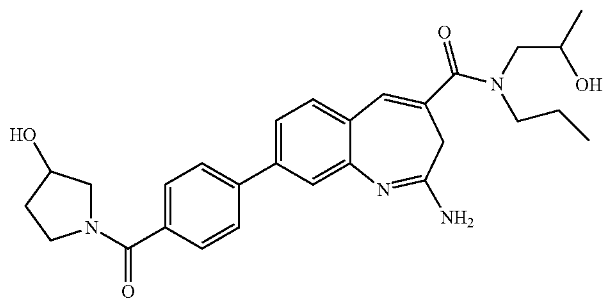 [SMILES: CCCN(CC(C)O)C(=O)C1=Cc2ccc(-c3ccc(C(=O)N4CCC(O)C4)cc3)cc2N=C(N)C1] |
| 231 | 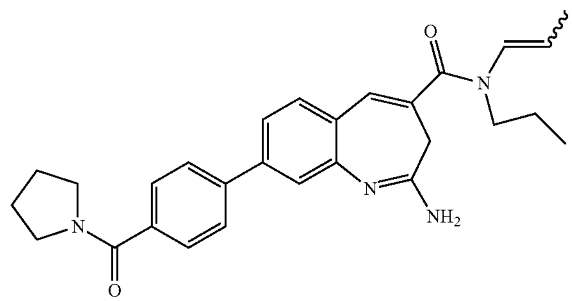 |
| 232 | 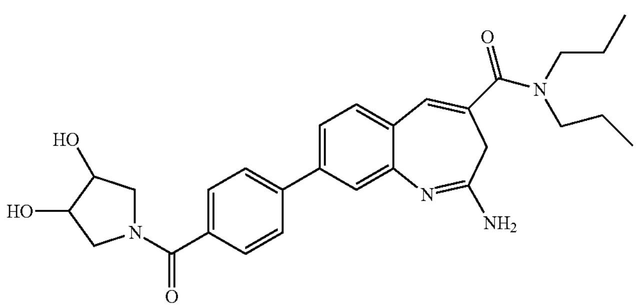 [SMILES: CCCN(CCC)C(=O)C1=Cc2ccc(-c3ccc(C(=O)N4CC(O)C(O)C4)cc3)cc2N=C(N)C1] |
| 233 | 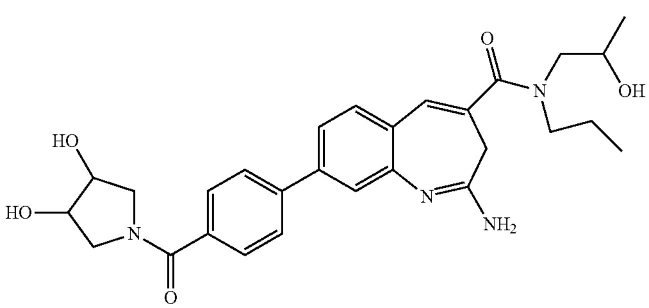 [SMILES: CCCN(CC(C)O)C(=O)C1=Cc2ccc(-c3ccc(C(=O)N4CC(O)C(O)C4)cc3)cc2N=C(N)C1] |

TABLE 1-continued

| # | Chemical Structure |
|---|---|
| 234 | 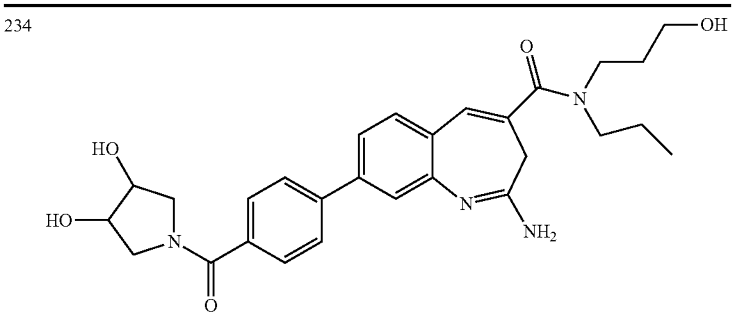 |
| 235 | 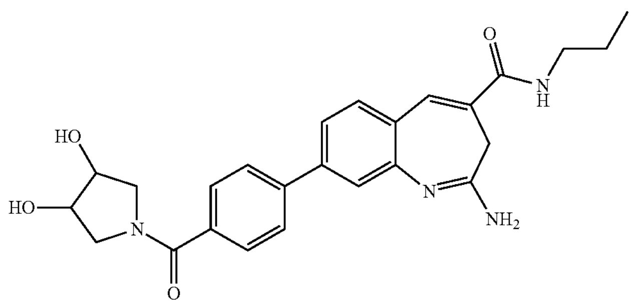 [SMILES: CCCNC(=O)C1=Cc2ccc(-c3ccc(C(=O)N4CC(O)C(O)C4)cc3)cc2N=C(N)C1] |
| 236 | 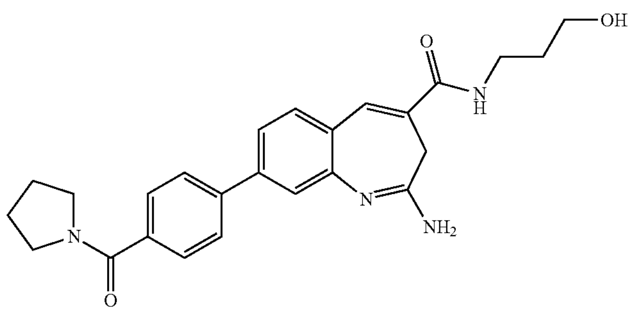 [SMILES: NC1=Nc2cc(-c3ccc(C(=O)N4CCCC4)cc3)ccc2C=C(C(=O)NCCCO)C1] |
| 237 | 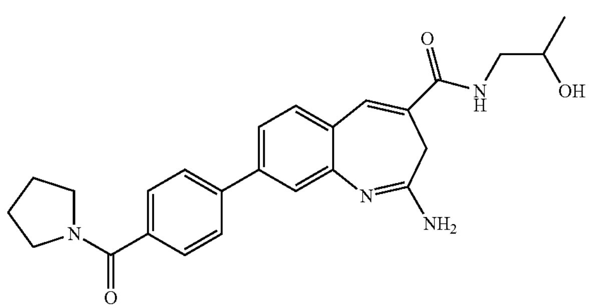 [SMILES: CC(O)CNC(=O)C1=Cc2ccc(-c3ccc(C(=O)N4CCCC4)cc3)cc2N=C(N)C1] |
| 238 | 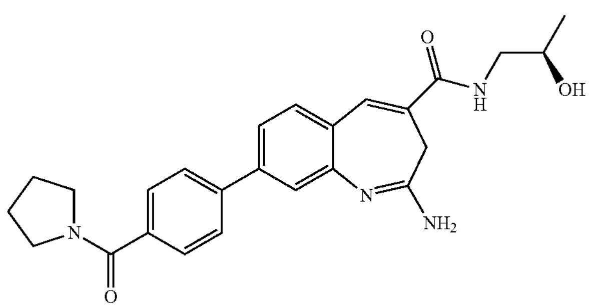 [SMILES: C[C@@H](O)CNC(=O)C1=Cc2ccc(-c3ccc(C(=O)N4CCCC4)cc3)cc2N=C(N)C1] |

TABLE 1-continued

| # | Chemical Structure |
|---|---|
| 239 | 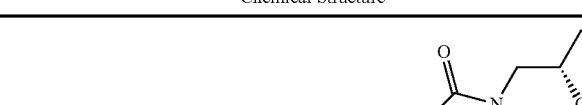 |

In one aspect, the invention includes a compound, or salt thereof, with an $MC_{50}$ value≦25,000 nM for TLR8. In another aspect, the invention includes a compound or salt thereof, with an $MC_{50}$ value≦10,000 nM for TLR8. In another aspect, the invention includes a compound or salt thereof, with an $MC_{50}$ value≦1,000 nM for TLR8. In another aspect, the invention includes a compound or salt thereof, with an $MC_{50}$ value≦100 nM for TLR8. In another aspect, the invention includes a compound or salt thereof, with an $MC_{50}$ value≦25 nM for TLR8.

In one aspect, the invention includes a compound or salt thereof, with an $MC_{50}$ value≦25,000 nM for TLR7. In another aspect, the invention includes a compound or salt thereof, with an $MC_{50}$ value≦10,000 nM for TLR7. In another aspect, the invention includes a compound or salt thereof, with an $MC_{50}$ value≦1,000 nM for TLR7. In another aspect, the invention includes a compound or salt thereof, with an $MC_{50}$ value≦100 nM for TLR7. In another aspect, the invention includes a compound or salt thereof, with an $MC_{50}$ value≦25 nM for TLR7.

In one aspect, the invention does not include a compound or salt thereof, with an $MC_{50}$>25,000 for TLR7. In one aspect, the invention does not include a compound or salt thereof, with an $MC_{50}$>25,000 for TLR8. In one aspect, the invention does not include a compound or salt thereof, with $MC_{50}$ values>25,000 for TLR7 and for TLR8.

Another aspect of the invention relates to soft drugs (also known as "antedrugs"). "Soft drugs" can be defined as biologically active chemical compounds (drugs) which are metabolically deactivated after they achieve their therapeutic role at their designed site of action. The use of soft drugs, instead of their non-deactivatable analogs, can avoid unwanted side effects. In one aspect, the metabolic disposition of the soft drugs takes place with a controllable rate in a predictable manner. One embodiment of the invention relates to compounds that are soft drugs. Specifically, the invention relates to compounds that are designed to cleave in vivo, after achieving their therapeutic effect, to a less active moiety. The invention relates to compounds that are designed to cleave in vivo, after achieving their therapeutic effect, to a non-toxic moiety. Soft drugs of the invention include compounds such as Compound 139, 220, 211, 187, 190, 203, 204, 206, 207, 208, 212, and 210.

The term "compound of the invention" refers to exemplified compounds and compounds covered under the formulae described herein.

The term "substituted," as used herein, means that any one or more hydrogen atoms on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring.

The term "alkyl" as used herein refers to a saturated linear or branched-chain monovalent hydrocarbon radical having one to twelve, including one to ten carbon atoms ($C_1$-$C_{10}$), one to six carbon atoms ($C_1$-$C_6$) and one to four carbon atoms ($C_1$-$C_4$), wherein the alkyl radical may be optionally substituted independently with one or more substituents described below. Examples of alkyl radicals include hydrocarbon moieties such as, but not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, and 1-octyl.

The term "alkenyl" refers to a linear or branched-chain monovalent hydrocarbon radical having two to 10 carbon atoms ($C_2$-$C_{10}$), including two to six carbon atoms ($C_2$-$C_6$) and two to four carbon atoms ($C_2$-$C_4$), and at least one double bond, and includes, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations. The term "alkenyl" includes allyl.

The term "alkynyl" refers to a linear or branched monovalent hydrocarbon radical of two to twelve carbon atoms ($C_2$-$C_{12}$), including two to 10 carbon atoms ($C_2$-$C_{10}$), two to six carbon atoms ($C_2$-$C_6$) and two to four carbon atoms ($C_2$-$C_4$), containing at least one triple bond. Examples include, but are not limited to, ethynyl, propynyl, butynyl, pentyn-2-yl and the like, wherein the alkynyl radical may be optionally substituted independently with one or more substituents described herein.

The terms "carbocycle," "carbocyclyl," or "cycloalkyl" are used interchangeably herein and refer to saturated or partially unsaturated cyclic hydrocarbon radical having from three to twelve carbon atoms ($C_3$-$C_{12}$), including from three to ten carbon atoms ($C_3$-$C_{10}$) and from three to six carbon atoms ($C_3$-$C_6$). The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. Bicyclic carbocycles have 7 to 12 ring atoms, e.g. arranged as a bicyclo [4,5], [5,5], [5,6] or [6,6] system, or 9 or 10 ring atoms arranged as a bicyclo[5,6] or [6,6] system, or as bridged systems such as bicyclo[2.2.1]heptane, bicyclo[2.2.2]octane, and bicyclo[3.2.2]nonane. The cycloalkyl may be optionally substituted independently at one or more substitutable positions with one or more substituents described herein. Such cycloalkyl groups may be optionally substituted with, for example, one or more groups independently selected from $C_1$-$C_6$ alkyl, $C_1$-$C_6$ alkoxy, halogen, hydroxy, cyano, nitro, amino, mono($C_1$ $C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl and di($C_1$ $C_6$)alkylamino($C_1$-$C_6$)alkyl.

The term "cycloalkenyl" refers to a partially unsaturated cyclic hydrocarbon radical having from three to ten carbon atoms ($C_3$-$C_{10}$), including from three to six carbon atoms ($C_3$-$C_6$) and having at least one double bond within the carbocycle.

The term "heteroalkyl" refers to saturated linear or branched-chain monovalent hydrocarbon radical of one to twelve carbon atoms ($C_1$-$C_{12}$), including from one to six carbon atoms ($C_1$-$C_6$) and from one to four carbon atoms ($C_1$-$C_4$), wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" and "heterocyclyl" are used interchangeably herein and refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. The term further includes fused ring systems which include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco [3.1.0]hexanyl, 3-azabicyclo[4.1.0]heptanyl, azabicyclo [2.2.2]hexanyl, 3H-indolyl quinolizinyl and N-pyridyl ureas. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_{66}$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl, etc.), which is optionally substituted with one or more substituents independently selected from, for example, halogen, lower alkyl, lower alkoxy, trifluoromethyl, aryl, heteroaryl and hydroxy. In one embodiment, the aryl is a 6-membered aryl. For example, aryl is phenyl.

The term "heteroaryl" refers to a monovalent aromatic radical of 5-, 6-, or 7-membered rings and includes fused ring systems (at least one of which is aromatic) of 5-10 atoms containing at least one and up to four heteroatoms selected from nitrogen, oxygen, and sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, isobenzofuran-1(3H)-one, and furopyridinyl. Spiro moieties are also included within the scope of this definition. Heteroaryl groups are optionally substituted with one or more substituents independently selected from, for example, halogen, lower alkyl, lower alkoxy, haloalkyl, aryl, heteroaryl, and hydroxy.

The term "halogen" represents fluorine, bromine, chlorine, and iodine.

The term "oxo" represents =O.

In general, the various moieties or functional groups of the compounds of the invention may be optionally substituted by one or more substituents. Examples of substituents suitable for purposes of this invention include, but are not limited to, oxo, halogen, cyano, nitro, trifluoromethyl, difluoromethoxy, trifluoromethoxy, azido, —NR"SO$_2$R', —SO$_2$NR'R", —C(O)R', —C(O)OR', —OC(O)R, —NR"C(O)OR', —NR"C(O)R', —C(O)NR'R", —NRC(O)NR", —NRC(NCN)NR'R", —OR', aryl, heteroaryl, arylalkyl, heteroarylalkyl, heterocyclyl, and heterocyclylalkyl, where R', R" and R'" are independently H, alkyl, heteroalkyl, cycloalkyl, heterocycloalkyl, alkenyl, alkynyl, aryl or heteroaryl.

An "(alkyl)aryl" group, as used herein, is an aryl substituent that is linked to a compound by a straight chain or branched alkyl group having from one to twelve carbon atoms. In one aspect, the aryl substituent is linked to a compound by a straight chain or branched alkyl group having 1-6 carbon atoms. The alkyl moiety of the (alkyl)aryl group is optionally substituted. In one embodiment, the aryl is a 6-membered aryl. For example, aryl is phenyl.

An "(alkyl)heterocycloalkyl" group, as used herein, is a heterocycle substituent that is linked to a compound by a straight chain or branched alkyl group having from one to twelve carbon atoms. In one aspect, the heterocycle substituent is linked to a compound by a straight chain or branched alkyl group having 1-6 carbon atoms. The alkyl moiety of the (alkyl)heterocycle group is optionally substituted.

An "(alkyl)cycloalkyl" group, as used herein, is a cycloalkyl substituent that is linked to a compound by a straight chain or branched alkyl group having from one to twelve carbon atoms. In one aspect, the cycloalkyl substituent is linked to a compound by a straight chain or branched alkyl group having 1-6 carbon atoms. The alkyl moiety of the (alkyl)cycloalkyl group is optionally substituted.

An "(alkyl)cycloalkenyl" group, as used herein, is a cycloalkenyl substituent that is linked to a compound by a straight chain or branched alkyl group having from one to twelve carbon atoms. In one aspect, the cycloalkenyl substituent is linked to a compound by a straight chain or branched alkyl group having 1-6 carbon atoms. The alkyl moiety of the (alkyl)cycloalkenyl group is optionally substituted.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the compounds of the formulae described herein.

Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. Enantiomers can also be separated by use of a chiral HPLC column. Methods for the determination of stereochemistry and the separation of stereoisomers are well known in the art (see discussion in Chapter 4 of "Advanced Organic Chemistry", 4th edition, J. March, John Wiley and Sons, New York, 1992).

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

A single stereoisomer, e.g. an enantiomer, substantially free of its stereoisomer may be obtained by resolution of the racemic mixture using a method such as formation of diastereomers using optically active resolving agents (Eliel, E. and Wilen, S. Stereochemistly of Organic Compounds, John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, a-methyl-13-phenyl-ethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, for example a menthyl ester such as (–) menthyl chloroformate, in the presence of base, or Mosher ester, a-methoxy-a-(trifluoromethyl)phenyl acetate (Jacob III, (1982) J. Org. Chem. 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (Chiral Liquid Chromatography (1989) W. J. Lough, Ed., Chapman and Hall, New York; Okamoto, (1990) J. of Chromatogr. 513:375-378). Enriched or purified enantiomers can be distinguished by methods used to distinguish other chiral molecules with asymmetric carbon atoms, such as optical rotation and circular dichroism.

"Tautomer" refers to a compound whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomer form.

The present invention is intended to include all isotopes of atoms occurring in the present compounds. Isotopes include those having the same atomic number but different mass numbers. By way of general example and without limitation, isotopes of hydrogen include tritium and deuterium, and isotopes of carbon include C-13 and C-14.

In addition to compounds of the invention, the invention also includes pharmaceutically acceptable salts of such compounds.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, pheylacetates, phenylpropionates, phenylbutyrates, citrates, lactates, y-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N¬methylglucosamine, plus salts formed with basic amino acids such as glycine, ornithine, histidine, phenylglycine, lysine and arginine.

The present invention also provides salts of compounds of the invention which are not necessarily pharmaceutically acceptable salts, but which may be useful as intermediates for preparing and/or purifying compounds of the invention and/ or for separating enantiomers of compounds of the invention.

The inventive compounds may be prepared using the reaction routes and synthesis schemes as described in Scheme I, employing the techniques available in the art using starting materials that are readily available.

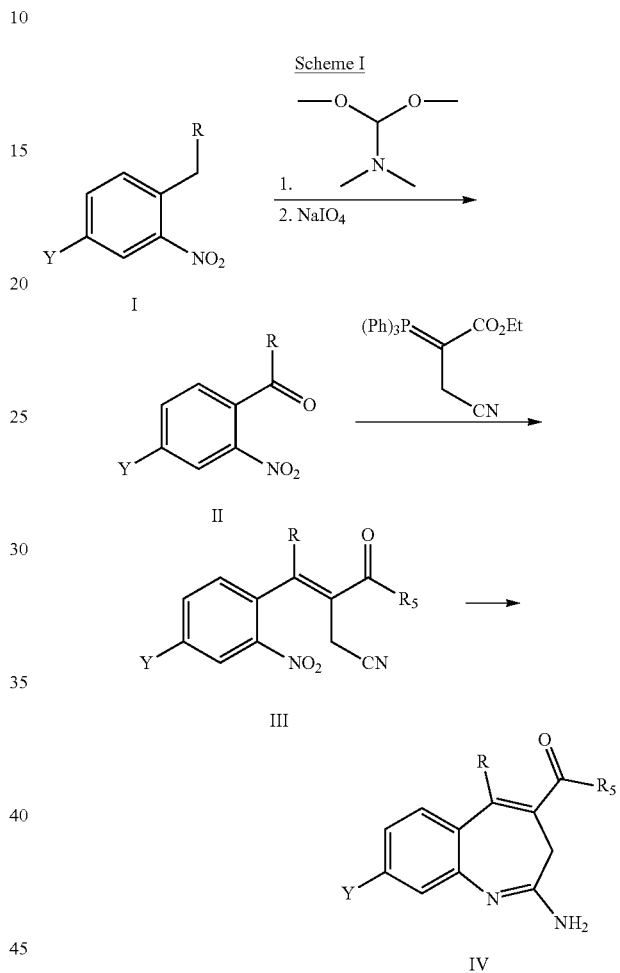

In Scheme I, compounds of Formula II may be prepared from an alkyl arene of Formula I by treatment with dimethylformamide dimethyl acetal with or without the use of pyrollidine (J. Org. Chem., (1986), 51(26), 5106-5110) in DMF at 70-90° C. The crude intermediate (not shown) may be cleaved to the aldehyde of Formula II with NaIO4 in THF/pH 7.2 phosphate buffer at or around room temperature. The aldehyde of Formula II may be olefinated with phosphonium ylid in toluene at temperatures ranging from 70 to 110° C. (1-16 hours) to give compounds of Formula III. Compounds of Formula IV can be prepared from a compound of Formula III using iron powder in acetic acid. The reaction may be conducted at temperatures of about 90° C. for about 3-14 hours.

It is noted that some of the preparations of compounds of the invention described herein may require protection of remote functionalities. The need for such protection will vary depending on the nature of the functionality and the conditions used in the preparation methods and can be readily determined by those skilled in the art. Such protection/deprotection methods are well known to those skilled in the art.

The compounds of the invention find use in a variety of applications. For example, in certain aspects the invention provides methods for modulating TLR7- and/or TLR8-mediated signaling. The methods of the invention are useful, for example, when it is desirable to alter TLR7- and/or TLR8-mediated signaling in response to a suitable TLR7 and/or TLR8 ligand or a TLR7 and/or TLR8 signaling agonist.

As used herein, the terms "TLR7 and/or TLR8 ligand," "ligand for TLR7 and/or TLR8," and "TLR7 and/or TLR8 signaling agonist" refer to a molecule, other than a compound of the invention, that interacts directly or indirectly with TLR7 and/or TLR8 and induces TLR7- and/or TLR8-mediated signaling. In certain embodiments, a TLR7 and/or TLR8 ligand is a natural ligand, i.e., a TLR7 and/or TLR8 ligand that is found in nature. In certain embodiments, a TLR7 and/or TLR8 ligand refers to a molecule other than a natural ligand of TLR7 and/or TLR8, e.g., a molecule prepared by human activity.

The term "modulate" as used herein with respect to the TLR7 and/or TLR8 receptors means the mediation of a pharmacodynamic response in a subject by (i) inhibiting or activating the receptor, or (ii) directly or indirectly affecting the normal regulation of the receptor activity. Compounds that modulate the receptor activity include agonists, antagonists, mixed agonists/antagonists and compounds that directly or indirectly affect regulation of the receptor activity.

The term "agonist" refers to a compound that, in combination with a receptor (e.g., a TLR), can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular TLR (e.g., a TLR7 and/or TLR8 agonist). The term "partial agonist" refers to a compound that produces a partial but not a full cellular response. TLR7 and TLR8-related assays are known in the art (e.g., Gorden et al., *Journal of Immunology* 177, pp. 8164-8170 (2006) and Zhu et al., *Molecular Immunology*, vol. 45 (11), pp. 3238-3242 (2008)).

The term "antagonist" as used herein refers to a compound that competes with an agonist or partial agonist for binding to a receptor, thereby blocking the action of an agonist or partial agonist on the receptor. More specifically, an antagonist is a compound that inhibits the activity of TRL7 or TLR8 at the TLR7 or TLR8 receptor, respectively. "Inhibit" refers to any measurable reduction of biological activity. Thus, as used herein, "inhibit" or "inhibition" may be referred to as a percentage of a normal level of activity.

In one aspect of this invention, a method of treating or preventing a condition or disorder treatable by modulation of TLR7- and/or TLR8-mediated cellular activities in a subject comprises administering to said subject a composition comprising a compound of the invention in an amount effective to treat or prevent the condition or disorder. The term "TLR7- and/or TLR8-mediated" refers to a biological or biochemical activity that results from TLR7- and/or TLR8 function.

Conditions and disorders that can be treated by the methods of this invention include, but are not limited to, cancer, immune complex-associated diseases, autoimmune diseases or disorders, inflammatory disorders, immunodeficiency, graft rejection, graft-versus-host disease, allergies, cardiovascular disease, fibrotic disease, asthma, infection, and sepsis.

More specifically, methods useful in the treatment of conditions involving cancer (therapeutic or cancer vaccine), allergic disease (e.g., atopic dermititis, allergic rhinitis, asthma), infectious disease (prophylaxis with vaccine and anti-viral), and immunodeficiency will employ compounds of the invention that inhibit TLR7- and/or TLR8-mediated signaling.

Alternatively, methods useful in the treatment of conditions involving autoimmune disease, CF, sepsis, graft rejection, and GVHD generally will employ compounds of the invention that augment TLR7- and/or TLR8-mediated signaling.

In some instances the compositions can be used to inhibit or promote TLR7- and/or TLR8-mediated signaling in response to a TLR7 and/or TLR8 ligand or signaling agonist. In other instances the compositions can be used to inhibit or promote TLR7- and/or TLR8-mediated immunostimulation in a subject.

The term "treating" as used herein, unless otherwise indicated, means at least the mitigation of a disease or condition and includes, but is not limited to, modulating and/or inhibiting an existing disease or condition, and/or alleviating the disease or condition to which such term applies, or one or more symptoms of such disease or condition. The term "treatment," as used herein, unless otherwise indicated, refers to the act of treating as "treating" is defined immediately above. Therapeutic treatment refers to treatment initiated after observation of symptoms and/or a suspected exposure to a causative agent of the disease or condition. Generally, therapeutic treatment may reduce the severity and/or duration of symptoms associated with the disease or condition.

As used herein, "preventing" means causing the clinical symptoms of a disease or condition not to develop i.e., inhibiting the onset of a disease or condition in a subject that may be exposed to or predisposed to the disease or condition, but does not yet experience or display symptoms of the disease or condition. Prophylactic treatment means that a compound of the invention is administered to a subject prior to observation of symptoms and/or a suspected exposure to a causative agent of the condition (e.g., a pathogen or carcinogen). Generally, prophylactic treatment may reduce (a) the likelihood that a subject that receives the treatment develops the condition and/or (b) the duration and/or severity of symptoms in the event the subject develops the condition.

As used herein, the terms "autoimmune disease," "autoimmune disorder" and "autoimmunity" refer to immunologically mediated acute or chronic injury to a tissue or organ derived from the host. The terms encompass both cellular and antibody-mediated autoimmune phenomena, as well as organ-specific and organ-nonspecific autoimmunity. Autoimmune diseases include insulin-dependent diabetes mellitus, rheumatoid arthritis, systemic lupus erythematosus, multiple sclerosis, atherosclerosis, and inflammatory bowel disease. Autoimmune diseases also include, without limitation, ankylosing spondylitis, autoimmune hemolytic anemia, Bechet's syndrome, Goodpasture's syndrome, Graves' disease, Guillain Barre syndrome, Hashimoto's thyroiditis, idiopathic thrombocytopenia, myasthenia gravis, pernicious anemia, polyarteritis nodosa, polymyositis/dermatomyositis, primary biliary sclerosis, psoriasis, sarcoidosis, sclerosing cholangitis, Sjogren's syndrome, systemic sclerosis (scleroderma and CREST syndrome), Takayasu's arteritis, temporal arteritis, and Wegener's granulomatosis. Autoimmune diseases also include certain immune complex-associated diseases.

As used here in, the term "fibrotic disease" refers to diseases or disorders involving excessive and persistent formation of scar tissue associated with organ failure in a variety of chronic diseases affecting the lungs, kidneys, eyes, heart, liver, and skin. Although tissue remodeling and scarring is part of the normal wound healing process, repeated injury or insult can lead to persistent and excessive scarring and, ultimately, organ failure.

Fibrotic conditions include diffuse fibrotic lung disease, chronic kidney disease, including diabetic kidney disease; liver fibrosis (e.g., chronic liver disease (CLD) caused by continuous and repeated insults to the liver from causes such as are viral hepatitis B and C, alcoholic cirrhosis or non-alcoholic fatty liver disease (NAFLD), or primary sclerosing cholangitis (PSC), a rare disease characterized by fibrosing inflammatory destruction of the bile ducts inside and outside the liver, leading to bile stasis, liver fibrosis, and ultimately to cirrhosis, and end-stage liver disease); lung fibrosis (e.g., idiopathic pulmonary fibrosis (IPF)); and systemic sclerosis (a degenerative disorder in which excessive fibrosis occurs in multiple organ systems, including the skin, blood vessels, heart, lungs, and kidneys).

Other examples include cystic fibrosis of the pancreas and lungs; injection fibrosis, which can occur as a complication of intramuscular injections, especially in children; endomyocardial fibrosis; mediastinal fibrosis, myelofibrosis; retroperitoneal fibrosis; progressive massive fibrosis, a complication of coal workers' pneumoconiosis; nephrogenic systemic fibrosis; and complication of certain types of surgical implants (e.g. occurrence in attempts at creating an artificial pancreas for the treatment of diabetes mellitus.

As used herein, the term "cardiovascular disease" refers to diseases or disorders of the cardiovascular system involving an inflammatory component, and/or the accumulation of plaque, including without limitation coronary artery disease, cerebrovascular disease, peripheral arterial disease, atherosclerosis, and arteriosclerosis.

As used herein, the terms "cancer" and, "tumor" refer to a condition in which abnormally replicating cells of host origin are present in a detectable amount in a subject. The cancer can be a malignant or non-malignant cancer. Cancers or tumors include, but are not limited to, biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

As used herein, the terms "inflammatory disease" and inflammatory disorder" refer to a condition characterized by inflammation e.g., a localized protective reaction of tissue to irritation, injury, or infection, characterized by pain, redness, swelling, and sometimes loss of function. Inflammatory diseases or disorders include e.g., allergy, asthma, and allergic rash.

As used herein, the term "immune complex-associated disease" refers to any disease characterized by the production and/or tissue deposition of immune complexes (i.e., any conjugate including an antibody and an antigen specifically bound by the antibody), including, but not limited to systemic lupus erythematosus (SLE) and related connective tissue diseases, rheumatoid arthritis, hepatitis C- and hepatitis B-related immune complex disease (e.g., cryoglobulinemia), Bechet's syndrome, autoimmune glomerulonephritides, and vasculopathy associated with the presence of LDL/anti-LDL immune complexes.

As used herein, "immunodeficiency" refers to a disease or disorder in which the subject's immune system is not functioning in normal capacity or in which it would be useful to boost a subject's immune response, for example to eliminate a tumor or cancer (e.g., tumors of the brain, lung (e.g., small cell and non-small cell), ovary, breast, prostate, colon, as well as other carcinomas and sarcomas) or an infection in a subject. The immunodeficiency can be acquired or it can be congenital.

As used herein, "graft rejection" refers to immunologically mediated hyperacute, acute, or chronic injury to a tissue or organ derived from a source other than the host. The term thus encompasses both cellular and antibody-mediated rejection, as well as rejection of both allografts and xenografts.

"Graft-versus-host disease" (GvHD) is a reaction of donated bone marrow against a patient's own tissue. GVHD is seen most often in cases where the blood marrow donor is unrelated to the patient or when the donor is related to the patient but not a perfect match. There are two forms of GVHD: an early form called acute GVHD that occurs soon after the transplant when the white cells are on the rise and a late form called chronic GVHD.

$T_{H2}$-mediated, atopic diseases include, but are not limited to, atopic dermatitis or eczema, eosinophilia, asthma, allergy, allergic rhinitis, and Ommen's syndrome.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions As used herein, "asthma" refers to a disorder of the respiratory system characterized by inflammation, narrowing of the airways and increased reactivity of the airways to inhaled agents. Asthma is frequently, although not exclusively associated with atopic or allergic symptoms. For example, asthma can be precipitated by exposure to an allergen, exposure to cold air, respiratory infection, and exertion.

As used herein, the terms "infection" and, equivalently, "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

As used herein, the term "sepsis" refers to the presence of bacteria (bacteremia) or other infectious organisms or their toxins in the blood (septicemia) or in other tissue of the body.

Further provided is a compound of the invention, or a salt thereof, for use as a medicament in the treatment of the diseases or conditions described above in a mammal, for example, a human, suffering from such disease or condition. Also provided is the use of a compound of the invention, or a salt thereof, in the preparation of a medicament for the treatment of the diseases and conditions described above in a mammal, for example a human, suffering from such disorder.

This invention also encompasses pharmaceutical compositions containing a compound of the invention and methods of treating or preventing conditions and disorders by modulation of TLR7- and/or TLR8-mediated cellular activities by administering a pharmaceutical composition comprising a compound of the invention, or a salt thereof, to a patient in need thereof.

In order to use a compound of the invention or a salt thereof for the therapeutic treatment (including prophylactic treatment) of mammals including humans, it is normally formulated in accordance with standard pharmaceutical practice as a pharmaceutical composition.

According to this aspect of the invention there is provided a pharmaceutical composition that comprises a compound of the invention, or a salt thereof, as defined hereinbefore in association with a pharmaceutically acceptable diluent or carrier.

To prepare the pharmaceutical compositions according to this invention, a therapeutically or prophylactically effective amount of a compound of the invention or a salt thereof (alone or together with an additional therapeutic agent as disclosed herein) is intimately admixed, for example, with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of the invention, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. For parenteral formulations, the carrier will usually comprise sterile water, aqueous sodium chloride solution, 1,3-butanediol, or any other suitable non toxic parenterally acceptable diluent or solvent. Other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 micron or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for transdermal administration may be in the form of those transdermal skin patches that are well known to those of ordinary skill in the art. Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736, 152, and (b) diffusional systems in which an active component permeates at a controlled rate from a polymer such as described in U.S. Pat. Nos. 3,854,480, 5,133,974 and 5,407, 686. In addition, pump-based hardware delivery systems can be used, some of which are adapted for implantation.

Compositions may be administered in the form of a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's Pharmaceutical Sciences, Ed. By Arthur Osol, p. 1445 (1980)). Of course, the ordinary artisan can readily determine a suitable saline content and pH for an innocuous aqueous carrier for nasal administration.

Other, non-limiting examples of intranasal dosage forms containing the composition include nasal gels, creams, pastes or ointments with a viscosity of, e.g., from about 10 to about 3000 cps, or from about 2500 to 6500 cps, or greater, which may provide a more sustained contact with the nasal mucosal surfaces. Such carrier viscous formulations may be based upon, simply by way of example, polymeric carriers such as alkylcelluloses and/or other biocompatible carriers of high viscosity well known to the art (see e.g., Remington's, cited supra). The carrier containing the composition may also be soaked into a fabric material, such as gauze, that can be applied to the nasal mucosal surfaces to allow for active substances in the isolated fraction to penetrate to the mucosa.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation.

Further, for nasal administration of solutions or suspensions of the composition, various devices are available in the art for the generation of drops, droplets and sprays. For example, solutions comprising the isolated fraction can be administered into the nasal passages by means of a simple dropper (or pipet) that includes a glass, plastic or metal dispensing tube from which the contents are expelled drop by drop by means of air pressure provided by a manually powered pump, e.g., a flexible rubber bulb, attached to one end. Fine droplets and sprays can be provided by a manual or electrically powered intranasal pump dispenser or squeeze bottle as well known to the art, e.g., that is designed to blow a mixture of air and fine droplets into the nasal passages.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, for example, about 0.05 to about 35 mg/kg/day, in single or divided doses. For example a dosage is about 0.0005 to about 2.5 g/day. For example, a dosage is about 0.0005 to about 1 g/day in single or divided dosages. In some instances, dosage levels below the lower limit of the aforesaid range may be more than adequate, while in other cases still larger doses may be employed without causing any harmful side effect, provided that such larger doses are first divided into several small doses for administration throughout the day.

For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of the invention will naturally vary according to the nature and severity of the conditions, the age and sex of the animal or patient and the route of administration, according to well known principles of medicine. It will be understood that the specific dosage level and frequency of dosage for any particular subject may be varied and will depend upon a variety of factors including the activity of the specific compound of the invention, the species, age, body weight, general health, sex and diet of the subject, the mode and time of administration, rate of excretion, drug combination, and severity of the particular condition, but can nevertheless be routinely determined by one skilled in the art.

A compound of the invention or salt thereof, is in some aspects administered to a subject in combination (e.g., in the same formulation or in separate formulations) with another therapeutic agent ("combination therapy"). The compound of the invention is administered in admixture with another therapeutic agent or is administered in a separate formulation. When administered in separate formulations, a compound of the invention and another therapeutic agent is administered substantially simultaneously or sequentially. In one aspect, a compound of the invention is administered to a subject in combination with another therapeutic agent for treating a condition or disease. In one aspect, a compound of the invention is administered to a subject in combination with another therapeutic agent for preventing a condition or disease. In one aspect, a compound of the invention is administered to a subject in combination with a vaccine for preventing a condition or disease. In one aspect, a compound of the invention is administered to a subject in combination with an infectious disease vaccine. In one aspect, a compound of the invention is administered to a subject in combination with a cancer vaccine.

A compound of the invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

A compound of the invention may also be helpful in individuals having compromised immune function. For example, a compound of the invention may be used for treating or preventing the opportunistic infections and tumors that occur after suppression of cell mediated immunity in, for example, transplant patients, cancer patients and HIV patients.

Such combination treatment may involve, in addition to a compound of the invention, conventional surgery or radiotherapy or chemotherapy. Such chemotherapy may include one or more of the following categories of anti-tumor agents: (i) antiproliferative/anti-neoplastic drugs and combinations thereof; (ii) cytostatic agents; (iii) agents which inhibit cancer cell invasion; (iv) inhibitors of growth factor function; (v) antiangiogenic agents; (vi) vascular damaging agents; (vii) antisense therapies; (viii) gene therapy approaches; (ix) interferon; and (x) immunotherapy approaches.

Therapeutic agents for treating or preventing respiratory diseases which may be administered in combination with a compound of the invention in a subject method include, but are not limited to beta adrenergics which include bronchodilators including albuterol, isoproterenol sulfate, metaproterenol sulfate, terbutaline sulfate, pirbuterol acetate and sahneterol formotorol; steroids including beclomethasone dipropionate, flunisolide, fluticasone, budesonide and triamcinolone acetonide. Anti-inflammatory drugs used in connection with the treatment or preventing of respiratory diseases include steroids such as beclomethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. Anti-histamines include, but are not limited to, diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine. Particular anti-histamines include rhinolast (Astelin®), claratyne (Claritin®), claratyne D (Claritin D®), telfast (Allegra®), Zyrtec®, and beconase.

In some embodiments, a compound of the invention is administered as a combination therapy with interferon-gamma (IFN-gamma), a corticosteroid such as prednisone, prednisolone, methyl prednisolone, hydrocortisone, cortisone, dexamethasone, betamethasone, etc., or a combination thereof, for the treatment or preventing of interstitial lung disease, e.g., idiopathic pulmonary fibrosis.

In some embodiments, a compound of the invention is administered in combination therapy with a known therapeutic agent used in the treatment of cystic fibrosis ("CF"). Therapeutic agents used in the treatment of CF include, but are not limited to, antibiotics; anti-inflammatory agents; DNAse (e.g., recombinant human DNAse; pulmozyme; dornase alfa); mucolytic agents (e.g., N-acetylcysteine; Mucomyst™; Mucosil™); decongestants; bronchodilators (e.g., theophylline; ipratropium bromide); and the like.

In some embodiments, a compound of the invention is administered prophylatically for the prevention of cardiovascular disease, e.g., atherosclerosis.

In another embodiment of the invention, an article of manufacture, or "kit", containing materials useful for the treatment or prevention of the diseases described above is provided.

In one embodiment, the kit comprises a container comprising a composition of the invention, or pharmaceutically acceptable salt thereof. In one embodiment, the invention provides a kit for treating or preventing a TLR7- and/or TLR8-mediated disorder. In another embodiment, the invention provides a kit for a condition or disorder treatable by selective modulation of the immune system in a subject. The kit may further comprise a label or package insert on or associated with the container. Suitable containers include, for example, bottles, vials, syringes, blister pack, etc. The container may be formed from a variety of materials such as glass or plastic. The container holds a compound of the invention or a pharmaceutical formulation thereof in an amount effective for treating or preventing the condition, and may have a sterile access port (for example, the container may be an intravenous solution bag or a vial having a stopper pierceable by a hypodermic injection needle). The label or package insert indicates that the composition is used for treating or preventing the condition of choice. In one embodiment, the label or package inserts indicates that the composition comprising a compound of the invention can be used, for example, to treat or prevent a disorder treatable by modulation of TLR7- and/or TLR8-mediated cellular activities. The label or package insert may also indicate that the composition can be used to treat or prevent other disorders. Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of the invention and, if present, the second pharmaceutical formulation. For example, if the kit comprises a first composition comprising a compound of the invention and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of the invention, such as tablets or capsules. Such a kit includes, for example, a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, the kit may comprise (a) a first container with a compound of the invention contained therein; and optionally (b) a second container with a second pharmaceutical formulation contained therein, wherein the second pharmaceutical formulation comprises a second compound which may be effective in treating or preventing a condition or disorder by selective modulation of TLR7- and/or TLR8-mediated cellular activities. Alternatively, or additionally, the kit may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a pharmaceutical formulation of a compound of the invention and a second formulation comprising a second therapeutic agent, the kit may comprise a container for containing the separate formulations, such as a divided bottle or a divided foil packet; however, the separate compositions may also be contained within a single, undivided container. Typically, the kit comprises directions for the administration of the separate components. The kit form is particularly advantageous when the separate components are administered in different dosage forms (e.g., oral and parenteral), are administered at different dosage intervals, or when titration of the individual components of the combination is desired by the prescribing physician.

Activity of the compounds can be assessed according to procedures described in, e.g., Gorden et al., *Journal of Immunology* 177, pp. 8164-8170 (2006) and Zhu et al., *Molecular Immunology*, vol. 45 (11), pp. 3238-3242 (2008).

$MC_{50}$ values for TLR8 activity are, for example, as shown below:

| Compound | Structure | TLR8 ($MC_{50}$) |
|---|---|---|
| 143 | 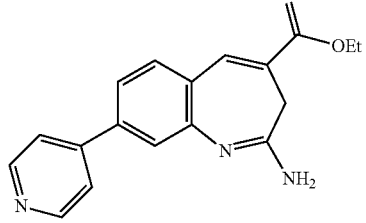 | 45 nM |
| 154 | 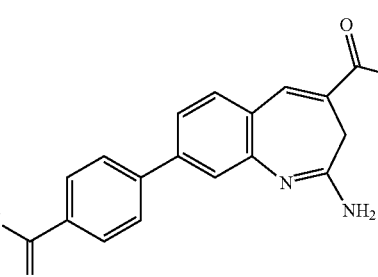 | 116 nM |
| 106 | 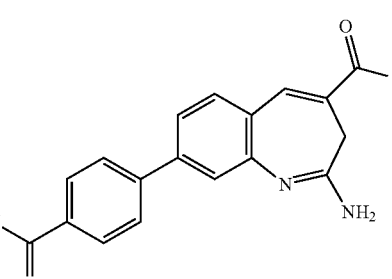 | 10 nM |

*stereo chem. arbitrary

| Compound | Structure | TLR8 (MC$_{50}$) |
|---|---|---|
| 127 | 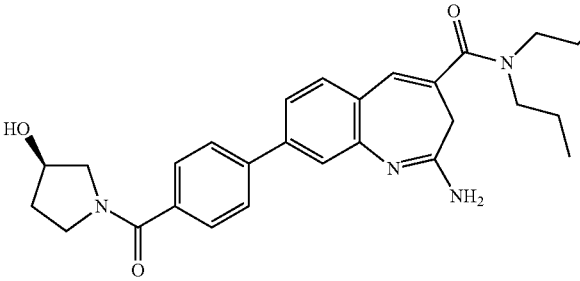 | 4 nM |
| 124 | 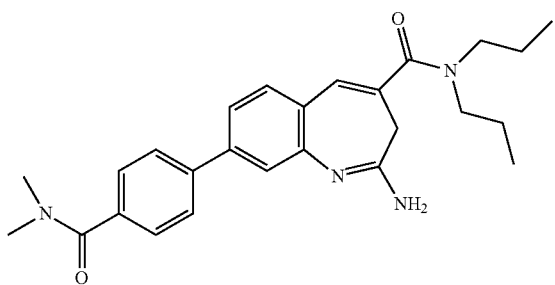 [SMILES: CCCN(CCC)C(=O)C1=Cc2ccc(-c3ccc(C(=O)N(C)C)cc3)cc2N=C(N)C1] | 104 nM |
| 190 | 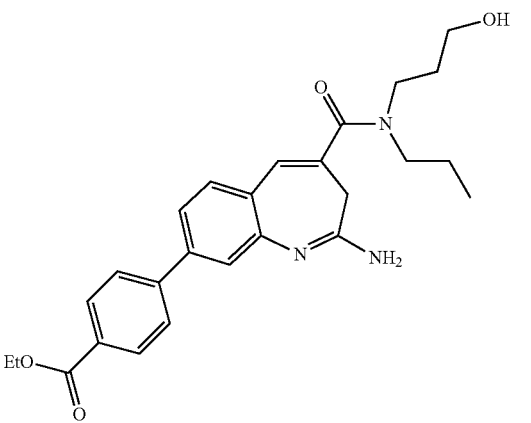 [SMILES: CCCN(CCCO)C(=O)C1=Cc2ccc(-c3ccc(C(=O)OCC)cc3)cc2N=C(N)C1] | 196 nM |
MC$_{50}$ values for TLR7 activity are, for example, as shown below:
| Compound | Structure | TLR7 (MC$_{50}$) |
|---|---|---|
| 178 | 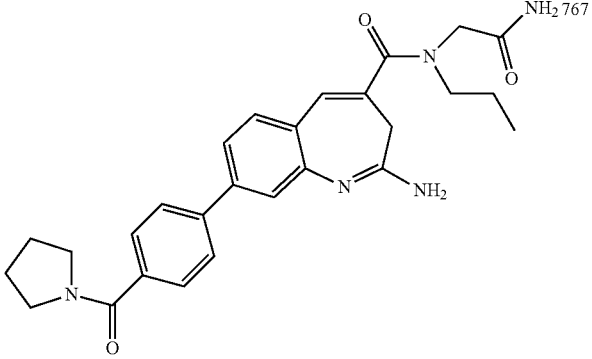 | 767 nM |

-continued

| Compound | Structure | TLR7 (MC$_{50}$) |
|---|---|---|
| 135 | 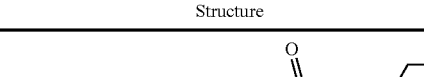 | 744 nM |

EXAMPLES

In order to illustrate the invention, the following examples are included. However, it is to be understood that these examples do not limit the invention and are only meant to suggest a method of practicing the invention. Persons skilled in the art will recognize that chemical reactions described may be readily adapted to prepare a number of other compounds of the invention, and alternative methods for preparing the compounds of this invention are also deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, Acros, TCI, Alfa Aesar or Maybridge, and were used without further purification unless otherwise indicated.

In the examples described below, the term "Example ###" refers to "Compound ###". For example, Example 101 is directed to Compound 101 and/or synthetic procedures relating to Compound 113.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heated dried.

Microwave reactions were performed on the Biotage Initiator system.

Column chromatography was done on a Biotage system or Isolute Flash Si SPE column (manufacturer: Biotage AB) having a silica gel column or on a silica SepPak cartridge (Waters). $^1$H and $^{19}$F NMR spectra were recorded on a Varian instrument operating at 400 MHz and 376 MHz, respectively. $^1$H-NMR spectra were obtained as CDCl$_3$ or d$_6$-DMSO solutions (reported in ppm), using chloroform (7.26 ppm) or tetramethylsilane (0 ppm) as the reference standards. When peak multiplicities are reported, the following abbreviations are used: s (singlet), d (doublet), t (triplet), q (quartet), br (broadened), dd (doublet of doublets), dt (double of triplets), m (multiplet).

Example 1

Synthetic Procedures

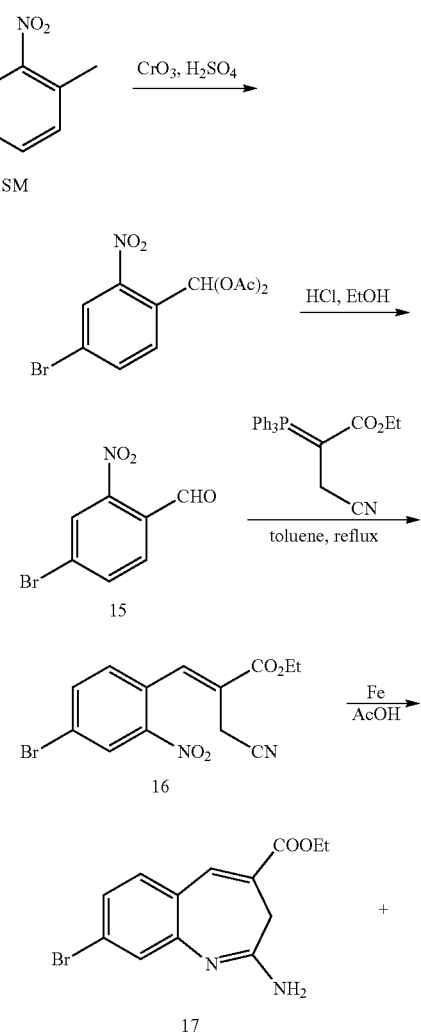

-continued

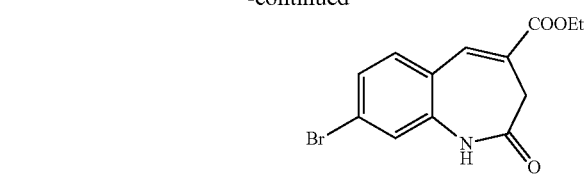

17B

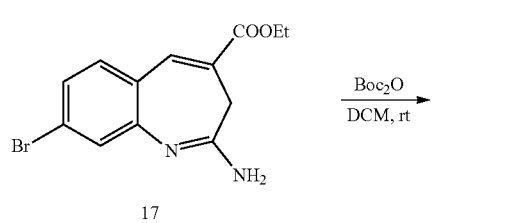

17

Boc₂O
―――→
DCM, rt

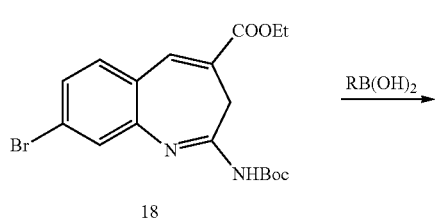

18

RB(OH)₂
―――→

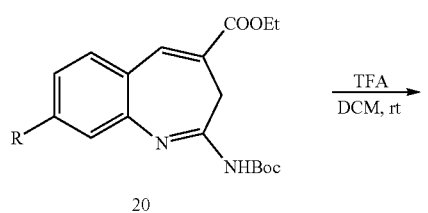

20

TFA
―――→
DCM, rt

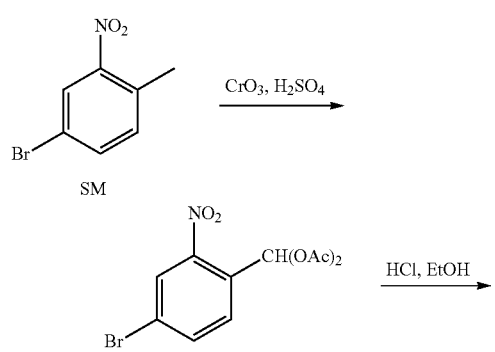

22

1. Synthesis of Compound 15

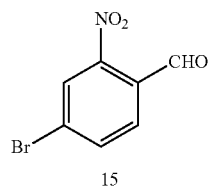

15

In a three-necked flask provided with a mechanical stirrer, dropping funnel, and thermometer, surrounded by an ice-salt bath, are placed 400 mL of acetic anhydride and 50 g (0.23 mole) of 4-bromo-1-methyl-2-nitrobenzene. To this solution is added slowly with stirring 54 mL of concentrated sulfuric acid. When the mixture has cooled to 0° C., a solution of 64 g of chromium trioxide in 360 mL of acetic anhydride is added slowly with stirring; at such a rate that the temperature does not exceed 10 and stirring is continued for 2 hours at 5-10° C. in an ice-water bath after the addition is complete. The contents of the flask are poured into the mixture of ice and water. The solid was filtered and washed with water until the washings are colorless. The product is suspended in 300 mL of 2% aqueous sodium carbonate solution and stirred. After thorough mixing, the solid was filtered and washed with water and dried.

A suspension of the diacetate in a mixture of 272 mL of concentrated hydrochloric acid, 250 mL of water, and 80 mL of ethanol was stirred and refluxed for 45 minutes. The mixture was then cooled to RT and the solid was filtered and washed with water. The crude product is purified by column (22 g, 42%).

2. Synthesis of Compound 16

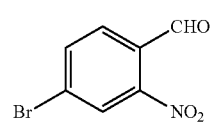

15

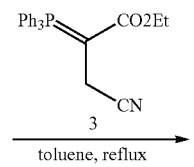

3
―――→
toluene, reflux

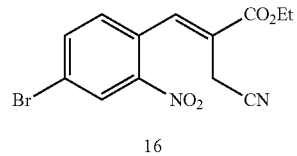

16

A mixture of the aldehyde (0.73 g, 3.17 mmol) and the ylide (1.42 g, 3.65 mmol) in toluene (8 mL) was gently refluxed for 2.5 hrs. The reaction mixture was cooled to room temperature and concentrated under reduced pressure to give the crude material that was used directly without further purification.

3. Synthesis of Compounds 17 and 17B

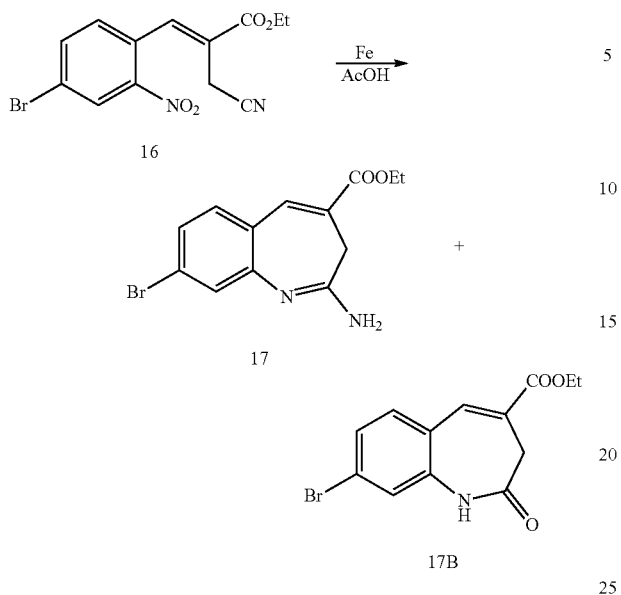

To a solution of the crude nitrile in AcOH (25 ml) was added iron (1.15 g, 20.61 mmol) at a room temperature. The resulting mixture was heated at 85° C. for 4 h. The reaction mixture was cooled to room temperature and diluted with $CH_2Cl_2$ (8 mL). The resulting mixture was filtered, the solids were washed with $CH_2Cl_2$. The filtrate was concentrated under reduced pressure to give viscous oil. To the crude material was added $CH_2Cl_2$ (8 mL). aq. $Na_2CO_3$ followed by water was slowly added with stirring until its pH=9-10. The mixture was filtered off and washed with $CH_2Cl_2$. The organic layer was separated. The aqueous layer was extracted with $CH_2Cl_2$. The organic layer was separated. The aqueous layer was extracted with $CH_2Cl_2$. The combined organic layers were washed with brine, dried over $Na_2SO_4$, the mixture was concentrated under reduced pressure to give the crude material that was purified by silica gel flash column chromatography to afford 0.329 g (33% for two steps) of the desired product was obtained based on $^1$H-NMR.

4. Synthesis of Compound 18

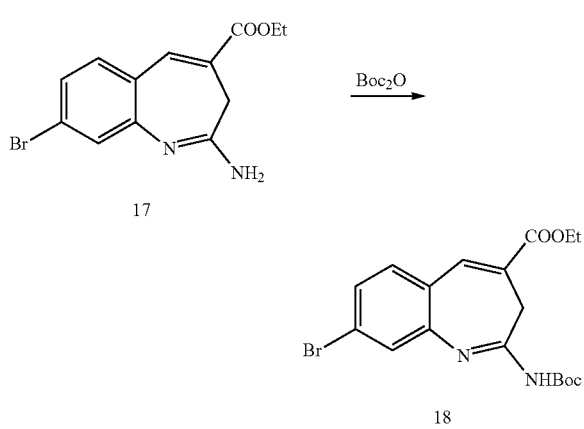

To the benzazepine (2.34 g, 7.57 mmol) in DCM (25 mL) was added $Boc_2O$ (2.06 g, 9.46 mmol) at room temperature. The reaction mixture was stirred for 20 hrs. The resulting mixture was consecutively washed with saturated aq. $NaHCO_3$ and brine. The organic layer was separated and dried over $Na_2SO_4$, filtered, and concentrated under reduced pressure to give the crude product that was purified by silica gel flash column chromatography (10% EtOAc in hexanes) to afford 1.64 g (52.9%) of the desired product.

5. Synthesis of Species

Example 101

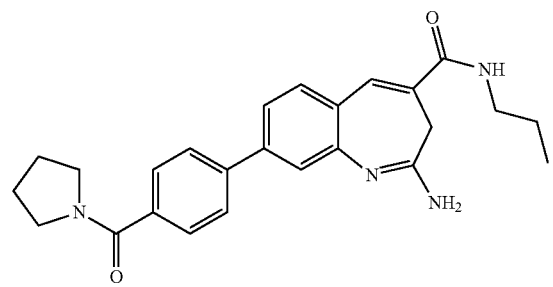 [SMILES: CCCNC(=O)C1=Cc2ccc(-c3ccc(C(=O)N4CCCC4)cc3)cc2N=C(N)C1]

(1E,4E)-2-amino-N-propyl-8-(4-(pyrrolidine-1-carbonyl)phenyl)-3H-benzo[b]azepine-4-carboxamide Step A: Preparation of (E)-1-(4-bromo-2-nitrostyryl)pyrrolidine A solution of 4-bromo-2-nitrotoluene (100 g, 463 mmol), pyrrolidine (46.2 mL, 565 mmol), and N,N-dimethylformamide dimethylacetal (75.6 mL, 565 mmol) was refluxed for 4 hours at 110° C. The reaction mixture was cooled to room temperature and concentrated under reduced pressure to give the crude (E)-1-(4-bromo-2-nitrostyryl)pyrrolidine that was used directly without further purification.

Step B: Preparation of 4-bromo-2-nitrobenzaldehyde

To a solution of sodium periodate (298 g, 1.40 mol) in THF—$H_2O$ (4 L, 1:1) at 0° C. was added (E)-1-(4-bromo-2-nitrostyryl)pyrrolidine (138 g, 464 mmol). The mixture was stirred for 15 h and then filtered to remove solid precipitates. The aqueous layer from the filtrate was separated and extracted with EtOAc (4×200 mL). The combined organic layers were washed with $H_2O$ (2×200 mL), dried over $MgSO_4$, filtered, and concentrated under reduced pressure to give the crude product that was purified by silica gel flash column chromatography (5% EtOAc in hexanes) to afford 91 g (86%) of 4-bromo-2-nitrobenzaldehyde.

Step C: Preparation of 3-nitro-4'-(pyrrolidine-1-carbonyl)biphenyl-4-carbaldehyde To a solution of 4-bromo-2-nitrobenzaldehyde (20.2 g, 87.9 mmol), 4-(pyrrolidine-1-carbonyl)phenylboronic acid (21.2 g, 96.7 mmol), and $Pd(PPh_3)_4$ (508 mg, 0.440 mmol) in toluene (200 mL) was added EtOH (40 mL) followed by $Na_2CO_3$ (70.0 mL, 140 mmol, 2 M aq solution) at room temperature. The resulting mixture was heated at 100° C. for 18 h. The reaction mixture was cooled to room temperature and the organic layer was separated. The aqueous layer was extracted with EtOAc (300 mL). The combined organic layers were washed with brine (500 mL), dried over MgSO$_4$, filtered, and concentrated under reduced pressure to give the crude material that was combined with another batch of the crude material obtained from an additional run in the same reaction scale. The combined crude material was purified by silica gel flash column chromatography (CH$_2$Cl$_2$ to 1% MeOH in CH$_2$Cl$_2$) to afford 51 g (90%) of 3-nitro-4'-(pyrrolidine-1-carbonyl)biphenyl-4-carbaldehyde.

Step D: Preparation of (E)-ethyl 2-(cyanomethyl)-3-(3-nitro-4'-(pyrrolidine-1-carbonyl)biphenyl-4-yl)acrylate A mixture of 3-nitro-4'-(pyrrolidine-1-carbonyl)biphenyl-4-carbaldehyde (20.0 g, 61.7 mmol) and α-cyanomethylcarboethoxyethylidene triphenylphosphorane (26.3 g, 67.8 mmol) in toluene (200 mL) was gently refluxed for 2.5 h. The reaction mixture was cooled to room temperature and concentrated under reduced pressure to give the crude (E)-ethyl 2-(cyanomethyl)-3-(3-nitro-4'-(pyrrolidine-1-carbonyl)biphenyl-4-yl)acrylate that was used directly without further purification.

Step E: Preparation of (1E,4E)-ethyl 2-amino-8-(4-(pyrrolidine-1-carbonyl)phenyl)-3H-benzo[b]azepine-4-carboxylate To a solution of the crude (E)-ethyl 2-(cyanomethyl)-3-(3-nitro-4'-(pyrrolidine-1-carbonyl)biphenyl-4-yl)acrylate in AcOH (650 mL) was added iron (29.1 g, 521 mmol) at room temperature. The resulting mixture was heated at 85° C. for 4 h. The reaction mixture was cooled to room temperature and diluted with CH$_2$Cl$_2$ (250 mL). The solids were filtered off and washed with CH$_2$Cl$_2$ (200 mL). The filtrate was concentrated under reduced pressure to give the crude material that was diluted with CH$_2$Cl$_2$ (250 mL) again. To this mixture was slowly added sat'd aq Na$_2$CO$_3$ (~330 mL) with vigorous stirring until it became basic (pH ~9-10). The resulting mixture was filtered off and washed with CH$_2$Cl$_2$ (~250 mL). The aqueous layer was separated and extracted with CH$_2$Cl$_2$ (2×150 mL). The combined organic layers were washed with brine, dried over MgSO$_4$, and filtered to give the crude material that was diluted with EtOAc (70 mL). The mixture was kept for 16 h at room temperature. The suspension was filtered. The solids filtered off were washed with EtOAc (100 mL) to give the crude product that was washed with a small amount of CH$_2$Cl$_2$ to afford 20 g (62% based on 95% purity) of (1E,4E)-ethyl 2-amino-8-(4-(pyrrolidine-1-carbonyl)phenyl)-3H-benzo[b]azepine-4-carboxylate.

Step F: Preparation of (1E,4E)-ethyl 2-(tert-butoxycarbonylamino)-8-(4-(pyrrolidine-1-carbonyl)phenyl)-3H-benzo[b]azepine-4-carboxylate To a mixture of (1E,4E)-ethyl 2-amino-8-(4-(pyrrolidine-1-carbonyl)phenyl)-3H-benzo[b]azepine-4-carboxylate (9.60 g, 23.8 mmol) in CH$_2$Cl$_2$ (100 mL) was added Boc$_2$O (5.97 mg, 27.4 mmol) at room temperature. The reaction mixture was stirred for 3 days. The resulting mixture was washed with sat'd aq NaHCO$_3$ and brine. The organic layer was separated and dried over MgSO$_4$, filtered, and concentrated under reduced pressure to give 12.7 g of the crude (1E,4E)-ethyl 2-(tert-butoxycarbonylamino)-8-(4-(pyrrolidine-1-carbonyl)phenyl)-3H-benzo[b]azepine-4-carboxylate that was used directly without further purification. MS APCI(+) m/z 504 (M+1) detected.

Step G: Preparation of (1E,4E)-2-(tert-butoxycarbonylamino)-8-(4-(pyrrolidine-1-carbonyl)phenyl)-3H-benzo[b]azepine-4-carboxylic acid To a solution of (1E,4E)-ethyl 2-(tert-butoxycarbonylamino)-8-(4-(pyrrolidine-1-carbonyl)phenyl)-3H-benzo[b]azepine-4-carboxylate (12.0 g, 23.8 mmol) in THF-EtOH (60 mL/60 mL) was added 4 N aq. LiOH (23.8 mL, 95.3 mmol) at 0° C. The reaction mixture was warmed to room temperature and stirred for 21 h. Additional 6 mL of 4 N aq LiOH was added twice after 21 h and 24 h. After stirring for additional 6 h, the resulting mixture was concentrated under reduced pressure to give the crude material that was diluted with water (50 mL) and acidified to a pH of ~3.5 with 1 N aq phosphoric acid (~450 mL). ~250 mL of CH$_2$Cl$_2$ was added during acidification to extract the crude product out of the sticky suspension. The solids formed during acidification were filtered off using a glass filter packed with Celite. The aqueous layer was separated and extracted with CH$_2$Cl$_2$ (3×100 mL). The combined organic layers were dried over MgSO$_4$, filtered, and concentrated under reduced pressures to give 10.2 g (90%) of the crude (1E,4E)-2-(tert-butoxycarbonylamino)-8-(4-(pyrrolidine-1-carbonyl)phenyl)-3H-benzo[b]azepine-4-carboxylic acid that was used directly without further purification. MS APCI(+) m/z 476 (M+1) detected.

Step H: Preparation of tert-butyl (1E,4E)-4-(propylcarbamoyl)-8-(4-(pyrrolidine-1-carbonyl)phenyl)-3H-benzo[b]azepin-2-ylcarbamate A mixture of (1E,4E)-2-(tert-butoxycarbonylamino)-8-(4-(pyrrolidine-1-carbonyl)phenyl)-3H-benzo[b]azepine-4-carboxylic acid (200 mg, 0.42 mmol), HOBt (114 mg, 0.84 mmol), and EDCI (161 mg, 0.84 mmol) in DMF (5 mL) was stirred for 1 h at room temperature. To this mixture was added triethylamine (0.12 mL, 0.84 mmol) and propan-1-amine (0.043 mL, 0.53 mmol) at room temperature. The resulting solution was stirred for additional 2 h. The reaction mixture was diluted with EtOAc (5 mL) and washed with sat'd aq NH$_4$Cl. The aqueous layer was separated and extracted with EtOAc (3×5 mL). The combined organic layers were washed with brine (5 mL), sat'd aq NaHCO$_3$ (5 mL), and brine (5 mL). The organic layer was dried over MgSO$_4$, filtered, and concentrated under reduced pressure to give the crude tert-butyl (1E,4E)-4-(propylcarbamoyl)-8-(4-(pyrrolidine-1-carbonyl)phenyl)-3H-benzo[b]azepin-2-ylcarbamate that was used directly without further purification.

Step I: Preparation of (1E,4E)-2-amino-N-propyl-8-(4-(pyrrolidine-1-carbonyl)phenyl)-3H-benzo[b]azepine-4-carboxamide To a solution of tert-butyl (1E,4E)-4-(propylcarbamoyl)-8-(4-(pyrrolidine-1-carbonyl)phenyl)-3H-benzo[b]azepin-2-ylcarbamate (450 mg, 0.87 mmol) in CH$_2$Cl$_2$ (5 mL) was added 2,2,2-trifluoroacetic acid (1.36 mL, 17.4 mmol) at 0° C. The reaction mixture was warmed to room temperature and stirred for 2 h. The reaction mixture was concentrated under reduced pressure to give the crude material that was diluted with CH$_2$Cl$_2$ (10 mL) and sat'd aq NaHCO$_3$ (15 mL) again. The resulting mixture was stirred for 30 min at room temperature. The aqueous layer was separated and extracted with CH$_2$Cl$_2$ (1×10 mL). The combined organic layers were washed with sat'd aq NaHCO$_3$ (2×10 mL) and brine (1×10 mL), dried over MgSO$_4$, filtered, and concentrated under reduced pressure to give the crude material again that was purified by silica gel flash column chromatography (1 to 5% MeOH in CH$_2$Cl$_2$, gradient) to yield 27 mg (7%) of (1E,4E)-2-amino-N-propyl-8-(4-(pyrrolidine-1-carbonyl)phenyl)-3H-benzo[b]azepine-4-carboxamide. MS APCI(+) m/z 417 (M+1) detected; $^1$H-NMR (400 MHz, d$_6$-DMSO) δ 8.27 (t, 1H), 7.75 (d, 2H), 7.62 (d, 2H), 7.50 (d, 2H), 7.41 (d, 2H), 3.43-3.51 (m, 4H), 3.18 (q, 2H), 2.99 (s, 2H), 1.81-1.90 (m, 4H), 1.48-1.58 (m, 2H), 0.90 (t, 3H).

The following examples 102 and 103 were prepared by the procedures as described in Example 101 (Step H and I) using (1E,4E)-2-(tert-butoxycarbonylamino)-8-(4-(pyrrolidine-1-carbonyl)phenyl)-3H-benzo[b]azepine-4-carboxylic acid and N-propylbutan-2-amine or diisobutylamine.

Example 102

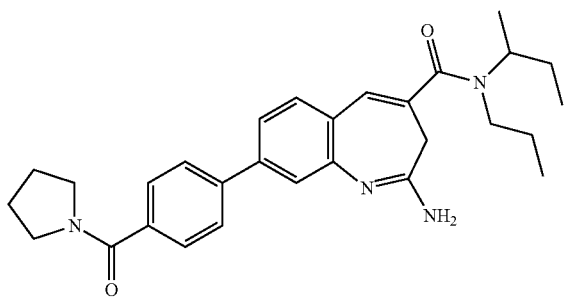 [SMILES: CCCN(C(=O)C1=Cc2ccc(-c3ccc(C(=O)N4CCCC4)cc3)cc2N=C(N)C1)C(C)CC]

(1E,4E)-2-amino-N-sec-butyl-N-propyl-8-(4-(pyrrolidine-1-carbonyl)phenyl)-3H-benzo[b]azepine-4-carboxamide MS APCI(+) m/z 473 (M+1) detected; $^1$H-NMR (400 MHz, CDCl$_3$) δ 7.67 (d, 2H), 7.60 (d, 2H), 7.52 (s, 1H), 7.36 (d, 1H), 7.32 (dd, 1H), 6.80 (s, 1H), 4.21-4.26 (m, 1H), 3.67 (t, 2H), 3.50 (t, 2H), 3.37-3.44 (m, 1H), 2.95-3.10 (m, 1H), 2.92 (d, 1H), 2.79 (d, 1H), 1.88-2.00 (m, 4H), 1.50-1.77 (m, 4H), 1.29 (d, 3H), 0.94 (t, 3H), 0.86 (br s, 3H).

Example 103

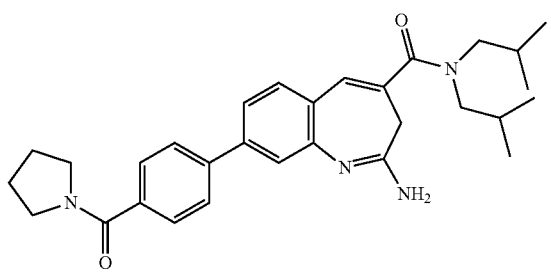 [SMILES: CC(C)CN(CC(C)C)C(=O)C1=Cc2ccc(-c3ccc(C(=O)N4CCCC4)cc3)cc2N=C(N)C1]

(1E,4E)-2-amino-N,N-diisobutyl-8-(4-(pyrrolidine-1-carbonyl)phenyl)-3H-benzo[b]azepine-4-carboxamide MS APCI(+) m/z 487 (M+1) detected; $^1$H-NMR (400 MHz, CDCl$_3$) δ 7.68 (d, 2H), 7.60 (d, 2H), 7.51 (s, 1H), 7.39 (d, 1H), 7.31 (dd, 1H), 6.82 (s, 1H), 3.67 (t, 2H), 3.51 (t, 2H), 3.22-3.52 (br s, 4H), 2.81 (s, 2H), 1.88-2.14 (m, 6H), 0.90 (br s, 12H).

Example 104

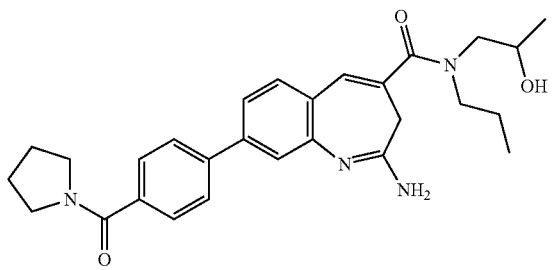 [SMILES: CCCN(CC(C)O)C(=O)C1=Cc2ccc(-c3ccc(C(=O)N4CCCC4)cc3)cc2N=C(N)C1]

(1E,4E)-2-amino-N-(2-hydroxypropyl)-N-propyl-8-(4-(pyrrolidine-1-carbonyl)phenyl)-3H-benzo[b]azepine-4-carboxamide Step A: Preparation of 2-(tert-butyldimethylsilyloxy)-N-propylpropan-1-amine To a solution of 1-(propylamino)propan-2-ol (8.00 g, 68.3 mmol), tert-butylchlorodimethylsilane (10.9 g, 72.4 mmol), and catalytic amount of DMAP in CH$_2$Cl$_2$ (68 mL) at 0° C. was added dropwise TEA (9.61 ml, 68.3 mmol). The reaction mixture was warmed to room temperature and stirred for 20 h. Additional 1 mL of TEA was added and stirred for additional 20 h. Water (60 mL) was added. The layers were separated. The aqueous layer was extracted with EtOAc (1×). The combined organic layers were washed with brine, dried over MgSO$_4$, filtered, and concentrated under reduced pressure to give the crude material that was filtered again to afford quantitatively 2-(tert-butyldimethylsilyloxy)-N-propylpropan-1-amine that was used directly without further purification.

Step B: Preparation of (1E,4E)-2-amino-N-(2-hydroxypropyl)-N-propyl-8-(4-(pyrrolidine-1-carbonyl)phenyl)-3H-benzo[b]azepine-4-carboxamide The title compound was prepared by the procedures as described in Example 101 (Steps H and I) using (1E,4E)-2-(tert-butoxycarbonylamino)-8-(4-(pyrrolidine-1-carbonyl)phenyl)-3H-benzo[b]azepine-4-carboxylic acid and 2-(tert-butyldimethylsilyloxy)-N-propylpropan-1-amine. MS APCI (+) m/z 475 (M+1) detected; $^1$H-NMR (400 MHz, CDCl$_3$) δ 7.67 (d, 2H), 7.60 (d, 2H), 7.49 (s, 1H), 7.29-7.34 (m, 2H), 6.87 (s, 1H), 4.11 (br s, 1H), 3.48-3.71 (m, 7H), 3.29 (dd, 1H), 2.93 (d, 1H), 2.80 (d, 1H), 1.86-2.01 (m, 4H), 1.61-1.74 (m, 2H), 1.22 (d, 3H), 0.91 (t, 3H).

The following examples 105 and 106 were prepared by chiral separation of example 104 (column: Chiral Tech IA semi-prep column (10 mm×250 mm); flow rate: 4.8 mL/min; UV: 220 nm, solvents: EtOH-isooctane (50:50)). Their absolute configuration was arbitrarily assigned.

Example 105

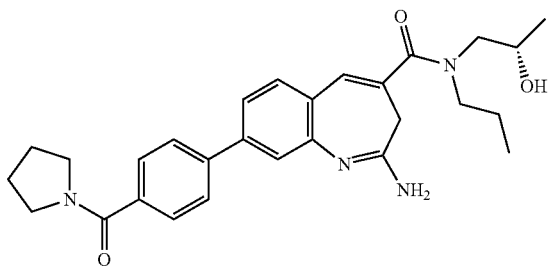 [SMILES: CCCN(C[C@H](C)O)C(=O)C1=Cc2ccc(-c3ccc(C(=O)N4CCCC4)cc3)cc2N=C(N)C1]

(1E,4E)-2-amino-N—((S)-2-hydroxypropyl)-N-propyl-8-(4-(pyrrolidine-1-carbonyl)phenyl)-3H-benzo[b]azepine-4-carboxamide Retention time 10.08 min.

Example 106

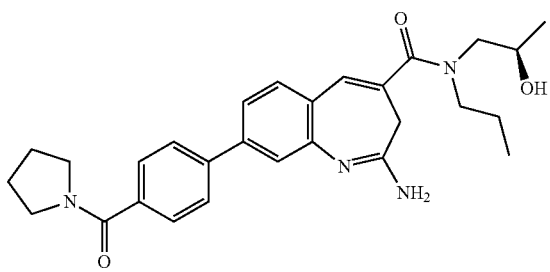 [SMILES: CCCN(C[C@@H](C)O)C(=O)C1=Cc2ccc(-c3ccc(C(=O)N4CCCC4)cc3)cc2N=C(N)C1]

(1E,4E)-2-amino-N—((R)-2-hydroxypropyl)-N-propyl-8-(4-(pyrrolidine-1-carbonyl)phenyl)-3H-benzo[b]azepine-4-carboxamide Retention time 9.09 min.

Example 107

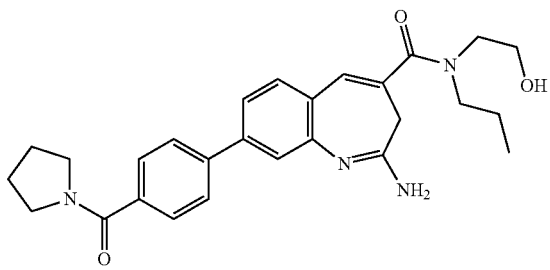 [SMILES: CCCN(CCO)C(=O)C1=Cc2ccc(-c3ccc(C(=O)N4CCCC4)cc3)cc2N=C(N)C1]

(1E,4E)-2-amino-N-(2-hydroxyethyl)-N-propyl-8-(4-(pyrrolidine-1-carbonyl)phenyl)-3H-benzo[b]azepine-4-carboxamide The title compound was prepared by the procedures as described in Example 104 using (1E,4E)-2-(tert-butoxycarbonylamino)-8-(4-(pyrrolidine-1-carbonyl)phenyl)-3H-benzo[b]azepine-4-carboxylic acid and N-(2-(tert-butyldimethylsilyloxy)ethyl)propan-1-amine that was prepared by the procedure as described in Example 104 (Step A) using 2-(propylamino)ethanol. MS APCI (+) m/z 461 (M+1) detected; $^1$H-NMR (400 MHz, CDCl$_3$) δ 7.68 (d, 2H), 7.60 (d, 2H), 7.49 (s, 1H), 7.29-7.35 (m, 2H), 6.88 (s, 1H), 3.84 (s, 2H), 3.67 (t, 4H), 3.50 (t, 4H), 2.84 (s, 2H), 1.88-2.00 (m, 4H), 1.66-1.72 (m, 2H), 0.93 (t, 3H).

Example 109

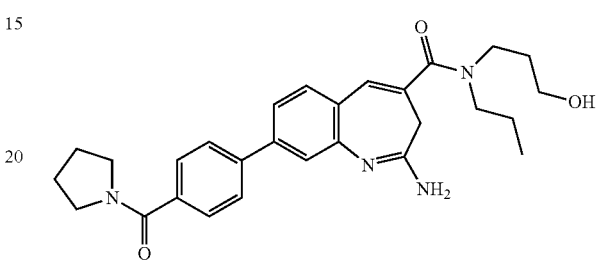

(1E,4E)-2-amino-N-(3-hydroxypropyl)-N-propyl-8-(4-(pyrrolidine-1-carbonyl)phenyl)-3H-benzo[b]azepine-4-carboxamide Step A: Preparation of 3-(tert-butyldimethylsilyloxy)-N-propylpropan-1-amine The title compound was prepared by the procedure as described in Example 104 (Step A) using 3-(propylamino)propan-1-ol.

Step B: Preparation of tert-butyl (1E,4E)-4-((3-(tert-butyldimethylsilyloxy)propyl)(propyl)carbamoyl)-8-(4-(pyrrolidine-1-carbonyl)phenyl)-3H-benzo[b]azepin-2-ylcarbamate The title compound was prepared by the procedure as described in Example 101 (Step H) using (1E,4E)-2-(tert-butoxycarbonylamino)-8-(4-(pyrrolidine-1-carbonyl)phenyl)-3H-benzo[b]azepine-4-carboxylic acid and 3-(tert-butyldimethylsilyloxy)-N-propylpropan-1-amine. MS APCI(+) m/z 689 detected.

Step C: Preparation of (1E,4E)-2-amino-N-(3-hydroxypropyl)-N-propyl-8-(4-(pyrrolidine-1-carbonyl)phenyl)-3H-benzo[b]azepine-4-carboxamide To a mixture of tert-butyl (1E,4E)-4-(3-(tert-butyldimethylsilyloxy)propyl)(propyl)carbamoyl)-8-(4-(pyrrolidine-1-carbonyl)phenyl)-3H-benzo[b]azepin-2-ylcarbamate (459 mg, 0.37 mmol) in CH$_2$Cl$_2$ (4 mL) at 0° C. was added TFA (1.00 mL). The resulting mixture was warmed to room temperature and stirred for 1 h. The reaction mixture was concentrated under reduced pressure to give the crude material that was azeotroped with toluene-EtOH (3 mL/1 mL) twice. The crude material was dried under reduced pressure for 30 min. The crude material was dissolved into CH$_2$Cl$_2$ (~3 mL) again and treated with NH$_3$ in MeOH (0.30 mL, 2.1 mmol, 7 N solution in MeOH) at room temperature. The resulting mixture was stirred for 1 h. The resulting mixture was concentrated under reduced pressure to give the crude material that was purified by silica gel flash column chromatography (3 to 7% MeOH in $CH_2Cl_2$, gradient) to afford 105 mg (59%) of (1E,4E)-2-amino-N-(3-hydroxypropyl)-N-propyl-8-(4-(pyrrolidine-1-carbonyl)phenyl)-3H-benzo[b]azepine-4-carboxamide. MS APCI (+) m/z 475 detected; $^1$H-NMR (400 MHz, $CDCl_3$) δ 7.67 (d, 2H), 7.60 (d, 2H), 7.51 (br s, 1H), 7.30-7.37 (m, 2H), 6.88 (s, 1H), 3.60-3.69 (m, 6H), 3.48-3.52 (m, 4H), 2.83 (s, 2H), 1.82-2.00 (m, 6H), 1.68-1.74 (m, 2H), 0.93 (t, 3H).

Example 110

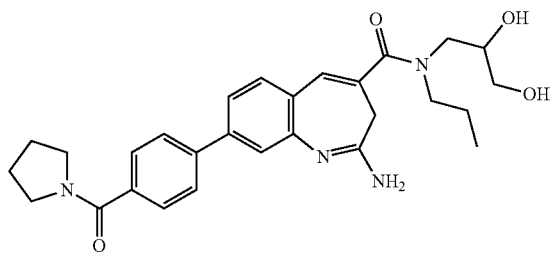 [SMILES: CCCN(CC(O)CO)C(=O)C1=Cc2ccc(-c3ccc(C(=O)N4CCCC4)cc3)cc2N=C(N)C1]

(1E,4E)-2-amino-N-(2,3-dihydroxypropyl)-N-propyl-8-(4-(pyrrolidine-1-carbonyl)phenyl)-3H-benzo[b]azepine-4-carboxamide Step A: Preparation of 2,2-dimethyl-1,3-dioxolane-4-carbaldehyde A solution of anhydrous DMSO (3.41 mL, 48 mmol) in $CH_2Cl_2$ (5 mL) was added dropwise to a stirred solution of oxalyl chloride (1.92 mL, 22 mmol) in $CH_2Cl_2$ (50 mL) at −60° C. To this mixture was added a solution of (2,2-dimethyl-[1,3]dioxolan-4-yl)-methanol (2.48 mL, 20 mmol) in $CH_2Cl_2$ (10 mL). The resulting mixture was stirred for 15 min at −60° C. TEA (13.9 mL, 100 mmol) was added dropwise. The reaction mixture was then warmed to room temperature. Water (50 mL) and $CH_2Cl_2$ (50 mL) were added. The organic layer was separated and washed with water (25 mL). The aqueous layer was extracted with $CH_2Cl_2$ (3×50 mL). The organic layers were dried over $MgSO_4$, filtered, and concentrated under reduced pressure to afford the crude 2,2-dimethyl-1,3-dioxolane-4-carbaldehyde that was used directly without further purification.

Step B: Preparation of N-((2,2-dimethyl-1,3-dioxolan-4-yl)methyl)propan-1-amine

To a solution of propylamine (0.72 mL, 7.7 mmol) and 2,2-dimethyl-1,3-dioxolane-4-carbaldehyde (1.0 g, 7.7 mmol) in 1,2-dichloroethane (25 mL) was added sodium triacetoxyborohydride (2.28 g, 10.8 mmol). The mixture was stirred for 1.5 h at room temperature. The reaction mixture was then quenched with sat'd aq $NaHCO_3$ and extracted with EtOAc. The organic layer was dried with $MgSO_4$, filtered, and concentrated under reduced pressure to give the crude material that was purified by silica gel flash column chromatography ($CH_2Cl_2$ to 10% MeOH in $CH_2Cl_2$, gradient) to afford 1.26 g (73%) of N-((2,2-dimethyl-1,3-dioxolan-4-yl)methyl)propan-1-amine.

Step C: Preparation of (1E,4E)-2-amino-N-(2,3-dihydroxypropyl)-N-propyl-8-(4-(pyrrolidine-1-carbonyl)phenyl)-3H-benzo[b]azepine-4-carboxamide The title compound was prepared by the procedures as described in Example 101 (Step H and I) using (1E,4E)-2-(tert-butoxycarbonylamino)-8-(4-(pyrrolidine-1-carbonyl)phenyl)-3H-benzo[b]azepine-4-carboxylic acid and N-((2,2-dimethyl-1,3-dioxolan-4-yl)methyl)propan-1-amine.

Example 112

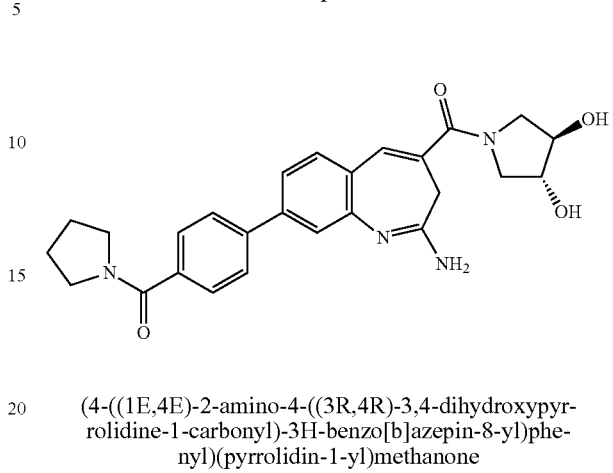

(4-((1E,4E)-2-amino-4-((3R,4R)-3,4-dihydroxypyrrolidine-1-carbonyl)-3H-benzo[b]azepin-8-yl)phenyl)(pyrrolidin-1-yl)methanone Step A: Preparation of (3R,4R)-1-benzyl-3,4-bis(tert-butyldimethylsilyloxy)pyrrolidine To a solution of (3R,4R)-1-benzylpyrrolidine-3,4-diol (7.00 g, 36.2 mmol) and 1H-imidazole (10.9 g, 159 mmol) in DMF (35 mL) at 0° C. was added tert-butylchlorodimethylsilane (12.0 g, 79.7 mmol). After stirring for 10 min, the mixture was heated to 60° C. for 4 hours. After cooling to room temperature, the reaction was diluted with $H_2O$ (25 ml) and extracted with pet ether (3×20 mL). The combined organic layers were washed with $H_2O$ (2×20 mL) and sat'd aq $NaHCO_3$ (2×20 mL), dried over $MgSO_4$, filtered and concentrated under reduced pressure to give the crude that was filtered through a silica plug (1% MeOH in $CH_2Cl_2$) to afford 13.4 g (88%) of (3R,4R)-1-benzyl-3,4-bis(tert-butyldimethylsilyloxy)pyrrolidine.

Step B: Preparation of (3R,4R)-3,4-bis(tert-butyldimethylsilyloxy)pyrrolidine

A mixture of (3R,4R)-1-benzyl-3,4-bis(tert-butyldimethylsilyloxy)pyrrolidine (13.4 g, 31.8 mmol) and $Pd(OH)_2/C$ (2.23 g, 3.18 mmol, 20%) in MeOH (134 mL) was stirred for 20 h under $H_2$ atmosphere (balloon). The reaction mixture was filtered through a Celite plug and concentrated under reduced pressure to afford 10.5 g (91%) of the crude (3R,4R)-3,4-bis(tert-butyldimethylsilyloxy)pyrrolidine that was used directly without further purification.

Step C: Preparation of (4-((1E,4E)-2-amino-4-((3R,4R)-3,4-dihydroxypyrrolidine-1-carbonyl)-3H-benzo[b]azepin-8-yl)phenyl)(pyrrolidin-1-yl)methanone The title compound was prepared by the procedures as described in Example 101 (Steps H and I) with conc. HCl instead of TFA using (1E,4E)-2-(tert-butoxycarbonylamino)-8-(4-(pyrrolidine-1-carbonyl)phenyl)-3H-benzo[b]azepine-4-carboxylic acid and (3R,4R)-3,4-bis(tert-butyldimethylsilyloxy)pyrrolidin.

The following examples 115 and 117 were prepared by the procedures as described in Example 101 (Steps H and I) using (1E,4E)-2-(tert-butoxycarbonylamino)-8-(4-(pyrrolidine-1-carbonyl)phenyl)-3H-benzo[b]azepine-4-carboxylic acid and the appropriate amines (2-methyl-1-(propylamino)propan-2-ol was prepared by the procedure reported in *J. Am. Chem. Soc.* 1939, 61, 3562) or the hydroxylamine.

Example 115

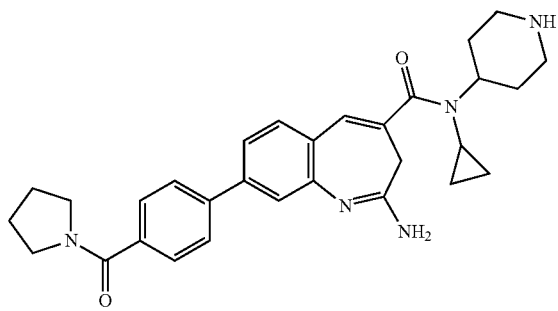 [SMILES: NC1=Nc2cc(-c3ccc(C(=O)N4CCCC4)cc3)ccc2C=C(C(=O)N(C2CCNCC2)C2CC2)C1]

(1E,4E)-2-amino-N-cyclopropyl-N-(piperidin-4-yl)-8-(4-(pyrrolidine-1-carbonyl)phenyl)-3H-benzo[b]azepine-4-carboxamide m/z (APCI-pos) M+1=481.2.

Example 117

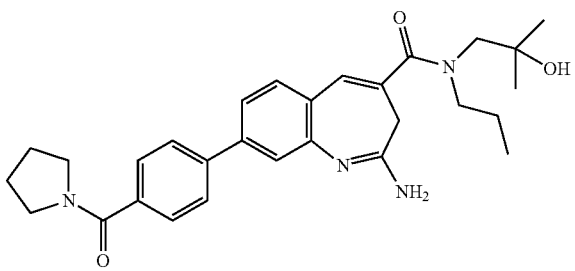 [SMILES: CCCN(CC(C)(C)O)C(=O)C1=Cc2ccc(-c3ccc(C(=O)N4CCCC4)cc3)cc2N=C(N)C1]

(1E,4E)-2-amino-N-(2-hydroxy-2-methylpropyl)-N-propyl-8-(4-(pyrrolidine-1-carbonyl)phenyl)-3H-benzo[b]azepine-4-carboxamide m/z (APCI-pos) M+1=489.2.

The following examples 119, 120, 121, and 122 were prepared by the procedures as described in Example 101 (Step H and I) using (1E,4E)-2-(tert-butoxycarbonylamino)-8-(4-(pyrrolidine-1-carbonyl)phenyl)-3H-benzo[b]azepine-4-carboxylic acid and the appropriate amines.

Example 119

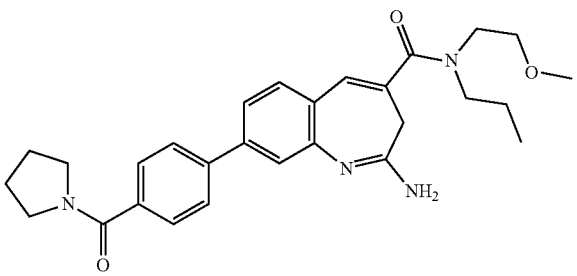 [SMILES: CCCN(CCOC)C(=O)C1=Cc2ccc(-c3ccc(C(=O)N4CCCC4)cc3)cc2N=C(N)C1]

(1E,4E)-2-amino-N-(2-methoxyethyl)-N-propyl-8-(4-(pyrrolidine-1-carbonyl)phenyl)-3H-benzo[b]azepine-4-carboxamide MS APCI (+) m/z 475 (M+1) detected; $^1$H-NMR (400 MHz, CDCl$_3$) δ 7.67 (d, 2H), 7.60 (d, 2H), 7.52 (s, 1H), 7.37 (d, 1H), 7.31-7.33 (m, 1H), 6.91 (s, 1H), 3.68 (t, 4H), 3.58 (br s, 2H), 3.50 (t, 4H), 3.37 (s, 3H), 2.85 (s, 2H), 1.88-2.01 (m, 4H), 1.62-1.70 (m, 2H), 0.93 (t, 3H).

Example 120

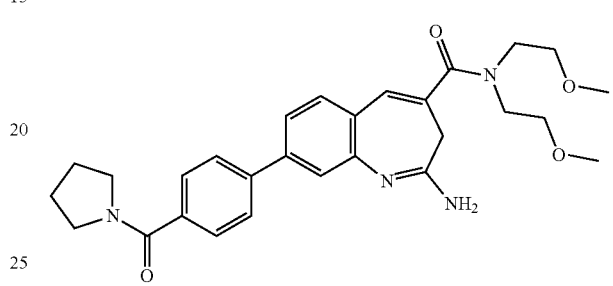

(1E,4E)-2-amino-N,N-bis(2-methoxyethyl)-8-(4-(pyrrolidine-1-carbonyl)phenyl)-3H-benzo[b]azepine-4-carboxamide MS APCI (+) m/z 491 (M+1) detected; $^1$H-NMR (400 MHz, CDCl$_3$) δ 7.67 (d, 2H), 7.60 (d, 2H), 7.50 (s, 1H), 7.38 (d, 1H), 7.30 (dd, 1H), 6.99 (s, 1H), 3.76 (br s, 4H), 3.67 (t, 2H), 3.60 (br s, 4H), 3.50 (t, 2H), 3.37 (s, 6H), 2.83 (s, 2H), 1.88-2.00 (m, 4H).

Example 121

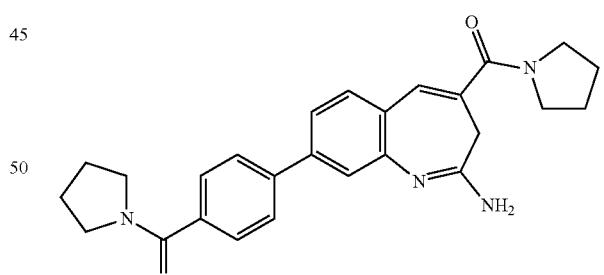

(4-(((1E,4E)-2-amino-4-(pyrrolidine-1-carbonyl)-3H-benzo[b]azepin-8-yl)phenyl)(pyrrolidin-1-yl)methanone MS APCI (+) m/z 429 (M+1) detected; $^1$H-NMR (400 MHz, CDCl$_3$) δ 7.68 (d, 2H), 7.60 (d, 2H), 7.51 (s, 1H), 7.38 (d, 1H), 7.30 (d, 1H), 7.06 (s, 1H), 3.74 (br s, 2H), 3.67 (br s, 2H), 3.60 (br s, 2H), 3.50 (br s, 2H), 2.88 (s, 2H), 1.90-1.97 (m, 8H).

Example 122

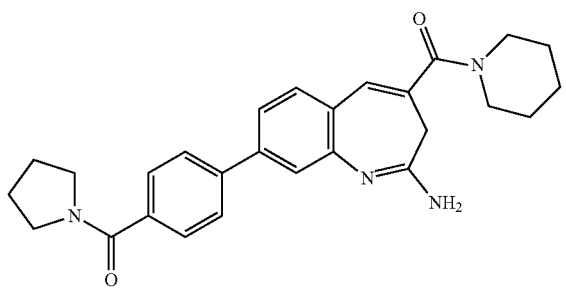 [SMILES: NC1=Nc2cc(-c3ccc(C(=O)N4CCCC4)cc3)ccc2C=C(C(=O)N2CCCCC2)C1]

(4-((1E,4E)-2-amino-4-(piperidine-1-carbonyl)-3H-benzo[b]azepin-8-yl)phenyl)(pyrrolidin-1-yl)methanone MS APCI (+) m/z 443 (M+1) detected; $^1$H-NMR (400 MHz, CDCl$_3$) δ 7.68 (d, 1H), 7.62-7.67 (m, 4H), 7.56 (dd, 1H), 7.45 (d, 1H), 6.93 (s, 1H), 3.66-3.70 (m, 6H), 3.49 (t, 2H), 3.23 (s, 2H), 1.90-2.01 (m, 4H), 1.74 (m, 2H), 1.67 (m, 4H).

Example 124

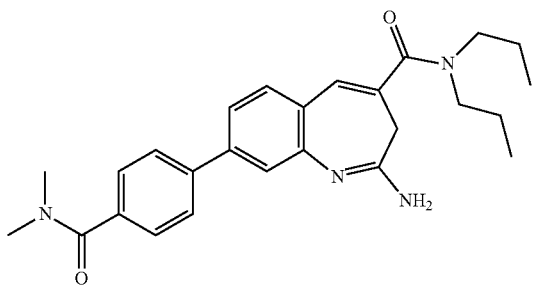 [SMILES: CCCN(CCC)C(=O)C1=Cc2ccc(-c3ccc(C(=O)N(C)C)cc3)cc2N=C(N)C1]

(1E,4E)-2-amino-8-(4-(dimethylcarbamoyl)phenyl)-N,N-dipropyl-3H-benzo[b]azepine-4-carboxamide

Step A: Preparation of (E)-ethyl 3-(4-bromo-2-nitrophenyl)-2-(cyanomethyl)acrylate A mixture of 4-bromo-2-nitrobenzaldehyde (30.0 g, 130.4 mmol) and α-cyanomethylcarboethoxyethylidene triphenylphosphorane (54.4 g, 140 mmol) in toluene (480 mL) was heated for 3 h at 110° C. The reaction mixture was cooled to room temperature. The solids were filtered off and washed with toluene (50 mL). The filtrate was concentrated again under reduced pressure to give the crude material that was triturated in heptane (100 mL). The precipitates were filtered off and washed with heptane (20 mL). After drying under reduced pressure the crude product was taken into MeOH (250 mL) at room temperature and swirled several times during 30 min. The mixture was kept at freezer for 16 h, filtered, and rinsed with pre-chilled MeOH (2×20 mL) to afford 36.6 g (83%) of (E)-ethyl 3-(4-bromo-2-nitrophenyl)-2-(cyanomethyl)acrylate.

Step B: Preparation of (1E,4E)-ethyl 2-amino-8-bromo-3H-benzo[b]azepine-4-carboxylate A mixture of (E)-ethyl 3-(4-bromo-2-nitrophenyl)-2-(cyanomethyl)acrylate (20.0 g, 59.0 mmol) in AcOH (380 mL) was heated to 80° C. To this mixture iron (19.8 g, 354 mmol) was added portionwise over 1 h keeping the internal temperature below 100° C. After completion of addition of iron, the reaction mixture was heated for additional 2.5 h at 80-85° C. until the starting material disappeared on HPLC. The reaction mixture was cooled to room temperature and filtered through a GF/F filter packed with Celite rinsing with AcOH. The filtrate was concentrated under reduced pressure to give the crude material which was diluted with water (150 mL). The aqueous mixture was treated with sat'd NaHCO$_3$ (200 mL) until it became basic (pH>8). To the suspension was added additional EtOAc (350 mL). The whole mixture was filtered through a filter packed with Celite. The solids filtered off were diluted with EtOAc (300 mL), stirred for 15 min, and filtered again. This process with the solids filtered off was repeated one more time. All of the organic layers were combined and washed with sat'd aq NaHCO$_3$ (300 mL) followed by brine (300 mL), dried over MgSO$_4$, filtered while rinsing with EtOAc, and concentrated under reduced pressure to give the crude material that was triturated with ether (100 mL) to afford 16.5 g (91%) of (1E,4E)-ethyl 2-amino-8-bromo-3H-benzo[b]azepine-4-carboxylate.

Step C: Preparation of (1E,4E)-ethyl 8-bromo-2-(tert-butoxycarbonylamino)-3H-benzo[b]azepine-4-carboxylate To a suspension of (1E,4E)-ethyl 2-amino-8-bromo-3H-benzo[b]azepine-4-carboxylate (16.5 g, 53.4 mmol) in CH$_2$Cl$_2$ (165 mL) at 0° C. was added TEA (11.2 ml, 80.2 mmol). The resulting mixture was stirred for 10 min at 0° C. To this mixture was added Boc$_2$O (17.5 g, 80.2 mmol) in CH$_2$Cl$_2$ (10 mL) at 0° C. The reaction mixture was warmed to room temperature and stirred for 24 h. Additional 1.16 g (5.32 mmol) of Boc$_2$O and 0.75 mL (5.35 mmol) of TEA were added. The resulting mixture was stirred for additional 24 h. The reaction mixture was quenched with water (65 mL). The organic layer was separated and the aqueous layer was extracted with CH$_2$Cl$_2$ (65 mL). The combined organic layers were washed with sat'd aq NaHCO$_3$ (2×100 mL) followed by brine (100 mL). The organic layer was dried over MgSO$_4$, filtered rising with CH$_2$Cl$_2$, and concentrated under reduced pressure to give the crude material that was treated with heptane (100 mL). The suspension of the crude material in heptane was stirred for 1.5 h at room temperature, filtered, and rinsed with heptane to afford 19.0 g (87%) of (1E,4E)-ethyl 8-bromo-2-(tert-butoxycarbonylamino)-3H-benzo[b]azepine-4-carboxylate. MS APCI(+) m/z 409, 411 (M+1, Br pattern) detected.

Step D: Preparation of (1E,4E)-8-bromo-2-(tert-butoxycarbonylamino)-3H-benzo[b]azepine-4-carboxylic acid To a solution of (1E,4E)-ethyl 8-bromo-2-(tert-butoxycarbonylamino)-3H-benzo[b]azepine-4-carboxylate (15.0 g, 36.7 mmol) in THF (195 mL) at −15° C. was slowly added 1N aq NaOH (55.0 ml, 55.0 mmol) over 10 min. The reaction mixture was warmed to room temperature and stirred for 18 h. The reaction mixture was poured into ice-cold water (500 mL). The pH of the mixture was carefully adjusted to 5-6 with 0.5 N aq HCl (~260 mL). The resulting mixture was extracted with EtOAc. The aqueous layer was extracted with EtOAc (1x). The combined organic layers were washed with brine, dried over MgSO$_4$, filtered while rinsing with EtOAc, and concentrated under reduced pressure to give the crude material that was triturated with MeCN (20 mL). The solids were filtered off and dried under reduced pressure to afford 7.56 g (54%) of the desired product. The filtrate was concentrated under reduced pressure again to give the second crude material that was triturated with MeCN again to afford additional 1.33 g (9.5%) of the product. Total 8.89 g (64%) of (1E,4E)-8-bromo-2-(tert-butoxycarbonylamino)-3H-benzo[b]azepine-4-carboxylic acid was obtained. MS APCI(+) m/z 381, 383 (M+1, Br pattern) detected.

Step E: Preparation of tert-butyl (1E,4E)-8-bromo-4-(dipropylcarbamoyl)-3H-benzo[b]azepin-2-ylcarbamate To a solution of dipropylamine (2.16 ml, 15.7 mmol) in CH$_2$Cl$_2$ (50 mL) at −10° C. was added EDCI (3.02 g, 15.7 mmol) followed by diisopropylethylamine (2.97 ml, 17.1 mmol) over 5 min. The resulting mixture was stirred for 40 min at −15° C. To the reaction mixture was added (1E,4E)-8-bromo-2-(tert-butoxycarbonylamino)-3H-benzo[b]azepine-4-carboxylic acid (5.00 g, 13.1 mmol) followed by HOBt (2.13 g, 15.7 mmol) over 5 min maintaining the reaction temperature between −15 to −12° C. The resulting mixture was warmed to room temperature and stirred for 19 h. The reaction mixture was poured onto water (50 mL). The organic layer was separated and the aqueous layer was extracted with CH$_2$Cl$_2$ (50 mL). The combined organic layers were washed with sat'd aq NH$_4$Cl (75 mL). The organic layer was separated. The sat'd aq NH$_4$Cl solution was extracted with CH$_2$Cl$_2$ (50 mL) again. The combined organic layers were washed with sat'd aq NaHCO$_3$ (2×75 mL) followed by brine (2×100 mL). The organic layer was dried over MgSO$_4$, filtered, and concentrated under reduced pressure to give the crude material that was taken into ether (50 mL) and kept in the freezer for 16 h. The precipitates were filtered off and the filtrate was concentrated under reduced pressure to afford 4.64 g (76%) of tert-butyl (1E,4E)-8-bromo-4-(dipropylcarbamoyl)-3H-benzo[b]azepin-2-ylcarbamate. MS APCI(+) m/z 464, 466 (M+1, Br pattern) detected.

Step F: Preparation of tert-butyl (1E,4E)-8-(4-(dimethylcarbamoyl)phenyl)-4-dipropylcarbamoyl)-3H-benzo[b]azepin-2-ylcarbamate To Na$_2$CO$_3$ (129 mg, 1.214 mmol) in a 50 mL round-bottom flask was added water (3.7 mL) was bubbled with N$_2$ for 10 min. To this mixture was added tert-butyl (1E,4E)-8-bromo-4-(dipropylcarbamoyl)-3H-benzo[b]azepin-2-ylcarbamate (200 mg, 0.40 mmol) in EtOH (4.9 mL) at room temperature. The resulting mixture was bubbled with N$_2$ for 10 min. Pd(OAc)$_2$ (9.3 mg, 0.040 mmol) and 4,4'-(phenylphosphinidene)bisbenzenesulfonic acid dipotassium hydrate (45 mg, 0.081 mmol) were added. The resulting mixture was warmed to 65° C. with N$_2$ bubbling. To this mixture was added a solution of 4-(dimethylcarbamoyl)phenylboronic acid (97 mg, 0.49 mmol) in EtOH (0.6 mL). The resulting mixture was stirred at 65° C. for 1 h. The reaction mixture was cooled to room temperature and concentrated under reduced pressure to give the crude material that was diluted with water (5 mL) and EtOAc (10 mL). The mixture was filtered through GF/F filter. The aqueous layer was separated and extracted with EtOAc (10 mL). The combined organic layers were washed with brine (10 mL), dried over MgSO$_4$, filtered, and concentrated under reduced pressure to give the crude product that was purified by silica gel flash column chromatography (CH$_2$Cl$_2$ to 2% MeOH in CH$_2$Cl$_2$) to afford 178 mg (83%) of tert-butyl (1E,4E)-8-(4-(dimethylcarbamoyl)phenyl)-4-(dipropylcarbamoyl)-3H-benzo[b]azepin-2-ylcarbamate. MS APCI(+) m/z 533 (M+1) detected.

Step G: Preparation of (1E,4E)-2-amino-8-(4-(dimethylcarbamoyl)phenyl)-N,N-dipropyl-3H-benzo[b]azepine-4-carboxamide The title compound was prepared by the procedure as described in Example 101 (Step I). MS APCI(+) m/z 433 (M+1) detected; $^1$H-NMR (400 MHz, CDCl3) d 7.68 (d, 2H), 7.49-7.51 (m, 3H), 7.36 (d, 1H), 7.30 (dd, 1H), 6.83 (s, 1H), 3.47 (br s, 4H), 3.13 (br s, 3H), 3.05 (br s, 3H), 2.81 (s, 2H), 1.62-1.72 (m, 4H), 0.93 (t, 6H).

The following examples 125 and 126 were prepared by the procedures as described in Example 124 (Steps F and G) using tert-butyl (1E,4E)-8-bromo-4-(dipropylcarbamoyl)-3H-benzo[b]azepin-2-ylcarbamate and the appropriate boronic acids.

Example 125

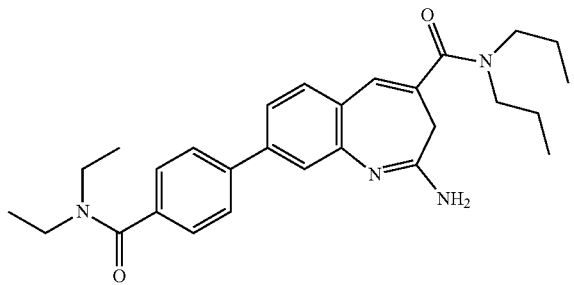 [SMILES: CCCN(CCC)C(=O)C1=Cc2ccc(-c3ccc(C(=O)N(CC)CC)cc3)cc2N=C(N)C1]

(1E,4E)-2-amino-8-(4-(diethylcarbamoyl)phenyl)-N,N-dipropyl-3H-benzo[b]azepine-4-carboxamide MS APCI (+) m/z 461 (M+1) detected; $^1$H-NMR (400 MHz, CDCl$_3$) δ 7.68 (d, 2H), 7.50 (d, 1H), 7.45 (d, 2H), 7.36 (d, 1H), 7.30 (dd, 1H), 6.83 (s, 1H), 3.56 (br s, 2H), 3.47 (br s, 4H), 3.33 (br s, 2H), 2.81 (s, 2H), 1.62-1.72 (m, 4H), 1.25 (br s, 3H), 1.17 (br s, 3H), 0.93 (t, 6H).

Example 126

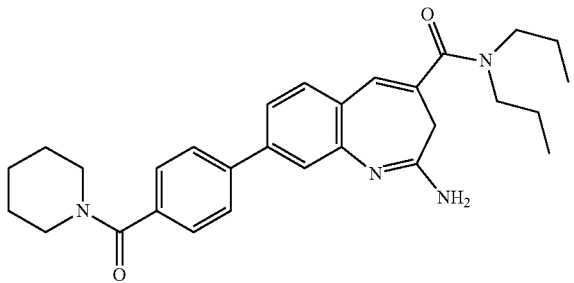 [SMILES: CCCN(CCC)C(=O)C1=Cc2ccc(-c3ccc(C(=O)N4CCCCC4)cc3)cc2N=C(N)C1]

(1E,4E)-2-amino-8-(4-(piperidine-1-carbonyl)phenyl)-N,N-dipropyl-3H-benzo[b]azepine-4-carboxamide MS APCI (+) m/z 473 (M+1) detected; $^1$H-NMR (400 MHz, CDCl$_3$) δ 7.68 (d, 2H), 7.46-7.50 (m, 3H), 7.36 (d, 1H), 7.29 (dd, 1H), 6.83 (s, 1H), 3.73 (br s, 2H), 3.47 (br s, 6H), 2.81 (s, 2H), 1.62-1.70 (m, 10H), 0.93 (t, 6H).

Example 127

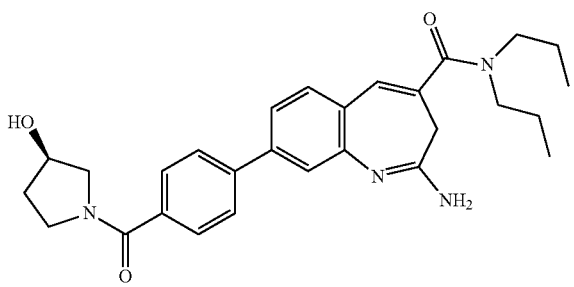 [SMILES: CCCN(CCC)C(=O)C1=Cc2ccc(-c3ccc(C(=O)N4CC[C@@H](O)C4)cc3)cc2N=C(N)C1]

(1E,4E)-2-amino-8-(4-((R)-3-hydroxypyrrolidine-1-carbonyl)phenyl)-N,N-dipropyl-3H-benzo[b]azepine-4-carboxamide Step A: Preparation of (R)-1-benzyl-3-(tert-butyldimethylsilyloxy)pyrrolidine The title compound was prepared by the procedure as described in Example 112 (Step A) using (R)-1-benzylpyrrolidin-3-ol.

Step B: Preparation of (R)-3-(tert-butyldimethylsilyloxy)pyrrolidine

The title compound was prepared by the procedure as described in Example 112 (Step B) using (R)-1-benzyl-3-(tert-butyldimethylsilyloxy)pyrrolidine.

Step C: Preparation of (R)-(3-(tert-butyldimethylsilyloxy)pyrrolidin-1-yl)(4-(4,4,5,5-tetramethyl-1,3,2-dioxaborolan-2-yl)phenyl)methanone The title compound was prepared by the procedure as described in Example 101 (Step H) using 4-(4,4,5,5-tetramethyl-1,3,2-dioxaborolan-2-yl)benzoic acid and (R)-3-(tert-butyldimethylsilyloxy)pyrrolidine.

Step D: Preparation of tert-butyl (1E,4E)-8-(4-((R)-3-(tert-butyldimethylsilyloxy)pyrrolidine-1-carbonyl)phenyl)-4-(dipropylcarbamoyl)-3H-benzo[b]azepin-2-ylcarbamate The title compound was prepared by the procedure as described in Example 124 (Step F) using tert-butyl (1E,4E)-8-bromo-4-(dipropylcarbamoyl)-3H-benzo[b]azepin-2-ylcarbamate and (R)-(3-(tert-butyldimethylsilyloxy)pyrrolidin-1-yl)(4-(4,4,5,5-tetramethyl-1,3-dioxolan-2-yl)phenyl)methanone. MS APCI (+) m/z 689 (M+1) detected.

Step E: Preparation of tert-butyl (1E,4E)-4-(dipropylcarbamoyl)-8-(4-((R)-3-hydroxypyrrolidine-1-carbonyl)phenyl)-3H-benzo[b]azepin-2-ylcarbamate To a solution of tert-butyl (1E,4E)-8-(4-((R)-3-(tert-butyldimethylsilyloxy)pyrrolidine-1-carbonyl)phenyl)-4-(dipropylcarbamoyl)-3H-benzo[b]azepin-2-ylcarbamate (225 mg, 0.327 mmol) in THF (4 mL) at 0° C. was added a solution of TBAF (0.34 mL, 0.34 mmol, 1 M solution in THF). The resulting mixture was warmed to room temperature and stirred for 1.5 hr. The reaction mixture was diluted with EtOAc and washed with brine (2×). The organic layer was dried over MgSO$_4$, filtered, and concentrated under reduced pressure to give the crude tert-butyl (1E,4E)-4-(dipropylcarbamoyl)-8-(4-((R)-3-hydroxypyrrolidine-1-carbonyl)phenyl)-3H-benzo[b]azepin-2-ylcarbamate that was used directly without further purification. MS APCI (+) m/z 575 (M+1) detected.

Step F: Preparation of (1E,4E)-2-amino-8-(4-((R)-3-hydroxypyrrolidine-1-carbonyl)phenyl)-N,N-dipropyl-3H-benzo[b]azepine-4-carboxamide The title compound was prepared by the procedure as described in Example 101 (Step I) using tert-butyl (1E,4E)-4-(dipropylcarbamoyl)-8-(4-((R)-3-hydroxypyrrolidine-1-carbonyl)phenyl)-3H-benzo[b]azepin-2-ylcarbamate. MS APCI (+) m/z 475 (M+1) detected; $^1$H-NMR (400 MHz, CDCl$_3$) d 7.53-7.65 (m, 5H), 7.33-7.38 (m, 2H), 6.84 (s, 1H), 4.60 (br s, 0.5H), 4.47 (br s, 0.5H), 3.45-3.83 (m, 8H), 2.92 (s, 2H), 1.99-2.12 (m, 2H), 1.62-1.71 (m, 4H), 0.93 (t, 6H).

Example 128

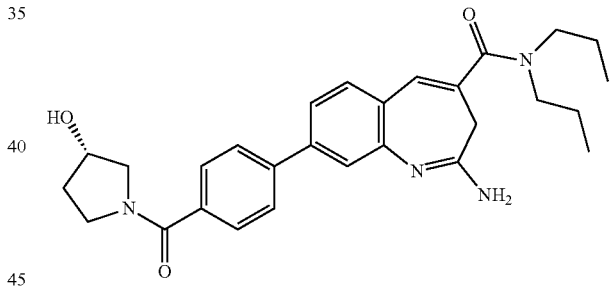

(1E,4E)-2-amino-8-(4-((S)-3-hydroxypyrrolidine-1-carbonyl)phenyl)-N,N-dipropyl-3H-benzo[b]azepine-4-carboxamide The title compound was prepared by the procedures as described in Example 127 using tert-butyl (1E,4E)-8-bromo-4-(dipropylcarbamoyl)-3H-benzo[b]azepin-2-ylcarbamate and (S)-1-benzylpyrrolidin-3-ol. MS APCI (+) m/z 475 (M+1) detected; $^1$H-NMR (400 MHz, CDCl$_3$) 7.53-7.66 (m, 5H), 7.32-7.38 (m, 2H), 6.84 (s, 1H), 4.60 (br s, 0.5H), 4.47 (br s, 0.5H), 3.46-3.84 (m, 8H), 2.88 (s, 2H), 1.99-2.11 (m, 2H), 1.62-1.71 (m, 4H), 0.93 (t, 6H).

The following examples 129 and 130 were prepared by the procedures as described in Example 124 (Step F) and Example 101 (Step I) using tert-butyl (1E,4E)-8-bromo-4-(dipropylcarbamoyl)-3H-benzo[b]azepin-2-ylcarbamate and ((3S,4S)-3,4-dihydroxypyrrolidin-1-yl)(4-(4,4,5,5-tetramethyl-1,3-dioxolan-2-yl)phenyl)methanone or ((3R,4R)-3,4-dihydroxypyrrolidin-1-yl)(4-(4,4,5,5-tetramethyl-1,3-dioxolan-2-yl)phenyl)methanone.

Example 129

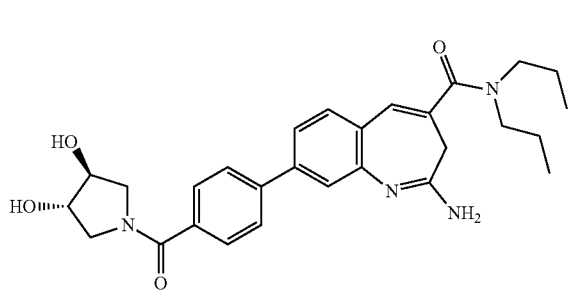 [SMILES: CCCN(CCC)C(=O)C1=Cc2ccc(-c3ccc(C(=O)N4C[C@H](O)[C@@H](O)C4)cc3)cc2N=C(N)C1]

(1E,4E)-2-amino-8-(4-((3S,4S)-3,4-dihydroxypyrrolidine-1-carbonyl)phenyl)-N,N-dipropyl-3H-benzo[b]azepine-4-carboxamide

Step A: Preparation of (3S,4S)-pyrrolidine-3,4-diol

The title compound was prepared by the procedure as described in Example 112 (Step B) using (3S,4S)-1-benzylpyrrolidine-3,4-diol.

Step B: Preparation of ((3S,4S)-3,4-dihydroxypyrrolidin-1-yl)(4-(4,4,5,5-tetramethyl-1,3,2-dioxaborolan-2-yl)phenyl)methanone The title compound was prepared by the procedure as described in Example 101 (Step H) using 4-(4,4,5,5-tetramethyl-1,3,2-dioxaborolan-2-yl)benzoic acid and (3S,4S)-pyrrolidine-3,4-diol.

Step C: Preparation of tert-butyl (1E,4E)-8-(4-((3S,4S)-3,4-dihydroxypyrrolidine-1-carbonyl)phenyl)-4-(dipropylcarbamoyl)-3H-benzo[b]azepin-2-ylcarbamate The title compound was prepared by the procedure as described in Example 124 (Step F) using tert-butyl (1E,4E)-8-bromo-4-(dipropylcarbamoyl)-3H-benzo[b]azepin-2-ylcarbamate and ((3S,4S)-3,4-dihydroxypyrrolidin-1-yl)(4-(4,4,5,5-tetramethyl-1,3,2-dioxaborolan-2-yl)phenyl)methanone. MS APCI (+) m/z 591 (M+1) detected

Step D: Preparation of (1E,4E)-2-amino-8-(4-((3S,4S)-3,4-dihydroxypyrrolidine-1-carbonyl)phenyl)-N,N-dipropyl-3H-benzo[b]azepine-4-carboxamide The title compound was prepared by the procedure as described in Example 109 (Step C) using tert-butyl (1E,4E)-8-(4-((3S,4S)-3,4-dihydroxypyrrolidine-1-carbonyl)phenyl)-4-(dipropylcarbamoyl)-3H-benzo[b]azepin-2-ylcarbamate: MS APCI (+) m/z 491 (M+1) detected; $^1$H-NMR (400 MHz, CDCl$_3$) d 7.65 (d, 2H), 7.57 (d, 2H), 7.47 (s, 1H), 7.34 (d, 1H), 7.27-7.29 (m, 1H), 6.82 (s, 1H), 4.28 (s, 1H), 4.18 (s, 1H), 3.97-4.00 (m, 1H), 3.85-3.87 (m, 1H), 3.66 (d, 1H), 3.46 (br s, 5H), 2.81 (s, 2H), 1.62-1.71 (m, 4H), 0.93 (t, 6H).

Example 130

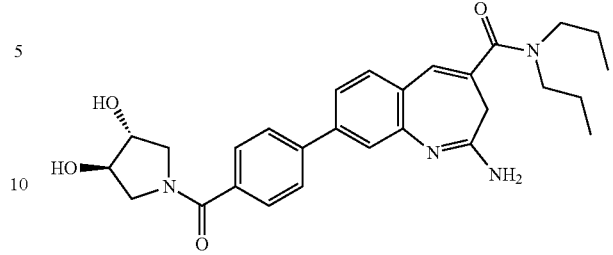

(1E,4E)-2-amino-8-(4-((3R,4R)-3,4-dihydroxypyrrolidine-1-carbonyl)phenyl)-N,N-dipropyl-3H-benzo[b]azepine-4-carboxamide The title compound was prepared by the procedures as described in Example 129 using tert-butyl (1E,4E)-8-bromo-4-(dipropylcarbamoyl)-3H-benzo[b]azepin-2-ylcarbamate and (3R,4R)-1-benzylpyrrolidine-3,4-diol. MS APCI (+) m/z 491 (M+1) detected; $^1$H-NMR (400 MHz, CDCl$_3$) d 7.62 (d, 2H), 7.54 (d, 2H), 7.45 (s, 1H), 7.32 (d, 1H), 7.24 (d, 1H), 6.80 (s, 1H), 4.25 (s, 1H), 4.14 (s, 1H), 3.94-3.96 (m, 1H), 3.81-3.83 (m, 1H), 3.63 (d, 1H), 3.44 (br s, 5H), 2.79 (s, 2H), 1.62-1.68 (m, 4H), 0.92 (t, 6H).

Example 133

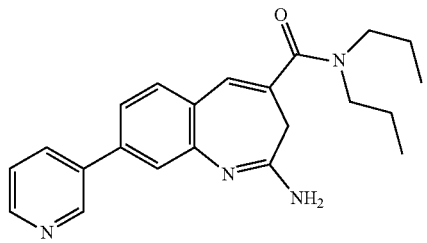 [SMILES: CCCN(CCC)C(=O)C1=Cc2ccc(-c3cccnc3)cc2N=C(N)C1]

(1E,4E)-2-amino-N,N-dipropyl-8-(pyridin-3-yl)-3H-benzo[b]azepine-4-carboxamide

MS APCI (+) m/z 363 (M+1) detected; $^1$H-NMR (400 MHz, CDCl$_3$) δ 8.91 (d, 1H), 8.59 (dd, 1H), 7.94 (dt, 1H), 7.49 (d, 1H), 7.35-7.40 (m, 2H), 7.29 (dd, 1H), 6.84 (s, 1H), 3.47 (br s, 4H), 2.81 (s, 2H), 1.63-1.72 (m, 4H), 0.94 (m, 6H).

Example 134

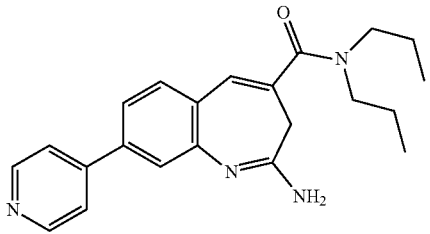 [SMILES: CCCN(CCC)C(=O)C1=Cc2ccc(-c3ccncc3)cc2N=C(N)C1]

(1E,4E)-2-amino-N,N-dipropyl-8-(pyridin-4-yl)-3H-benzo[b]azepine-4-carboxamide

MS APCI (−) m/z 361 (M−1) detected; $^1$H-NMR (400 MHz, CDCl$_3$) δ 8.66 (d, 2H), 7.55-7.57 (m, 3H), 7.39 (d, 1H), 7.33 (dd, 1H), 6.84 (s, 1H), 3.47 (br s, 4H), 2.81 (s, 2H), 1.63-1.72 (m, 4H), 0.94 (m, 6H).

Example 135

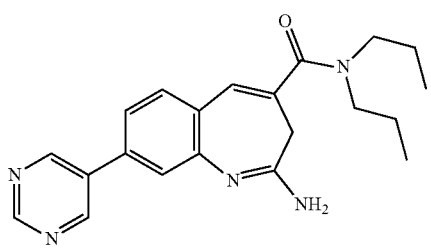 [SMILES: CCCN(CCC)C(=O)C1=Cc2ccc(-c3cncnc3)cc2N=C(N)C1]

(1E,4E)-2-amino-N,N-dipropyl-8-(pyrimidin-5-yl)-3H-benzo[b]azepine-4-carboxamide Step A: Preparation of (1E,4E)-2-amino-8-bromo-N,N-dipropyl-3H-benzo[b]azepine-4-carboxamide The title compound was prepared by the procedures as described in Example 101 (Step I) using tert-butyl (1E,4E)-8-bromo-4-(dipropylcarbamoyl)-3H-benzo[b]azepin-2-ylcarbamate. MS APCI (+) m/z 364, 366 (M+1, Br pattern) detected Step B: Preparation of (1E,4E)-2-amino-N,N-dipropyl-8-(pyrimidin-5-yl)-3H-benzo[b]azepine-4-carboxamide The title compound was prepared by the procedure as described in Example 124 (Step F) using (1E,4E)-2-amino-8-bromo-N,N-dipropyl-3H-benzo[b]azepine-4-carboxamide, pyrimidin-5-ylboronic acid, and sodium 2'-(dicyclohexylphosphino)-2,6-dimethoxybiphenyl-3-sulfonate in $H_2O$-MeCN. MS APCI (+) m/z 364 (M+1) detected; $^1$H-NMR (400 MHz, $CDCl_3$) d 9.21 (s, 1H), 9.01 (s, 2H), 7.50 (s, 1H), 7.43 (d, 1H), 7.27-7.29 (m, 1H), 6.84 (s, 1H), 3.47 (br s, 4H), 2.84 (s, 2H), 1.63-1.72 (m, 4H), 0.94 (t, 6H).

Example 136

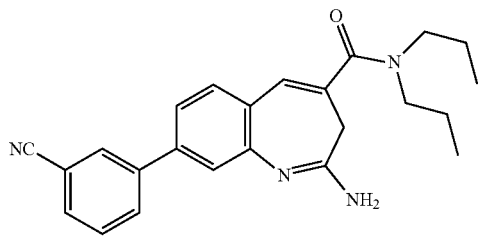 [SMILES: CCCN(CCC)C(=O)C1=Cc2ccc(-c3cccc(C#N)c3)cc2N=C(N)C1]

(1E,4E)-2-amino-8-(3-cyanophenyl)-N,N-dipropyl-3H-benzo[b]azepine-4-carboxamide

The title compound was prepared by the procedure as described in Example 124 (Step F) using (1E,4E)-2-amino-8-bromo-N,N-dipropyl-3H-benzo[b]azepine-4-carboxamide and 3-cyanophenylboronic acid. MS APCI (+) m/z 387 (M+1) detected; $^1$H-NMR (400 MHz, $CDCl_3$) d 7.91 (m, 1H), 7.87-7.89 (m, 1H), 7.63-7.65 (m, 1H), 7.55 (t, 1H), 7.51 (br s, 1H), 7.40 (d, 1H), 7.30 (dd, 1H), 6.85 (s, 1H), 3.46 (br s, 4H), 2.90 (s, 2H), 1.62-1.72 (m, 4H), 0.94 (t, 6H).

The following examples 137 and 138 were prepared by the procedures as described in Example 136 using (1E,4E)-2-amino-8-bromo-N,N-dipropyl-3H-benzo[b]azepine-4-carboxamide and 4-cyanophenylboronic acid or 3-(dimethylcarbamoyl)phenylboronic acid.

Example 137

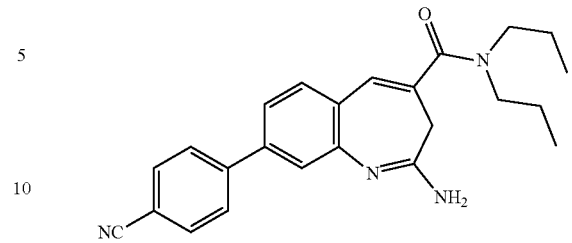

(1E,4E)-2-amino-8-(4-cyanophenyl)-N,N-dipropyl-3H-benzo[b]azepine-4-carboxamide

MS APCI (+) m/z 387 (M+1) detected; $^1$H-NMR (400 MHz, $CDCl_3$) δ 7.71-7.76 (m, 4H), 7.52 (s, 1H), 7.39 (d, 1H), 7.31 (d, 1H), 6.84 (s, 1H), 3.46 (br s, 4H), 2.86 (s, 2H), 1.62-1.72 (m, 4H), 0.93 (t, 6H).

Example 138

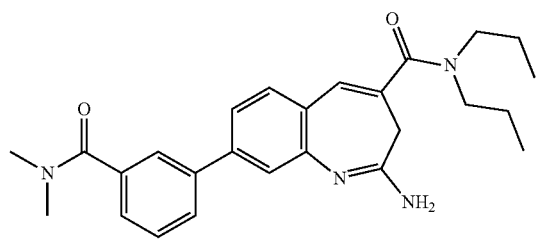 [SMILES: CCCN(CCC)C(=O)C1=Cc2ccc(-c3cccc(C(=O)N(C)C)c3)cc2N=C(N)C1]

(1E,4E)-2-amino-8-(3-(dimethylcarbamoyl)phenyl)-N,N-dipropyl-3H-benzo[b]azepine-4-carboxamide MS APCI (+) m/z 433 (M+1) detected; $^1$H-NMR (400 MHz, $CDCl_3$) δ 7.68-7.69 (m, 2H), 7.54 (br s, 1H), 7.46-7.50 (m, 1H), 7.40-7.42 (m, 1H), 7.37 (s, 2H), 6.85 (s, 1H), 3.46 (br s, 4H), 3.14 (br s, 3H), 3.03 (br s, 3H), 2.92 (s, 2H), 1.62-1.71 (m, 4H), 0.93 (t, 6H).

Example 139

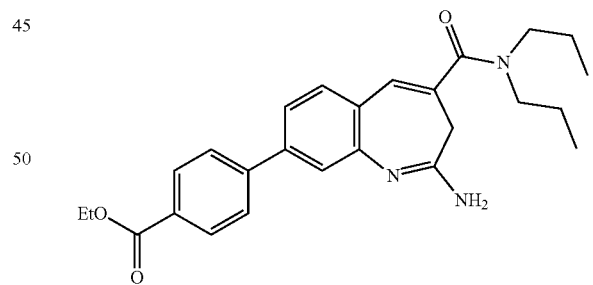

ethyl 4-((1E,4E)-2-amino-4-(dipropylcarbamoyl)-3H-benzo[b]azepin-8-yl)benzoate

The title compound was prepared by the procedures as described in Example 124 (Step F) and Example 101 (Step I) using tert-butyl (1E,4E)-8-bromo-4-(dipropylcarbamoyl)-3H-benzo[b]azepin-2-ylcarbamate and 4-(ethoxycarbonyl)phenylboronic acid. MS APCI (+) m/z 434 (M+1) detected; $^1$H-NMR (400 MHz, $CDCl_3$) δ 8.11 (d, 2H), 7.72 (d, 2H), 7.54 (d, 1H), 7.38 (d, 1H), 7.34 (dd, 1H), 6.84 (s, 1H), 4.40 (q, 2H), 3.47 (br s, 4H), 2.83 (s, 2H), 1.62-1.72 (m, 4H), 1.42 (t, 3H), 0.94 (t, 6H).

Example 141

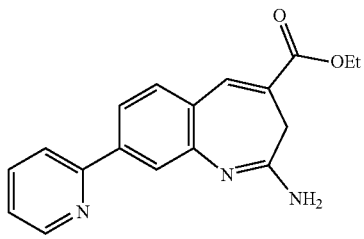 [SMILES: CCOC(=O)C1=Cc2ccc(-c3ccccn3)cc2N=C(N)C1]

(1E,4E)-ethyl 2-amino-8-(pyridin-2-yl)-3H-benzo[b]
azepine-4-carboxylate

Step A: Preparation of 2-nitro-4-(4,4,5,5-tetramethyl-1,3,2-dioxaborolan-2-yl)benzaldehyde The title compound was prepared by the procedure as described in Example 124 (Step F) using 4-bromo-2-nitrobenzaldehyde, bis(pinacolato)diboron, tris(dibenzylidineacetone)dipalladium(0), PCy$_3$, and KOAc in dioxane (reflux).

Step B: Preparation of
2-nitro-4-(pyridin-2-yl)benzaldehyde

The title compound was prepared by the procedure as described in Example 101 (Step C) using 2-nitro-4-(4,4,5,5-tetramethyl-1,3,2-dioxaborolan-2-yl)benzaldehyde and 2-bromopyridine in dioxane (reflux).

Step C: Preparation of (E)-ethyl 2-(cyanomethyl)-3-(2-nitro-4-(pyridin-2-yl)phenyl)acrylate The title compound was prepared by the procedure as described in Example 101 (Step D) using 2-nitro-4-(pyridin-2-yl)benzaldehyde and a-cyanomethylcarboethoxyethylidene triphenylphosphorane.

Step D: Preparation of (1E,4E)-ethyl 2-amino-8-(pyridin-2-yl)-3H-benzo[b]azepine-4-carboxylate The title compound was prepared by the procedure as described in Example 101 (Step E) using (E)-ethyl 2-(cyanomethyl)-3-(2-nitro-4-(pyridin-2-yl)phenyl)acrylate. MS APCI (+) m/z 308 (M+1) detected; $^1$H-NMR (400 MHz, CDCl$_3$) δ 8.70 (d, 1H), 7.85 (s, 1H), 7.73-7.81 (m, 4H), 7.50 (d, 1H), 7.23-7.26 (m, 1H), 4.32 (q, 2H), 2.98 (s, 2H), 1.38 (t, 3H).

The following examples 142 and 143 were prepared by the procedures as described in Example 101 (Steps C, D, and E) using 4-bromo-2-nitrobenzaldehyde and pyridin-3-ylboronic acid or pyridin-4-ylboronic acid.

Example 142

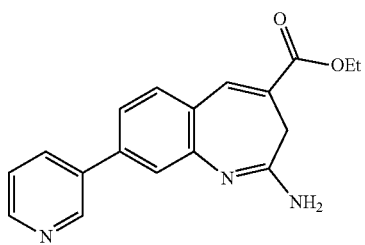 [SMILES: CCOC(=O)C1=Cc2ccc(-c3cccnc3)cc2N=C(N)C1]

(1E,4E)-ethyl 2-amino-8-(pyridin-3-yl)-3H-benzo[b]
azepine-4-carboxylate

MS APCI (+) m/z 308 (M+1) detected; $^1$H-NMR (400 MHz, d$_6$-DMSO) δ 8.92 (s, 1H), 8.58 (d, 1H), 8.11 (d, 1H), 7.80 (2, 1H), 7.58 (d, 1H), 7.49 (dd, 1H), 7.36-7.38 (m, 2H), 4.26 (q, 2H), 2.98 (s, 2H), 1.32 (t, 3H).

Example 143

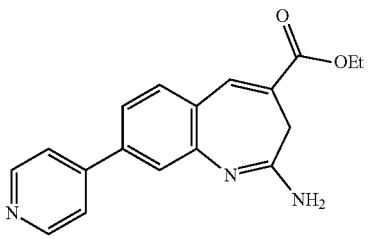 [SMILES: CCOC(=O)C1=Cc2ccc(-c3ccncc3)cc2N=C(N)C1]

(1E,4E)-ethyl 2-amino-8-(pyridin-4-yl)-3H-benzo[b]
azepine-4-carboxylate

MS APCI (+) m/z 308 (M+1) detected; $^1$H-NMR (400 MHz, CDCl$_3$) δ 8.66-8.68 (m, 2H), 7.84 (s, 1H), 7.49-7.57 (m, 4H), 7.36 (dd, 1H), 4.33 (q, 2H), 2.99 (s, 2H), 1.39 (t, 3H).

Example 144

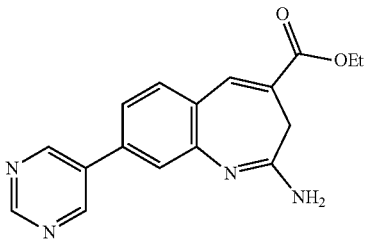 [SMILES: CCOC(=O)C1=Cc2ccc(-c3cncnc3)cc2N=C(N)C1]

(1E,4E)-ethyl 2-amino-8-(pyrimidin-5-yl)-3H-benzo
[b]azepine-4-carboxylate

The title compound was prepared by the procedure as described in Example 124 (Step F) using (1E,4E)-ethyl 2-amino-8-bromo-3H-benzo[b]azepine-4-carboxylate and pyrimidin-5-ylboronic acid. MS APCI (+) m/z 309 (M+1) detected; $^1$H-NMR (400 MHz, CDCl$_3$) δ 9.22 (s, 1H), 9.02 (s, 2H), 7.84 (s, 1H), 7.54 (d, 1H), 7.47 (d, 1H), 7.30 (dd, 1H), 4.34 (q, 2H), 2.99 (s, 2H), 1.40 (t, 3H).

Example 145

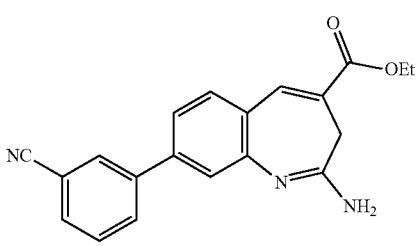 [SMILES: CCOC(=O)C1=Cc2ccc(-c3cccc(C#N)c3)cc2N=C(N)C1]

(1E,4E)-ethyl 2-amino-8-(3-cyanophenyl)-3H-benzo[b]azepine-4-carboxylate

Step A: Preparation of (1E,4E)-ethyl 2-(tert-butoxycarbonylamino)-8-(3-cyanophenyl)-3H-benzo[b]azepine-4-carboxylate A mixture of (1E,4E)-ethyl 8-bromo-2-(tert-butoxycarbonylamino)-3H-benzo[b]azepine-4-carboxylate (2.05 g, 5 mmol), 3-cyanophenylboronic acid (1.47 g, 10 mmol), CsF (2.28 g, 15 mmol), and Pd(PPh$_3$)$_4$ (0.345 g, 0.3 mmol) in anhydrous THF (100 mL) was refluxed for 12 h. After cooling to room temperature, the reaction mixture was poured into water and extracted with EtOAc. The combined organic layers were dried over Na$_2$SO$_4$, filtered, and concentrated under reduced pressure to give the crude material that was purified by silica gel flash column chromatography to afford 1.12 g (52%) of (1E,4E)-ethyl 2-(tert-butoxycarbonylamino)-8-(3-cyanophenyl)-3H-benzo[b]azepine-4-carboxylate.

Step B: Preparation of (1E,4E)-ethyl 2-amino-8-(3-cyanophenyl)-3H-benzo[b]azepine-4-carboxylate The title compound was prepared by the procedure as described in Example 101 (Step I) using (1E,4E)-ethyl 2-(tert-butoxycarbonylamino)-8-(3-cyanophenyl)-3H-benzo[b]azepine-4-carboxylate. MS APCI (+) m/z 332 (M+1) detected; $^1$H-NMR (400 MHz, d$_6$-DMSO) δ 8.17 (s, 1H), 8.04-8.06 (m, 1H), 7.82-7.84 (m, 1H), 7.78 (s, 1H), 7.67 (t, 1H), 7.54 (d, 1H), 7.33-7.37 (m, 2H), 6.93 (s, 2H), 4.25 (q, 2H), 2.92 (s, 2H), 1.31 (t, 3H).

The following examples 146 and 147 were prepared by the procedures as described in Example 145. In case of example 146, Cs$_2$CO$_3$ was used as a base for the Suzuki coupling.

Example 146

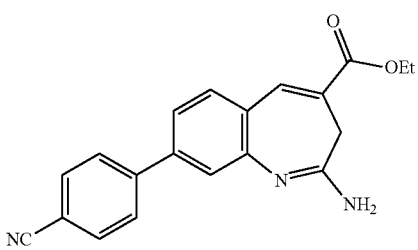 [SMILES: CCOC(=O)C1=Cc2ccc(-c3ccc(C#N)cc3)cc2N=C(N)C1]

(1E,4E)-ethyl 2-amino-8-(4-cyanophenyl)-3H-benzo[b]azepine-4-carboxylate

MS APCI (+) m/z 332 (M+1) detected; $^1$H-NMR (400 MHz, CDCl$_3$) δ 7.83 (s, 1H), 7.72-7.77 (m, 4H), 7.49 (d, 1H), 7.47 (d, 1H), 7.30 (dd, 1H), 4.33 (q, 2H), 2.98 (s, 2H), 1.39 (t, 3H).

Example 147

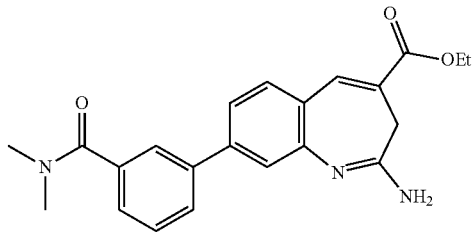 [SMILES: CCOC(=O)C1=Cc2ccc(-c3cccc(C(=O)N(C)C)c3)cc2N=C(N)C1]

(1E,4E)-ethyl 2-amino-8-(3-(dimethylcarbamoyl)phenyl)-3H-benzo[b]azepine-4-carboxylate MS APCI (+) m/z 378 (M+1) detected; $^1$H-NMR (400 MHz, CDCl$_3$) δ 7.83 (s, 1H), 7.69-7.71 (m, 2H), 7.45-7.50 (m, 3H), 7.40-7.42 (m, 1H), 7.32 (dd, 1H), 4.32 (q, 2H), 3.14 (br s, 3H), 3.02 (br s, 3H), 2.98 (s, 2H), 1.39 (t, 3H).

The following examples 154, 155, and 156 were prepared by the procedures as described in Example 101 (Steps C, D, and E) using 4-bromo-2-nitrobenzaldehyde and the appropriate boronic acids.

Example 154

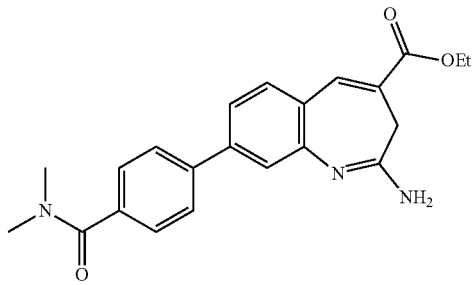 [SMILES: CCOC(=O)C1=Cc2ccc(-c3ccc(C(=O)N(C)C)cc3)cc2N=C(N)C1]

(1E,4E)-ethyl 2-amino-8-(4-(dimethylcarbamoyl)phenyl)-3H-benzo[b]azepine-4-carboxylate MS APCI (+) m/z 378 (M+1) detected; $^1$H-NMR (400 MHz, CDCl$_3$) δ 7.84 (s, 1H), 7.69 (d, 2H), 7.46-7.51 (m, 4H), 7.32 (dd, 1H), 4.32 (q, 2H), 3.14 (br s, 3H), 3.05 (br s, 3H), 2.98 (s, 2H), 1.39 (t, 3H).

Example 155

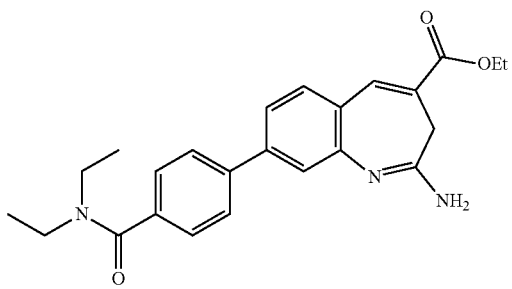 [SMILES: CCOC(=O)C1=Cc2ccc(-c3ccc(C(=O)N(CC)CC)cc3)cc2N=C(N)C1]

(1E,4E)-ethyl 2-amino-8-(4-(diethylcarbamoyl)phenyl)-3H-benzo[b]azepine-4-carboxylate MS APCI (+) m/z 406 (M+1) detected; $^1$H-NMR (400 MHz, CDCl$_3$) δ 7.84 (s, 1H), 7.68 (d, 2H), 7.44-7.49 (m, 4H), 7.32 (dd, 1H), 4.33 (q, 2H), 3.57 (br s, 2H), 3.33 (br s, 2H), 2.98 (s, 2H), 1.39 (t, 3H), 1.25 (br s, 3H), 1.17 (br s, 3H).

Example 156

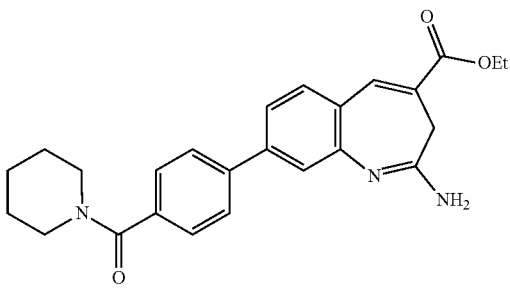 [SMILES: CCOC(=O)C1=Cc2ccc(-c3ccc(C(=O)N4CCCCC4)cc3)cc2N=C(N)C1]

(1E,4E)-ethyl 2-amino-8-(4-(piperidine-1-carbonyl)phenyl)-3H-benzo[b]azepine-4-carboxylate MS APCI (+) m/z 418 (M+1) detected; $^1$H-NMR (400 MHz, CDCl$_3$) δ 7.84 (s, 1H), 7.68 (d, 2H), 7.46-7.48 (m, 4H), 7.32 (dd, 1H), 4.33 (q, 2H), 3.73 (br s, 2H), 3.42 (br s, 2H), 2.98 (s, 2H), 1.62-1.70 (m, 6H), 1.39 (t, 3H).

Example 174

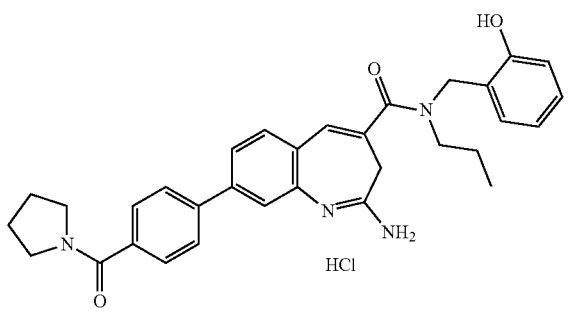 [SMILES: CCCN(Cc1ccccc1O)C(=O)C1=Cc2ccc(-c3ccc(C(=O)N4CCCC4)cc3)cc2N=C(N)C1 ; Cl]

(1E,4E)-2-amino-N-(2-hydroxybenzyl)-N-propyl-8-(4-(pyrrolidine-1-carbonyl)phenyl)-3H-benzo[b]azepine-4-carboxamide hydrochloride

Step A: Preparation of methyl 2-hydroxybenzoate

To a solution of 2-hydroxybenzoic acid (110 g, 796 mmol) in MeOH (400 mL) was bubbled HCl (gas) for 1 h. The resulting mixture was stirred at 50° C. overnight. The reaction mixture was cooled to room temperature and concentrated under reduced pressure to give the crude methyl 2-hydroxybenzoate that was used directly without further purification.

Step B: Preparation of 2-hydroxy-N-propylbenzamide

The crude methyl 2-hydroxybenzoate was dissolved in n-propylamine (400 mL). The reaction mixture in a sealed reactor was stirred at 80° C. overnight. The reaction mixture was concentrated under reduced pressure to give the crude material that was purified by silica gel flash column chromatography to afford 120 g (84%) of 2-hydroxy-N-propylbenzamide. LCMS ESI (+) m/z 180 (M+1) detected.

Step C: Preparation of tert-butyl 2-hydroxybenzyl(propyl)carbamate

To a solution of LiAlH$_4$ (35 g, 0.92 mol) in THF (500 mL) at 0° C. was added 2-hydroxy-N-propylbenzamide (66 g, 0.37 mol) in THF (200 mL) dropwise. The reaction mixture was heated at 80° C. overnight. The reaction mixture was quenched by addition of H$_2$O (300 mL) at 0° C. Then, Boc$_2$O (96.5 g, 0.44 mol) in THF (200 mL) was added dropwise. After stirring 5 h, sat'd aq NaHCO$_3$ (200 mL) was added. The aqueous layer was separated and extracted with EtOAc (2×300 mL). The combined organic layers were dried over MgSO$_4$, filtered, and concentrated under reduced pressure to give the crude material that was purified by silica gel flash column chromatography to afford 89 g (91%) of tert-butyl 2-hydroxybenzyl(propyl)carbamate.

Step D: Preparation of 2-((propylamino)methyl)phenol hydrochloride

A solution of tert-butyl 2-hydroxybenzyl(propyl)carbamate (89 g, 0.34 mol) in MeOH (400 mL) was bubbled with HCl gas. After stirring for 5 h at room temperature, the reaction mixture was concentrated under reduced pressure to afford 61 g (90%) of 2-((propylamino)methyl)phenol as HCl salt.

Step E: Preparation of tert-butyl (1E,4E)-4-((2-hydroxybenzyl)(propyl)carbamoyl)-8-(4-(pyrrolidine-1-carbonyl)phenyl)-3H-benzo[b]azepin-2-ylcarbamate The title compound was prepared by the procedure as described in Example 101 (Step H) using (1E,4E)-2-(tert-butoxycarbonylamino)-8-(4-(pyrrolidine-1-carbonyl)phenyl)-3H-benzo[b]azepine-4-carboxylic acid and 2-((propylamino)methyl)phenol hydrochloride.

Step F: Preparation of (1E,4E)-2-amino-N-(2-hydroxybenzyl)-N-propyl-8-(4-(pyrrolidine-1-carbonyl)phenyl)-3H-benzo[b]azepine-4-carboxamide hydrochloride A solution of the crude tert-butyl (1E,4E)-4-((2-hydroxybenzyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. The reaction mixture was concentrated under reduced pressure to give the crude material that was purified by silica gel flash column chromatography (EtOAc) to afford (1E,4E)-2-amino-N-(2-hydroxybenzyl)-N-propyl-8-(4-(pyrrolidine-1-carbonyl)phenyl)-3H-benzo[b]azepine-4-carboxamide as hydrochloride salt. MS APCI (+) m/z 523 (M+1) detected; 1H-NMR (400 MHz, d$_6$-DMSO) δ 9.68 (br s, 1H), 7.76 (d, 2H), 7.64 (d, 2H), 7.59 (br s, 3H), 7.10-7.14 (m, 2H), 7.03 (br s, 1H), 6.80-6.87 (m, 2H), 4.62 (br s, 2H), 3.44-3.49 (m, 6H), 3.19 (br s, 2H), 1.83-1.89 (m, 4H), 1.56-1.57 (m, 2H), 0.77-0.83 (m, 3H).

The following example, 176, was prepared by the procedures as described in Example 101 (Step H) and Example 178 (Step C) using (1E,4E)-2-(tert-butoxycarbonylamino)-8-(4-(pyrrolidine-1-carbonyl)phenyl)-3H-benzo[b]azepine-4-carboxylic acid and N-(2-(propylamino)ethyl)methanesulfonamide or 3-(propylamino)propane-1-sulfonamide.

Example 176

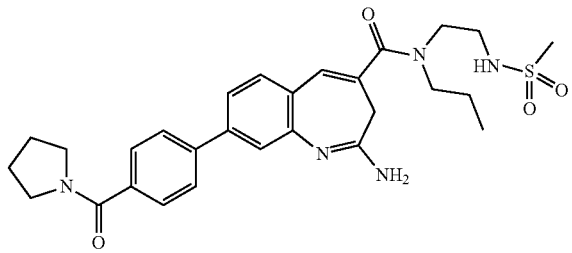 [SMILES: CCCN(CCNS(C)(=O)=O)C(=O)C1=Cc2ccc(-c3ccc(C(=O)N4CCCC4)cc3)cc2N=C(N)C1]

(1E,4E)-2-amino-N-(2-(methylsulfonamido)ethyl)-N-propyl-8-(4-(pyrrolidine-1-carbonyl)phenyl)-3H-benzo[b]azepine-4-carboxamide MS APCI (+) m/z 538 (M+1) detected; $^1$H-NMR (400 MHz, CDCl$_3$) δ 7.67 (d, 2H), 7.60 (d, 2H), 7.47 (s, 1H), 7.35 (d, 1H), 7.28 (dd, 1H), 6.86 (s, 1H), 3.66-3.69 (m, 4H), 3.51 (t, 2H), 3.42 (t, 4H), 2.90 (s, 5H), 1.89-2.00 (m, 4H), 1.60-1.68 (m, 2H), 0.87 (t, 3H).

Example 178

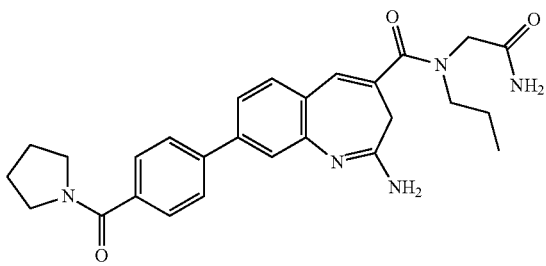 [SMILES: CCCN(CC(N)=O)C(=O)C1=Cc2ccc(-c3ccc(C(=O)N4CCCC4)cc3)cc2N=C(N)C1]

(1E,4E)-2-amino-N-(2-amino-2-oxoethyl)-N-propyl-8-(4-(pyrrolidine-1-carbonyl)phenyl)-3H-benzo[b]azepine-4-carboxamide Step A: Preparation of 2-(propylamino)acetamide hydrochloride To a solution of propan-1-amine (236 g, 3.99 mol) in acetonitrile (100 mL) at 0° C. was added a solution of 2-chloroacetamide (93.6 g, 1.00 mol) in acetonitrile (1500 mL) over 3 h. The resulting mixture was warmed to room temperature and stirred overnight. The reaction mixture was concentrated under reduced pressure to give the crude material that was purified by re-crystallization (MeOH and CH$_2$Cl$_2$) to afford 80 g (69%) of 2-(propylamino)acetamide as HCl salt. LCMS ESI (+) m/z 117 (M+1) detected.

Step B: Preparation of tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate The title compound was prepared by the procedures as described in Example 101 (Step H) using (1E,4E)-2-(tert-butoxycarbonylamino)-8-(4-(pyrrolidine-1-carbonyl)phenyl)-3H-benzo[b]azepine-4-carboxylic acid and 2-(propylamino)acetamide hydrochloride.

Step C: Preparation of (1E,4E)-2-amino-N-(2-amino-2-oxoethyl)-N-propyl-8-(4-(pyrrolidine-1-carbonyl)phenyl)-3H-benzo[b]azepine-4-carboxamide A solution of the crude tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. To this mixture was added saturated NaHCO$_3$ at 0° C. The aqueous layer was separated and extracted with CH$_2$Cl$_2$. The combined organic layers were dried over Na$_2$SO$_4$, filtered, and concentrated under reduced pressure to give the crude compound that was purified by silica gel flash column chromatography (MeOH:CH$_2$Cl$_2$=1:50) to afford 225 mg (45%) of (1E,4E)-2-amino-N-(2-amino-2-oxoethyl)-N-propyl-8-(4-(pyrrolidine-1-carbonyl)phenyl)-3H-benzo[b]azepine-4-carboxamide. MS APCI (+) m/z 474 (M+1) detected; $^1$H-NMR (400 MHz, CDCl$_3$) d 7.67 (d, 2H), 7.60 (d, 2H), 7.50 (br s, 1H), 7.30-7.36 (m, 2H), 6.93 (s, 1H), 4.11 (s, 2H), 3.67 (t, 2H), 3.58 (br s, 2H), 3.50 (t, 2H), 2.87 (s, 2H), 1.89-2.00 (m, 4H), 1.69-1.74 (m, 2H), 0.93 (t, 3H).

Example 182

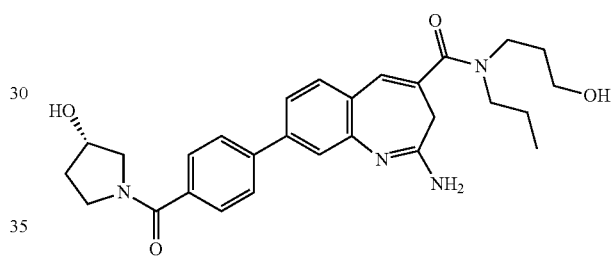

(1E,4E)-2-amino-N-(3-hydroxypropyl)-8-(4-((S)-3-hydroxypyrrolidine-1-carbonyl)phenyl)-N-propyl-3H-benzo[b]azepine-4-carboxamide Step A: Preparation of tert-butyl (1E,4E)-8-bromo-4-((3-(tert-butyldimethylsilyloxy)propyl)(propyl)carbamoyl)-3H-benzo[b]azepin-2-ylcarbamate The title compound was prepared by the procedure as described in Example 101 (Step H) using (1E,4E)-8-bromo-2-(tert-butoxycarbonylamino)-3H-benzo[b]azepine-4-carboxylic acid and 3-(tert-butyldimethylsilyloxy)-N-propylpropan-1-amine. MS APCI (+) m/z 594, 596 (M+1, Br pattern) detected.

Step B: Preparation of tert-butyl (1E,4E)-4-((3-(tert-butyldimethylsilyloxy)propyl)(carbamoyl)-8-(4-((S)-3-hydroxypyrrolidine-1-carbonyl)phenyl)-3H-benzo[b]azepin-2-ylcarbamate The title compound was prepared by the procedure as described in Example 124 (Step F) using tert-butyl (1E,4E)-8-bromo-4-((3-(tert-butyldimethylsilyloxy)propyl)(propyl)carbamoyl)-3H-benzo[b]azepin-2-ylcarbamate and (S)-(3-hydroxypyrrolidin-1-yl)(4-(4,4,5,5-tetramethyl-1,3,2-dioxaborolan-2-yl)phenyl)methanone that was prepared by the procedure as described in Example 101 (Step H) using 4-(4,4,5,5-tetramethyl-1,3,2-dioxaborolan-2-yl)benzoic acid and (S)-pyrrolidin-3-ol. MS APCI (+) m/z 705 (M+1) detected.

Step C: Preparation of (1E,4E)-2-amino-N-(3-hydroxypropyl)-8-(4-((S)-3-hydroxypyrrolidine-1-carbonyl)phenyl)-N-propyl-3H-benzo[b]azepine-4-carboxamide The title compound was prepared by the procedure as described in Example 109 (Step C) using tert-butyl (1E,4E)-4-((3-(tert-butyldimethylsilyloxy)propyl)(propyl)carbamoyl)-8-(4-((S)-3-hydroxypyrrolidine-1-carbonyl)phenyl)-3H-benzo[b]azepin-2-ylcarbamate. MS APCI (+) m/z 491 (M+1) detected; $^1$H-NMR (400 MHz, CDCl$_3$) d 7.59-7.66 (m, 4H), 7.50 (s, 1H), 7.36 (d, 1H), 7.31 (d, 1H), 6.88 (s, 1H), 4.61 (br s, 0.5H), 4.48 (br s, 0.5H), 3.75-3.84 (m, 2H), 3.62-3.70 (m, 6H), 3.46-3.50 (m, 2H), 2.84 (s, 2H), 1.96-2.15 (m, 4H), 1.82-1.87 (m, 2H), 1.65-1.72 (m, 2H), 0.93 (t, 3H).

Example 186

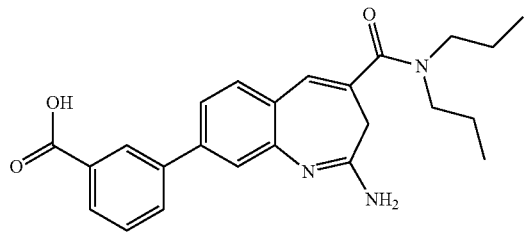 [SMILES: CCCN(CCC)C(=O)C1=Cc2ccc(-c3cccc(C(=O)O)c3)cc2N=C(N)C1]

3-((1E,4E)-2-amino-4-(dipropylcarbamoyl)-3H-benzo[b]azepin-8-yl)benzoic acid

Step A: Benzyl 3-((1E,4E)-2-amino-4-(dipropylcarbamoyl)-3H-benzo[b]azepin-8-yl)benzoate (52%) was prepared according to Example 206, Step B, substituting 3-(benzyloxycarbonyl)phenylboronic acid for 4-(methoxycarbonyl)phenylboronic acid. m/z (APCI-pos) M+1=496.2.

Step B: 3-((1E,4E)-2-amino-4-(dipropylcarbamoyl)-3H-benzo[b]azepin-8-yl)benzoic acid (61%) was prepared according to Example 188, Step B, substituting benzyl 3-((1E,4E)-2-amino-4-(dipropylcarbamoyl)-3H-benzo[b]azepin-8-yl)benzoate for benzyl 4-((1E,4E)-2-amino-4-(dipropylcarbamoyl)-3H-benzo[b]azepin-8-yl)benzoate. $^1$H NMR (400 MHz, DMSO-d$_6$) δ 8.37-8.42 (m, 1H), 8.00-8.06 (m, 1H), 7.81-7.87 (m, 1H), 7.68-7.73 (m, 1H), 7.51-7.63 (m, 3H), 6.96 (s, 1H), 3.51 (s, 2H), 3.15-3.41 (m, 4H, partially obscured by water peak), 1.53-1.68 (m, 4H), 0.75-0.94 (m, 6H); m/z (APCI-pos) M+1=406.2.

Example 187

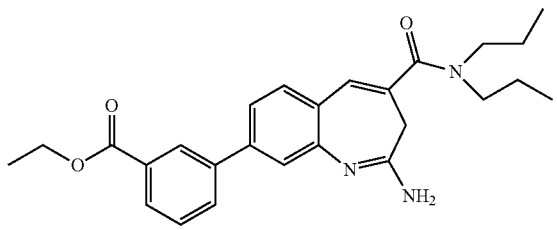 [SMILES: CCCN(CCC)C(=O)C1=Cc2ccc(-c3cccc(C(=O)OCC)c3)cc2N=C(N)C1]

Ethyl 3-((1E,4E)-2-amino-4-(dipropylcarbamoyl)-3H-benzo[b]azepin-8-yl)benzoate

Step A: Ethyl 3-((1E,4E)-2-amino-4-(dipropylcarbamoyl)-3H-benzo[b]azepin-8-yl)benzoate (45%) was prepared according to Example 206, Step B, substituting 3-(methoxycarbonyl)phenylboronic acid for 4-(methoxycarbonyl)phenylboronic acid. $^1$H NMR (400 MHz, CDCl$_3$) δ 8.34-8.37 (m, 1H), 8.02-8.05 (m, 1H), 7.82-7.86 (m, 1H), 7.49-7.55 (m, 2H), 7.33-7.39 (m, 2H), 6.84 (s, 1H), 5.17 (br s, 1H), 4.37-4.45 (m, 2H), 3.36-3.55 (m, 4H), 2.84 (s, 2H), 1.62-1.72 (m, 4H), 1.38-1.45 (m, 3H), 0.89-0.98 (m, 6H); m/z (APCI-pos) M+1=434.3.

Example 188

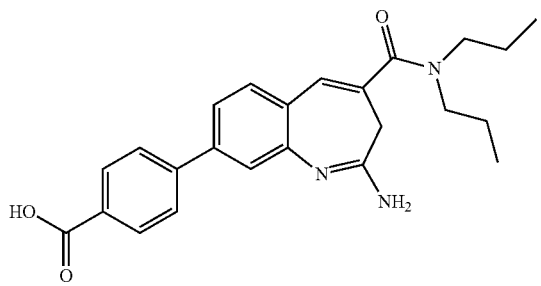 [SMILES: CCCN(CCC)C(=O)C1=Cc2ccc(-c3ccc(C(=O)O)cc3)cc2N=C(N)C1]

4-((1E,4E)-2-amino-4-(dipropylcarbamoyl)-3H-benzo[b]azepin-8-yl)benzoic acid

Step A: Benzyl 4-((1E,4E)-2-amino-4-(dipropylcarbamoyl)-3H-benzo[b]azepin-8-yl)benzoate (31%) was prepared according to Example 206, Step B, substituting 4-(benzyloxycarbonyl)phenylboronic acid for 4-(methoxycarbonyl)phenylboronic acid. m/z (APCI-pos) M+1=496.2.

Step B: Benzyl 4-((1E,4E)-2-amino-4-(dipropylcarbamoyl)-3H-benzo[b]azepin-8-yl)benzoate (0.025 g, 0.0504 mmol) was suspended in 1 ml of methanol, and 25 mgs of 10% Pd/C (Degussa type) was added and the mixture was hydrogenated under a balloon of hydrogen for one hour. This mixture was then filtered through GF/F filter paper, and the filtrate was concentrated to 16 mgs of 4-((1E,4E)-2-amino-4-(dipropylcarbamoyl)-3H-benzo[b]azepin-8-yl)benzoic acid (78%). $^1$H-NMR (400 MHz, DMSO-d$_6$) δ 7.98-8.03 (m, 2H), 7.76-7.82 (m, 2H), 7.38-7.43 (m, 1H), 7.33-7.37 (m, 1H), 7.27-7.31 (m, 1H), 6.92 (br s, 1H), 6.76 (s, 1H), 3.28-3.36 (m, 4H, partially obscured by water peak), 2.74 (s, 2H), 1.51-1.62 (m, 4H), 0.71-0.97 (m, 6H); m/z (APCI-pos) M+1=406.2.

Example 190

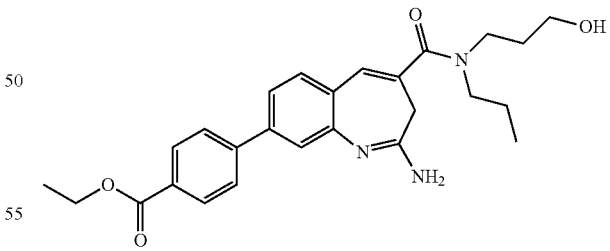

Ethyl 4-((1E,4E)-2-amino-4-((3-hydroxypropyl)(propyl)carbamoyl)-3H-benzo[b]azepin-8-yl)benzoate Step A: Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared according to Example 206, Step B, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]

azepine-4-carboxamide and 4-(ethoxycarbonyl)phenylboronic acid for 4-(methoxycarbonyl)phenylboronic acid. m/z (APCI-pos) M+1=664.0

Step B: Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) afforded 0.012 g (35%) of ethyl 4-((1E,4E)-2-amino-4-((3-hydroxypropyl)(propyl)carbamoyl)-3H-benzo[b]azepin-8-yl)benzoate. $^1$H NMR (400 MHz, CDCl$_3$) δ 8.08-8.14 (m, 2H), 7.69-7.74 (m, 2H), 7.52-7.55 (m, 1H), 7.32-7.40 (m, 2H), 6.89 (s, 1H), 4.35-4.44 (m, 2H), 3.58-3.71 (m, 5H), 3.45-3.53 (m, 2H), 2.85 (s, 2H), 1.81-1.88 (m, 2H), 1.64-1.77 (m, 2H), 1.36-1.44 (m, 3H), 0.90-0.97 (m, 3H); m/z (APCI-pos) M+1=450.2.

Example 194

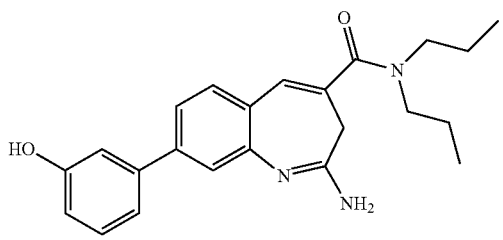 [SMILES: CCCN(CCC)C(=O)C1=Cc2ccc(-c3cccc(O)c3)cc2N=C(N)C1]

(1E,4E)-2-amino-8-(3-hydroxyphenyl)-N,N-dipropyl-3H-benzo[b]azepine-4-carboxamide Step A: (1E,4E)-2-amino-8-(3-hydroxyphenyl)-N,N-dipropyl-3H-benzo[b]azepine-4-carboxamide (39%) was prepared according to Example 206, Step B, substituting 3-hydroxyphenylboronic acid for 4-(methoxycarbonyl)phenylboronic acid. $^1$H NMR (400 MHz, CDCl$_3$) δ 7.59-7.64 (m, 1H), 7.24-7.38 (m, 4H), 7.08-7.14 (m, 1H), 6.81-6.86 (m, 2H), 5.10 (br s, 2H), 3.35-3.35 (m, 4H), 2.86 (s, 2H), 1.58-1.71 (m. 4H), 0.80-0.98 (m, 6H); m/z (APCI-pos) M+1=378.2.

Example 195

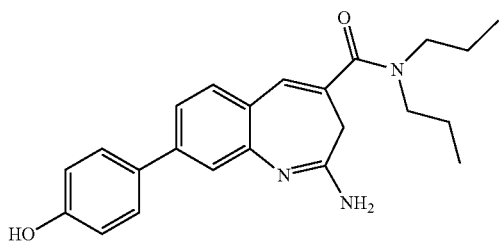 [SMILES: CCCN(CCC)C(=O)C1=Cc2ccc(-c3ccc(O)cc3)cc2N=C(N)C1]

(1E,4E)-2-amino-8-(4-hydroxyphenyl)-N,N-dipropyl-3H-benzo[b]azepine-4-carboxamide Step A: tert-Butyl (1E,4E)-8-bromo-4-(dipropylcarbamoyl)-3H-benzo[b]azepin-2-ylcarbamate (0.095 g, 0.205 mmol), 4-hydroxyphenylboronic acid (0.040 g, 0.286 mmol), Pd(OAc)$_2$ (0.0045 g, 0.020 mmol), 4,4'-(phenylphosphinidene)bisbenzenesulfonic acid dipotassium hydrate (0.022 g, 0.041 mmol), 2M sodium carbonate solution (0.307 mls, 0.614 mmol) were combined in 2 mls of ethanol and this mixture was purged with Argon for 5 minutes and then warmed to 65° C. under argon for 1.5 hours. The mixture was then diluted with citric acid, extracted with EtOAc (2×), extracts washed with saturated sodium carbonate solution, dried over sodium sulfate and concentrated under reduced pressure. Flash 40 Biotage (40S cartridge, 30% EtOAc/Hexane) afforded 0.040 g of tert-butyl (1E,4E)-4-(dipropylcarbamoyl)-8-(4-hydroxyphenyl)-3H-benzo[b]azepin-2-ylcarbamate (41%). m/z (APCI-pos) M+1=478.0.

Step B: tert-Butyl (1E,4E)-4-(dipropylcarbamoyl)-8-(4-hydroxyphenyl)-3H-benzo[b]azepin-2-ylcarbamate (0.040 g, 0.084 mmol) was dissolved in 1 ml of dichloromethane. 0.5 ml of TFA was then added and the mixture was stirred at room temperature for one hour. The reaction was then quenched by the addition of saturated sodium bicarbonate solution and stirred for 15 minutes, then extracted twice with dichloromethane, extracts dried over sodium sulfate and concentrated. Preparative thin layer chromatography (0.5 mm plate, 7% MeOH/DCM) afforded 6 mgs (19%) of (1E,4E)-2-amino-8-(4-hydroxyphenyl)-N,N-dipropyl-3H-benzo[b]azepine-4-carboxamide as a yellow solid. $^1$H NMR (400 MHz, CDCl$_3$) δ 7.47-7.53 (m, 2H), 7.41-7.44 (m, 1H), 7.30-7.33 (m, 1H), 6.88-6.93 (m, 2H), 6.83 (s, 2H), 3.42-3.54 (m, 4H), 2.81 (s, 2H), 1.61-1.72 (m, 4H), 0.89-0.97 (m, 6H); m/z (APCI-pos) M+1=378.2.

Example 202

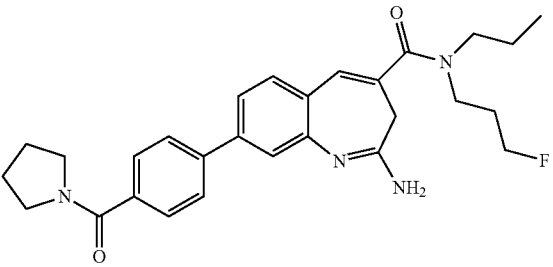 [SMILES: CCCN(CCCF)C(=O)C1=Cc2ccc(-c3ccc(C(=O)N4CCCC4)cc3)cc2N=C(N)C1]

(1E,4E)-2-Amino-N-(3-fluoropropyl)-N-propyl-8-(4-(pyrrolidine-1-carbonyl)phenyl)-3H-benzo[b]azepine-4-carboxamide Step A: tert-Butyl (1E,4E)-4-(3-fluoropropyl)(propyl)carbamoyl)-8-(4-(pyrrolidine-1-carbonyl)phenyl)-3H-benzo[b]azepin-2-ylcarbamate (19%) was prepared according to Example 208, Step D, substituting (1E,4E)-2-(tert-butoxycarbonylamino)-8-(4-(pyrrolidine-1-carbonyl)phenyl)-3H-benzo[b]azepine-4-carboxylic acid for (1E,4E)-8-Bromo-2-(tert-butoxycarbonylamino)-3H-benzo[b]azepine-4-carboxylic acid. m/z (APCI-pos) M+1=577.0.

Step B: (1E,4E)-2-Amino-N-(3-fluoropropyl)-N-propyl-8-(4-(pyrrolidine-1-carbonyl)phenyl)-3H-benzo[b]azepine-4-carboxamide (45%) was prepared according to Example 208, Step F, substituting tert-butyl (1E,4E)-4-((3-fluoropropyl)(propyl)carbamoyl)-8-(4-(pyrrolidine-1-carbonyl)phenyl)-3H-benzo[b]azepin-2-ylcarbamate for ethyl 4-((1E,4E)-2-(tert-butoxycarbonylamino)-4-((3-fluoropropyl)(propyl)carbamoyl)-3H-benzo[b]azepin-8-yl)benzoate. $^1$H NMR (400 MHz, DMSO-d$_6$) δ 7.70-7.76 (m, 2H), 7.57-7.64 (m, 2H), 7.36-7.42 (m, 1H), 7.24-7.34 (m, 2H), 6.78-6.84 (m, 3H), 4.40-4.61 (m, 2H), 3.43-3.52 (m, 6H), 2.75 (s, 2H), 1.79-1.96 (m, 6H), 1.53-1.63 (m, 2H), 0.79-0.90 (m, 3H); m/z (APCI-pos) M+1=477.3.

Example 203

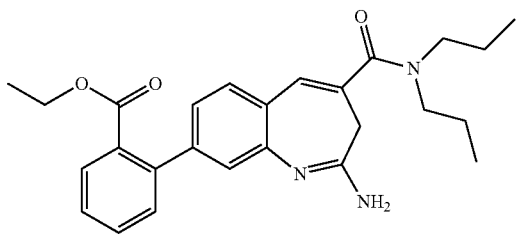 [SMILES: CCCN(CCC)C(=O)C1=Cc2ccc(-c3ccccc3C(=O)OCC)cc2N=C(N)C1]

Ethyl 2-((1E,4E)-2-amino-4-(dipropylcarbamoyl)-3H-benzo[b]azepin-8-yl)benzoate

Step A: Ethyl 2-((1E,4E)-2-amino-4-(dipropylcarbamoyl)-3H-benzo[b]azepin-8-yl)benzoate (24%) was prepared according to Example 206, Step B, substituting 2-(methoxycarbonyl)phenylboronic acid for 4-(methoxycarbonyl)phenylboronic acid. ¹H NMR (400 MHz, CDCl₃) δ 7.83-7.86 (m, 1H), 7.49-7.55 (m, 1H), 7.38-7.45 (m, 2H), 7.23-7.29 (m, 2H), 6.98-7.01 (m, 1H), 6.83 (s, 1H), 5.28 (br s, 1H), 4.08-4.16 (m, 2H), 3.41-3.51 (m, 4H), 2.82 (s, 2H), 1.61-1.72 (m, 4H), 1.00-1.05 (m, 3H), 0.90-0.97 (m, 6H); m/z (APCI-pos) M+1=434.2.

Example 204

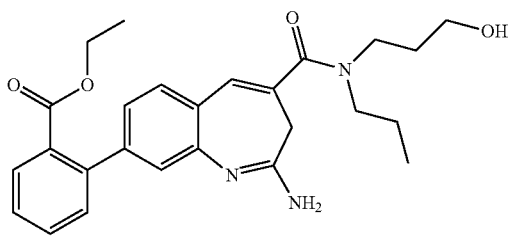 [SMILES: CCCN(CCCO)C(=O)C1=Cc2ccc(-c3ccccc3C(=O)OCC)cc2N=C(N)C1]

Ethyl 2-((1E,4E)-2-amino-4-((3-hydroxypropyl)(propyl)carbamoyl)-3H-benzo[b]azepin-8-yl)benzoate Step A: Ethyl 2-((1E,4E)-2-amino-4-((3-hydroxypropyl)(propyl)carbamoyl-3H-benzo[b]azepin-8-yl)benzoate (30%) was prepared according to Example 190, Steps A and B, substituting 2-(ethoxycarbonyl)phenylboronic acid for 4-(ethoxycarbonyl)phenylboronic acid. ¹H NMR (400 MHz, DMSO-d₆) δ 7.57-7.76 (m, 2H), 7.43-7.56 (m, 2H), 7.28-7.39 (m, 1H), 6.74-7.01 (m, 5H), 4.43-4.55 (m, 1H), 3.98-4.14 (m, 2H), 3.26-3.55 (m, 6H, partially obstructed by water peak), 2.74 (s, 2H), 1.67-1.82 (m, 2H), 1.49-1.66 (m, 2H), 0.71-1.02 (m, 6H); m/z (APCI-pos) M+1=450.2.

Example 206

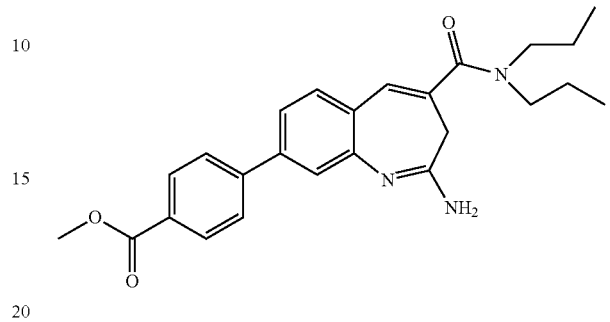

Methyl 4-((1E,4E)-2-amino-4-(dipropylcarbamoyl)-3H-benzo[b]azepin-8-yl)benzoate

Step A: A 50 ml round bottom flask equipped with a stir bar and nitrogen inlet was charged with 15 mls of dry toluene and dipropylamine (0.44 ml, 3.24 mmol). This was chilled to 0° C. and AlMe₃ (4.04 mls, 8.09 mmol, 2M in toluene) was then added. Once the addition was complete, the mixture was allowed to warm to room temperature (~20-30 minutes). (1E,4E)-ethyl 2-amino-8-bromo-3H-benzo[b]azepine-4-carboxylate (0.5 g, 1.62 mmol) was then added portionwise resulting in a dark solution. This mixture was warmed to 100° C. for about 16 hours, and then allowed to cool to room temperature. This mixture was then poured into 50 mls of a 30% aq. solution of Rochelle's salt and vigorously stirred for 20 minutes, then extracted with EtOAc (2×), extracts dried over sodium sulfate and concentrated under reduced pressure. Flash 40 Biotage (40M cartridge, 5% MeOH/DCM) afforded 201 mgs (32%) of (1E,4E)-2-amino-8-bromo-N,N-dipropyl-3H-benzo[b]azepine-4-carboxamide. m/z (APCI-pos) M+1=364.2, 366.2.

Step B: (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded 20 mgs (23%) of methyl 4-((1E,4E)-2-amino-4-(dipropylcarbamoyl)-3H-benzo[b]azepin-8-yl)benzoate. ¹H NMR (400 MHz, CDCl₃) δ 8.08-8.13 (m, 2H), 7.68-7.74 (m, 2H), 7.52-7.56 (m, 1H), 7.33-7.39 (m, 2H), 6.84 (s, 1H), 3.94 (s, 3H), 3.60-3.68 (m, 2H), 3.37-3.51 (m, 4H), 2.86 (s, 2H), 1.60-1.72 (m, 4H), 0.88-0.98 (m, 6H); m/z (APCI-pos) M+1=420.2.

Example 207

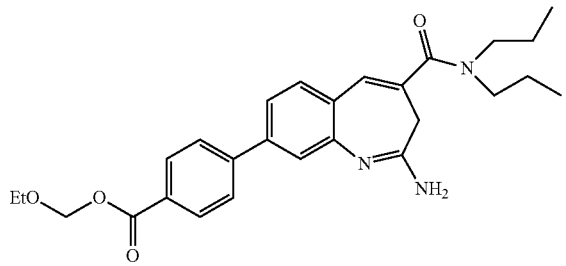 [SMILES: CCCN(CCC)C(=O)C1=Cc2ccc(-c3ccc(C(=O)OCOCC)cc3)cc2N=C(N)C1]

Ethoxymethyl 4-((1E,4E)-2-amino-4-(dipropylcarbamoyl)-3H-benzo[b]azepin-8-yl)benzoate Step A: 4-(4,4,5,5-tetramethyl-1,3,2-dioxaborolan-2-yl)benzoic acid (0.50 g, 2.02 mmol) was dissolved in 20 mls of dry acetonitrile. To this solution was added powdered potassium carbonate (0.42 g, 3.02 mmol) followed by chloromethyl ethyl ether (0.24 mls, 2.42 mmol). This mixture was warmed to 65° C. for 2 hours, then allowed to cool to room temperature, filtered and the filtrate concentrated to give ethoxymethyl 4-(4,4,5,5-tetramethyl-1,3,2-dioxaborolan-2-yl)benzoate as a solid (84%). This material was taken onto the next step without further purification.

Step B: Ethoxymethyl 4-((1E,4E)-2-amino-4-(dipropylcarbamoyl)-3H-benzo[b]azepin-8-yl)benzoate (17%) was prepared according to Example 206, Step B, substituting ethoxymethyl 4-(4,4,5,5-tetramethyl-1,3,2-dioxaborolan-2-yl)benzoate for 4-(methoxycarbonyl)phenylboronic acid. $^1$H NMR (400 MHz, CDCl$_3$) δ 8.12-8.17 (m, 2H), 7.72-7.76 (m, 2H), 7.54-7.56 (m, 1H), 7.33-7.40 (m, 2H), 6.84 (s, 1H), 5.57 (s, 2H), 3.78-3.85 (m, 2H), 3.61-3.70 (m, 2H), 3.36-3.53 (m, 4H), 2.84 (s, 2H), 1.58-1.74 (m, 4H), 1.26-1.31 (m, 3H), 0.89-0.99 (m, 6H); m/z (APCI-pos) M+1=464.2.

Example 208

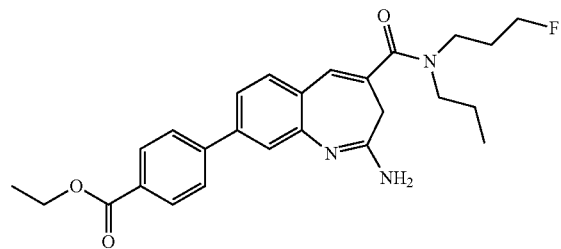 [SMILES: CCCN(CCCF)C(=O)C1=Cc2ccc(-c3ccc(C(=O)OCC)cc3)cc2N=C(N)C1]

Ethyl 4-((1E,4E)-2-amino-4-((3-fluoropropyl)(propyl)carbamoyl)-3H-benzo[b]azepin-8-yl)benzoate Step A: 3-Fluoropropan-1-amine hydrochloride (1.00 g, 8.81 mmol) was dissolved in 90 mls of dry dichloromethane. To this was added di-t-butyl dicarbonate (2.11 g, 9.69 mmol) and triethylamine (2.70 mls, 19.37 mmol). This mixture was stirred at room temperature for 16 hours, then washed with 1N aq. HCl (1×), saturated sodium bicarbonate solution (1×), dried over sodium sulfate and concentrated under reduced pressure to give 1.6 g (100%) of tert-butyl 3-fluoropropylcarbamate as a clear and colorless oil.

Step B: tert-Butyl 3-fluoropropylcarbamate (1.6 g, 9.03 mmol) was dissolved in 90 mls of dry DMF. To this solution was added sodium hydride (1.44 g, 36.12 mmol, 60% dispersion in mineral oil) and the mixture was stirred at room temperature for 20 minutes. Iodopropane (3.17 mls, 27.09 mmol) was then added and the mixture was warmed to 65° C. for 10 hours, then quenched with saturated ammonium chloride solution. This was extracted with EtOAc (2×), extracts washed twice with brine, dried over sodium sulfate and concentrated to 2 g (100%) of tert-butyl 3-fluoropropyl(propyl)carbamate as a clear oil.

Step C: tert-Butyl 3-fluoropropyl(propyl)carbamate (2.00 g, 9.12 mmol) was dissolved in 90 mls of ether. This mixture was chilled to 0° C. and HCl gas was bubbled in to the reaction mixture for 15 minutes, reaction vessel capped and the mixture allowed to warm to room temperature, and stirred for 6 hours. The mixture was then concentrated to a sticky solid, giving 1.6 g (99%) of 3-fluoro-N-propylpropan-1-amine hydrochloride.

Step D: (1E,4E)-8-Bromo-2-(tert-butoxycarbonylamino)-3H-benzo[b]azepine-4-carboxylic acid (0.275 g, 0.721 mmol) was dissolved in 7 mls of dry DMF. To this solution was added HOBT (0.107 g, 0.794 mmol) and EDCI (0.152 mmol, 0.794 mmol), and this mixture was stirred at room temperature for 20 minutes. 3-Fluoro-N-propylpropan-1-amine hydrochloride (0.124 mmol, 0.794 mmol) followed by triethylamine (0.211 mls, 1.515 mmol) were then added and the reaction mixture stirred at room temperature for 16 hours. The mixture was then diluted with EtOAc, washed several times with brine, dried over sodium sulfate and concentrated under reduced pressure. Flash 40 Biotage (40S cartridge, 25% EtOAc/Hexane) afforded 0.089 g (26%) of tert-butyl (1E,4E)-8-bromo-4-((3-fluoropropyl)(propyl)carbamoyl)-3H-benzo[b]azepin-2-ylcarbamate. m/z (APCI-pos) M+1=481.8 and 483.8.

Step E: Ethyl 4-((1E,4E)-2-(tert-butoxycarbonylamino)-4-(3-fluoropropyl)(propyl)(carbamoyl)-3-H-[b]azepin-8-yl)benzoate was prepared according to Example 206, Step B, substituting tert-butyl (1E,4E)-8-bromo-4-((3-fluoropropyl)(propyl)carbamoyl)-3H-benzo[b]azepin-2-ylcarbamate for (1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. m/z (APCI-pos) M+1=551.9.

Step F: The crude product from Step E was then taken up in 2 mls of dichloromethane and 1 ml of TFA, and stirred at room temperature for one hour. The mixture was concentrated under reduced pressure and the resulting crude product was taken up in DCM (10 mls) and concentrated ammonium hydroxide (5 mls) and stirred at room temperature for 15 minutes, then extracted with dichloromethane. The extracts were dried over sodium sulfate and concentrated under reduced pressure. Preparative thin layer chromatography (2×0.5 mm plates, 7% MeOH/DCM/0.5% NH$_4$OH) afforded 17 mgs (36%) of ethyl 4-((1E,4E)-2-amino-4-((3-fluoropropyl)(propyl)carbamoyl)-3H-benzo[b]azepin-8-yl)benzoate. $^1$H NMR (400 MHz, CDCl$_3$) δ 8.09-8.14 (m, 2H), 7.70-7.74 (m, 2H), 7.52-7.55 (m, 1H), 7.32-7.41 (m, 2H), 6.87 (m, 1H), 5.11 (br s, 1H), 4.57-4.63 (m, 1H), 4.46-4.52 (m, 1H), 4.37-4.45 (m, 2H), 3.57-3.73 (m, 2H), 3.42-3.55 (m, 2H), 2.82 (s, 2H), 1.99-2.15 (m, 2H), 1.62-1.76 (m, 2H), 1.38-1.45 (m, 3H), 0.89-0.98 (m, 3H); m/z (APCI-pos) M+1=452.2.

Example 209

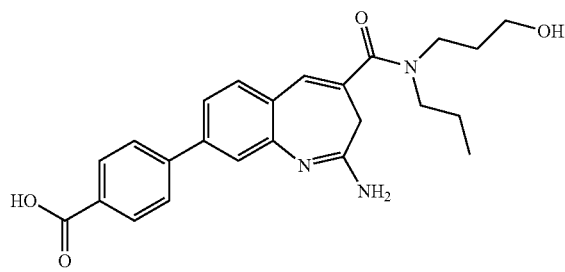 [SMILES: CCCN(CCCO)C(=O)C1=Cc2ccc(-c3ccc(C(=O)O)cc3)cc2N=C(N)C1]

4-((1E,4E)-2-Amino-4-((3-hydroxypropyl)(propyl)carbamoyl)-3H-benzo[b]azepin-8-yl)benzoic acid Step A: Benzyl 4-((1E,4E)-2-amino-4-((3-hydroxypropyl)(propyl)carbamoyl)-3H-benzo[b]azepin-8-yl)benzoate (8%) was prepared according to Example 190, Steps A and B, substituting 4-(benzyloxycarbonyl)phenylboronic acid for 4-(ethoxycarbonyl)phenylboronic acid.

Step B: 4-((1E,4E)-2-Amino-4-((3-hydroxypropyl)(propyl)carbamoyl)-3H-benzo[b]azepin-8-yl)benzoic acid (63%) was prepared according to Example 188, Step B, substituting benzyl 4-((1E,4E)-2-amino-4-((3-hydroxypropyl)(propyl)carbamoyl)-3H-benzo[b]azepin-8-yl)benzoate for benzyl 4-((1E,4E)-2-amino-4-(dipropylcarbamoyl)-3H-benzo[b]azepin-8-yl)benzoate. m/z (APCI-pos) M+1=422.3.

Example 210

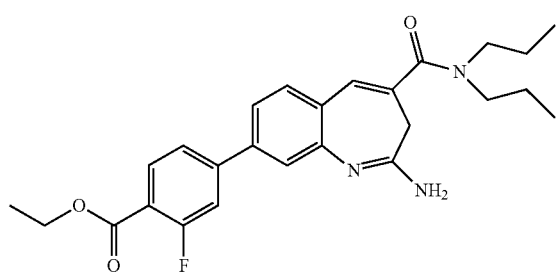 [SMILES: CCCN(CCC)C(=O)C1=Cc2ccc(-c3ccc(C(=O)OCC)c(F)c3)cc2N=C(N)C1]

Ethyl 4-((1E,4E)-2-amino-4-(dipropylcarbamoyl)-3H-benzo[b]azepin-8-yl)-2-fluorobenzoate Step A: Ethyl 4-((1E,4E)-2-amino-4-(dipropylcarbamoyl)-3H-benzo[b]azepin-8-yl)-2-fluorobenzoate (32%) was prepared according to Example 206, Step B, substituting 3-fluoro-4-(methoxycarbonyl)phenylboronic acid for 4-(methoxycarbonyl)phenylboronic acid. $^1$H NMR (400 MHz, CDCl$_3$) δ 7.97-8.02 (m, 1H), 7.47-7.53 (m, 2H), 7.29-7.43 (m, 3H), 6.89 (s, 1H), 4.36-4.46 (m, 2H), 3.56-3.68 (m, 2H), 3.38-3.50 (m, 4H), 2.84 (s, 2H), 1.60-1.71 (m, 4H), 1.38-1.44 (m, 3H), 0.90-0.97 (m, 6H); m/z (APCI-pos) M+1=452.2.

Example 211

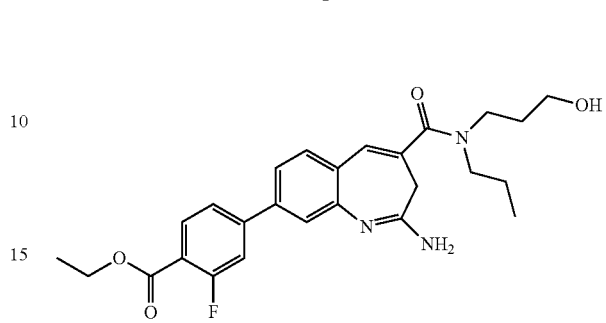

Ethyl 4-((1E,4E)-2-amino-4-((3-hydroxypropyl)(propyl)carbamoyl)-3H-benzo[b]azepin-8-yl)-2-fluorobenzoate Step A: Ethyl 4-((1E,4E)-2-amino-4-((3-hydroxypropyl)(propyl)carbamoyl)-3H-benzo[b]azepin-8-yl)-2-fluorobenzoate (19%) was prepared according to Example 190, Steps A and B, substituting 4-(ethoxycarbonyl)-3-fluorophenylboronic acid for 4-(ethoxycarbonyl)phenylboronic acid. $^1$H NMR (400 MHz, CDCl$_3$) δ 7.97-8.04 (m, 1H), 7.47-7.52 (m, 2H), 7.36-7.45 (m, 2H), 7.29-7.33 (m, 1H), 6.88 (s, 1H), 5.19 (br s, 1H), 4.38-4.47 (m, 2H), 3.59-3.72 (m, 5H), 3.45-3.52 (m, 2H), 2.84 (s, 2H), 1.79-1.90 (m, 2H), 1.67-1.76 (m, 2H), 1.40-1.42 (m, 3H), 0.89-0.97 (m, 3H); m/z (APCI-pos) M+1=468.2.

Example 212

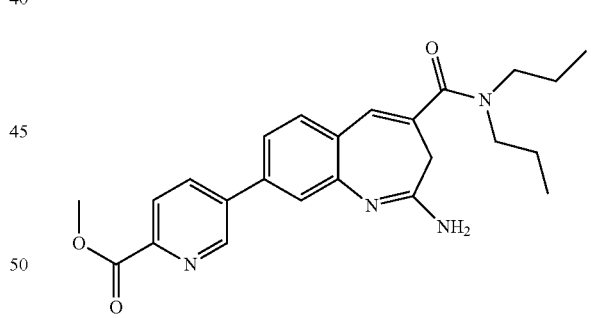

Methyl 5-((1E,4E)-2-amino-4-(dipropylcarbamoyl)-3H-benzo[b]azepin-8-yl)picolinate Step A: Methyl 5-((1E,4E)-2-amino-4-(dipropylcarbamoyl)-3H-benzo[b]azepin-8-yl)picolinate (17%) was prepared according to Example 206, Step B, substituting methyl 5-(4,4,5,5-tetramethyl-1,3,2-dioxaborolan-2-yl)picolinate for 4-(methoxycarbonyl)phenylboronic acid. $^1$H NMR (400 MHz, DMSO-d$_6$) δ 9.89 (s, 1H), 8.98-9.10 (s, 1H), 8.32-8.36 (m, 1H), 8.18-8.22 (m, 1H), 7.71-7.89 (m, 3H), 7.06 (s, 1H), 3.93 (s, 3H), 3.23-3.40 (m, 4H), 1.53-1.63 (m, 4H), 0.75-0.97 (m, 6H); m/z (APCI-pos) M+1=421.2.

Example 220

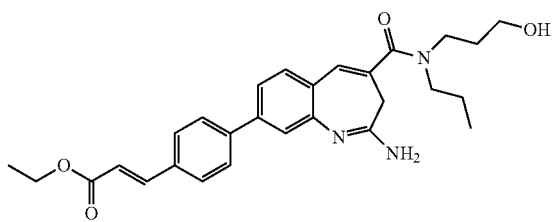 [SMILES: CCCN(CCCO)C(=O)C1=Cc2ccc(-c3ccc(/C=C/C(=O)OCC)cc3)cc2N=C(N)C1]

(E)-Ethyl 3-(4-((1E,4E)-2-amino-4-((3-hydroxypropyl)(propyl)carbamoyl)-3H-benzo[b]azepin-8-yl)phenyl)acrylate Step A: (E)-Ethyl 3-(4-((1E,4E)-2-amino-4-((3-hydroxylpropyl)(propyl)carbamoyl)-3H-benzo[b]azepin-8-yl)phenyl)acrylate (40%) was prepared according to Example 190, Steps A and B, substituting (E)-4-(3-ethoxy-3-oxoprop-1-enyl)phenylboronic acid for 4-(ethoxycarbonyl)phenylboronic acid. $^1$H NMR (400 MHz, CDCl$_3$) δ 7.67-7.75 (m, 3H), 7.58-7.62 (m, 2H), 7.51-7.53 (m, 1H), 7.30-7.39 (m, 2H), 6.88 (s, 1H), 6.48 (d, 1H), 5.11 (br s, 1H), 4.24-4.32 (m 2H), 3.58-3.70 (m, 4H), 2.82 (s, 2H), 1.78-1.89 (m, 2H), 1.66-1.78 (m, 2H), 1.30-1.40 (m, 3H), 0.89-0.99 (m, 3H); m/z (APCI-pos) M+1=476.2.

Example 2

HEK/TLR Assays

The activity of the compounds of this invention may be determined by the following assays.

The HEK-293 hTLR transfectant assay employs HEK293 cells stably transfected with various hTLRs and transiently co-transfected with a plasmid containing an NF-κB driven secreted embryonic alkaline phosphate (SEAP) reporter gene. Stimulation of TLRs activates their downstream signaling pathways and induces nuclear translocation of the transcription factor NF-κB. Reporter gene activity is then measured using a spectrophotometric assay.

To measure agonist activity, human embryonic kidney (HEK) cells which stably express various human TLR genes, including TLR7 and TLR8, and a NFkB-luciferase reporter gene (e.g., 293XL-hTLR8 cells available from InvivoGen, San Diego, Calif.) are prepared according to supplier's instructions and incubated with various concentrations of test compound overnight. The amount of induced luciferase is measured by reading the absorbance at 650 mu. Agonist compounds of the invention have an MC$_{50}$ of 25 μM or less, wherein MC$_{50}$ is defined as the concentration at which 50% of maximum induction is seen.

Example 3

PBMC Assays for TLR7 and TLR8

Peripheral blood mononuclear cells (PBMCs) from human blood were isolated using BD Vacutainer Cell Preparation Tubes with sodium citrate. Cells were incubated with compound overnight. TLR8 activity was assayed by measuring the amount of TNFα in supernatants by ELISA. TLR7 activity was assayed by measuring the amount of IFNα in supernatants by ELISA (R&D Systems). Compounds of this invention had an MC$_{50}$ of 100 or less, wherein MC$_{50}$ is the concentration at which 50% of the maximum induction is seen. The results of this assay are shown below in Tables 2 and 3.

MC$_{50}$ numbers are represented as factors of ten, for example, + indicates an MC$_{50}$ value of ×10$^4$, or a value in the tens of thousands of nanomolar (nM range); ++ indicates an MC$_{50}$ value of ×10$^3$, or a value in the thousands; +++ indicates an MC$_{50}$ value of ×10$^2$, or a value in the hundreds; and ++++ indicates an MC$_{50}$ value of ×10$^1$ or 10°, or a value in the tens or ones.

| Cmpd # | Structure | TLR8 MC$_{50}$ |
|---|---|---|
| 141 | 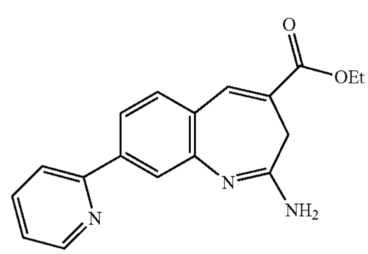 [SMILES: CCOC(=O)C1=Cc2ccc(-c3ccccn3)cc2N=C(N)C1] | +++ |
| 142 | 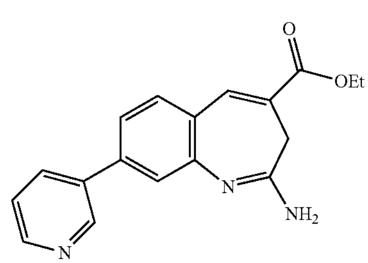 [SMILES: CCOC(=O)C1=Cc2ccc(-c3cccnc3)cc2N=C(N)C1] | ++++ |

-continued

| Cmpd # | Structure | TLR8 MC$_{50}$ |
|---|---|---|
| 143 | 2-amino-8-(pyridin-4-yl)-3H-benzo[b]azepine-4-carboxylic acid ethyl ester | ++++ |
| 144 | 2-amino-8-(pyrimidin-5-yl)-3H-benzo[b]azepine-4-carboxylic acid ethyl ester | ++++ |
| 145 | 2-amino-8-(3-cyanophenyl)-3H-benzo[b]azepine-4-carboxylic acid ethyl ester | ++++ |
| 146 | 2-amino-8-(4-cyanophenyl)-3H-benzo[b]azepine-4-carboxylic acid ethyl ester | +++ |
| 147 | 2-amino-8-(3-(N,N-dimethylcarbamoyl)phenyl)-3H-benzo[b]azepine-4-carboxylic acid ethyl ester | +++ |
| 154 | 2-amino-8-(4-(N,N-dimethylcarbamoyl)phenyl)-3H-benzo[b]azepine-4-carboxylic acid ethyl ester | +++ |

-continued
| Cmpd # | Structure | TLR8 MC$_{50}$ |
|---|---|---|
| 155 | 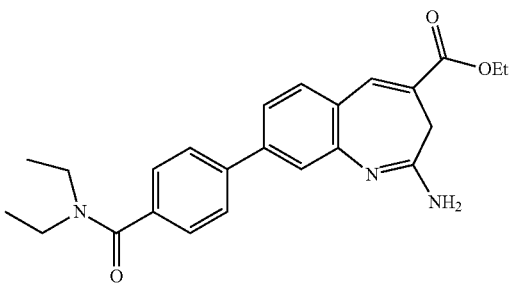 [SMILES: CCOC(=O)C1=Cc2ccc(-c3ccc(C(=O)N(CC)CC)cc3)cc2N=C(N)C1] | +++ |
| 156 | 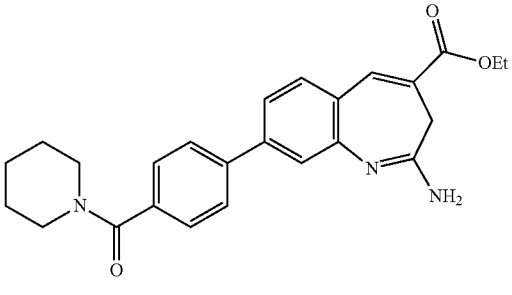 [SMILES: CCOC(=O)C1=Cc2ccc(-c3ccc(C(=O)N4CCCCC4)cc3)cc2N=C(N)C1] | +++ |
| 101 | 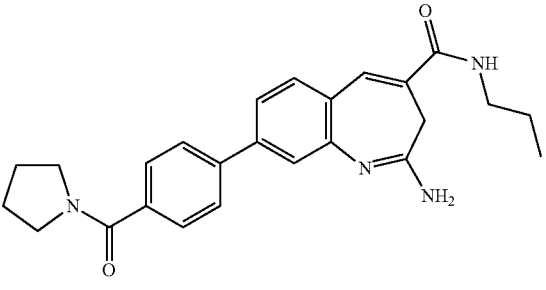 [SMILES: CCCNC(=O)C1=Cc2ccc(-c3ccc(C(=O)N4CCCC4)cc3)cc2N=C(N)C1] | +++ |
| 102 | 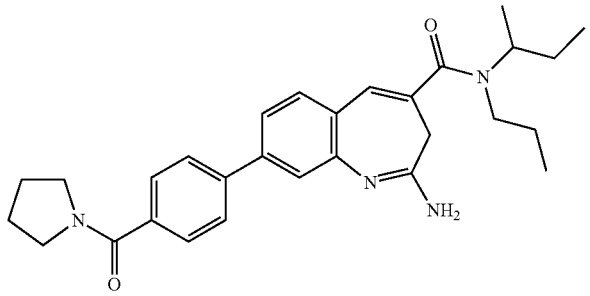 [SMILES: CCCN(C(=O)C1=Cc2ccc(-c3ccc(C(=O)N4CCCC4)cc3)cc2N=C(N)C1)C(C)CC] | +++ |
| 103 | 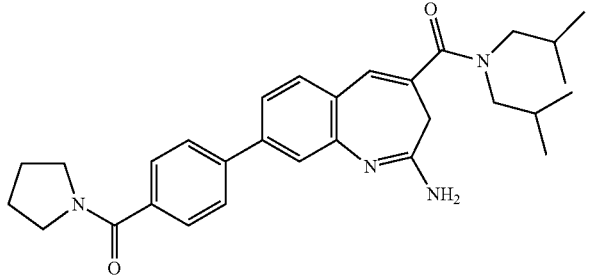 [SMILES: CC(C)CN(CC(C)C)C(=O)C1=Cc2ccc(-c3ccc(C(=O)N4CCCC4)cc3)cc2N=C(N)C1] | ++ |

| Cmpd # | Structure | TLR8 MC$_{50}$ |
|---|---|---|
| 104 | 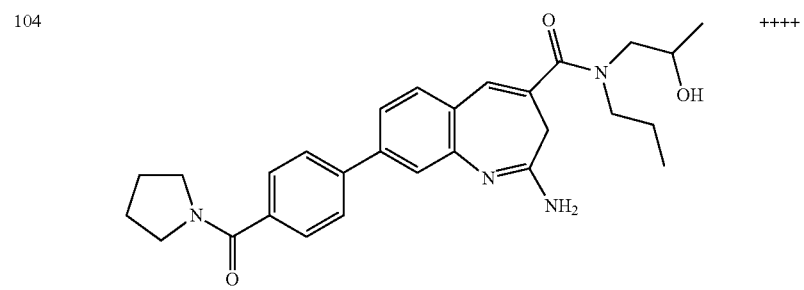 | ++++ |
| 105 | 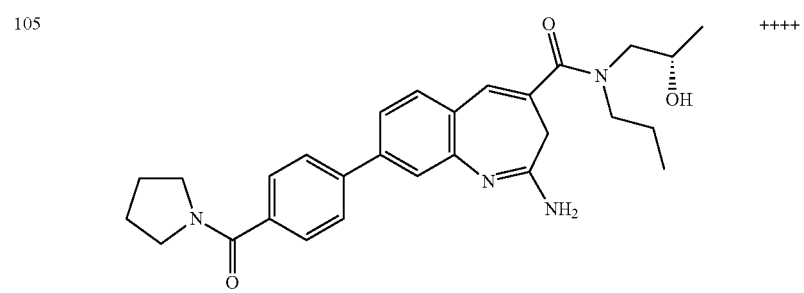 *stereo chem. arbitrary | ++++ |
| 106 | 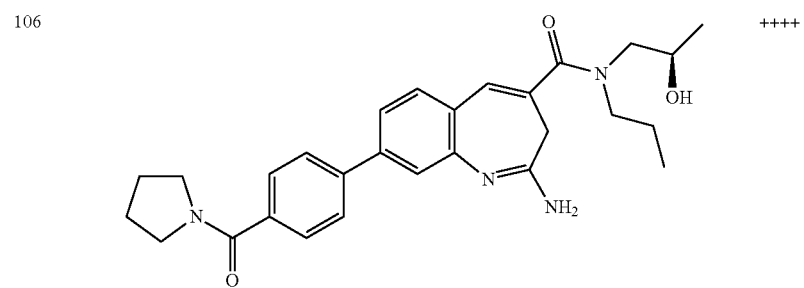 *stereo chem. arbitrary | ++++ |
| 107 | 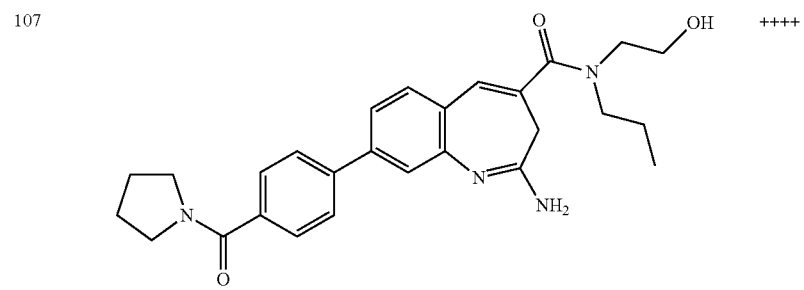 | ++++ |
| 109 | 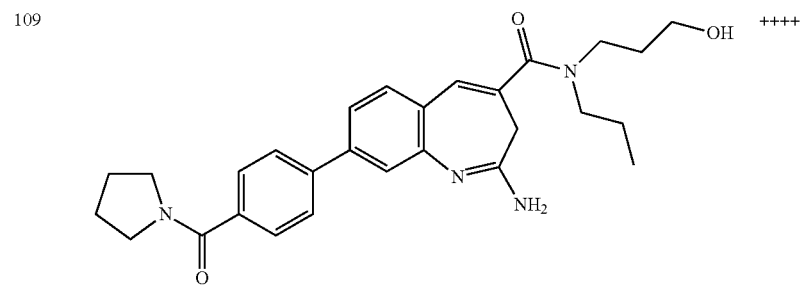 | ++++ |

| Cmpd # | Structure | TLR8 MC$_{50}$ |
|---|---|---|
| 110 | 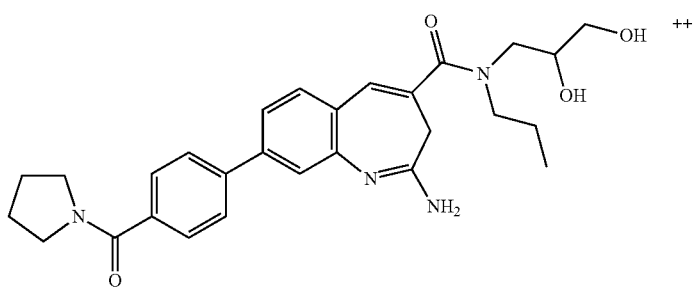 | ++ |
| 112 | 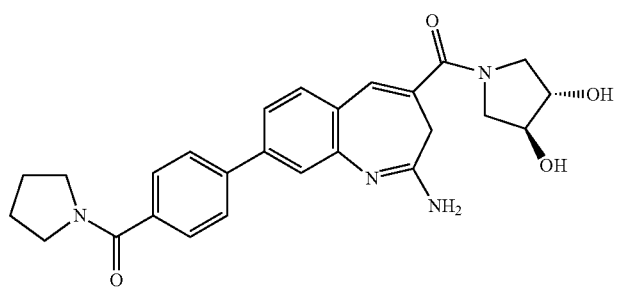 [SMILES: NC1=Nc2cc(-c3ccc(C(=O)N4CCCC4)cc3)ccc2C=C(C(=O)N2C[C@H](O)[C@@H](O)C2)C1] | ++ |
| 117 | 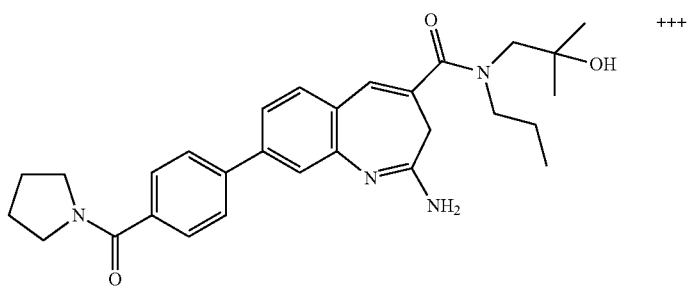 | +++ |
| 119 | 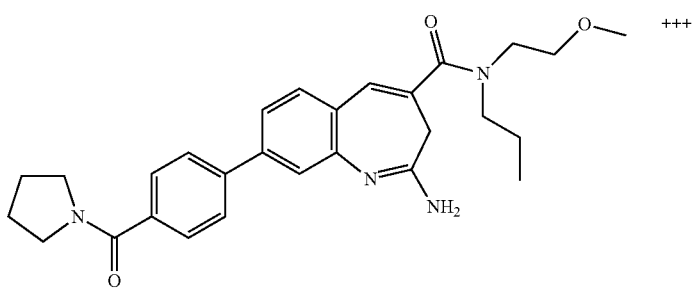 | +++ |
| 120 | 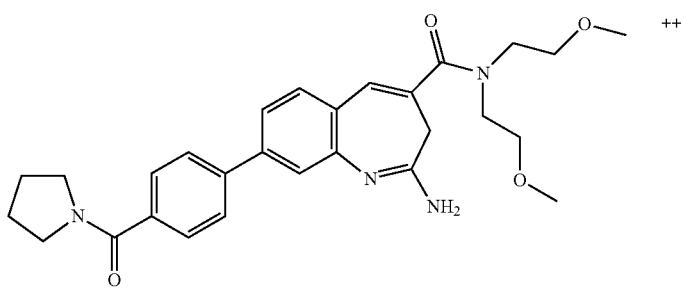 | ++ |

-continued

| Cmpd # | Structure | TLR8 MC$_{50}$ |
|---|---|---|
| 174 | 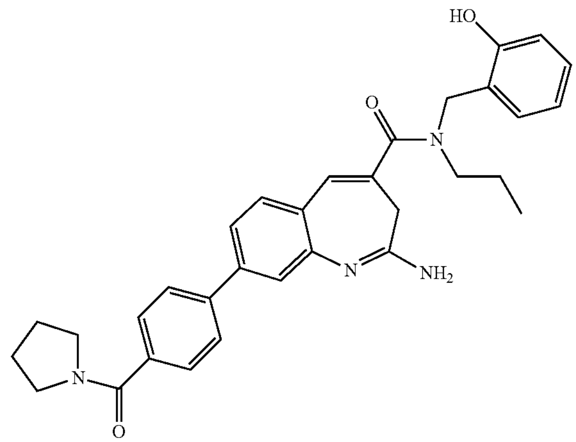 [SMILES: CCCN(Cc1ccccc1O)C(=O)C1=Cc2ccc(-c3ccc(C(=O)N4CCCC4)cc3)cc2N=C(N)C1] | +++ |
| 176 | 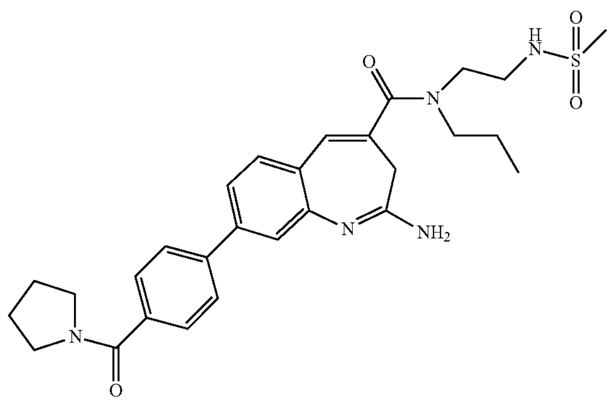 [SMILES: CCCN(CCNS(C)(=O)=O)C(=O)C1=Cc2ccc(-c3ccc(C(=O)N4CCCC4)cc3)cc2N=C(N)C1] | ++ |
| 178 | 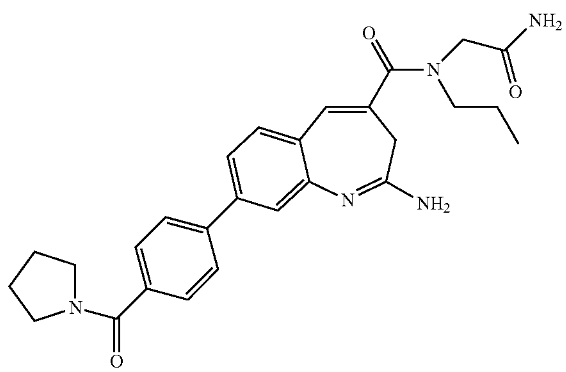 [SMILES: CCCN(CC(N)=O)C(=O)C1=Cc2ccc(-c3ccc(C(=O)N4CCCC4)cc3)cc2N=C(N)C1] | +++ |
| 127 | 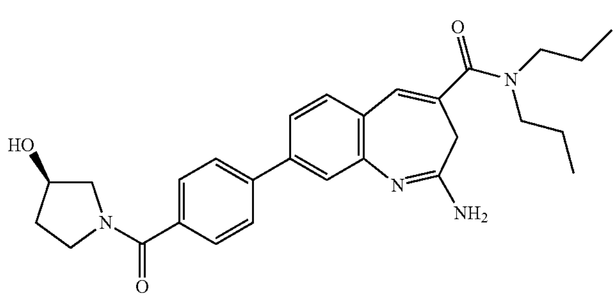 [SMILES: CCCN(CCC)C(=O)C1=Cc2ccc(-c3ccc(C(=O)N4CC[C@@H](O)C4)cc3)cc2N=C(N)C1] | ++++ |

-continued

| Cmpd # | Structure | TLR8 MC$_{50}$ |
|---|---|---|
| 128 | 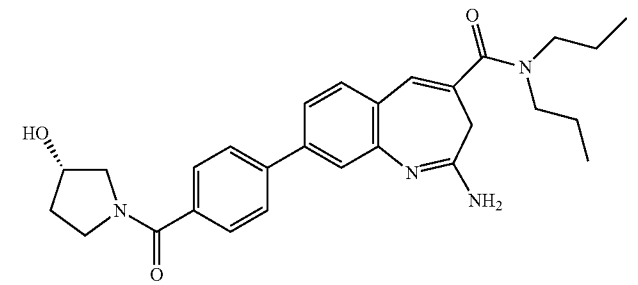 [SMILES: CCCN(CCC)C(=O)C1=Cc2ccc(-c3ccc(C(=O)N4CC[C@H](O)C4)cc3)cc2N=C(N)C1] | ++++ |
| 129 | 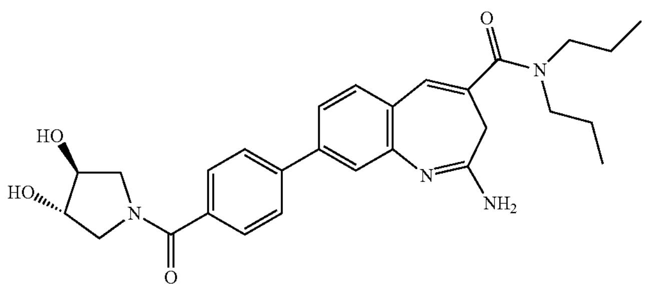 [SMILES: CCCN(CCC)C(=O)C1=Cc2ccc(-c3ccc(C(=O)N4C[C@H](O)[C@@H](O)C4)cc3)cc2N=C(N)C1] | +++ |
| 130 | 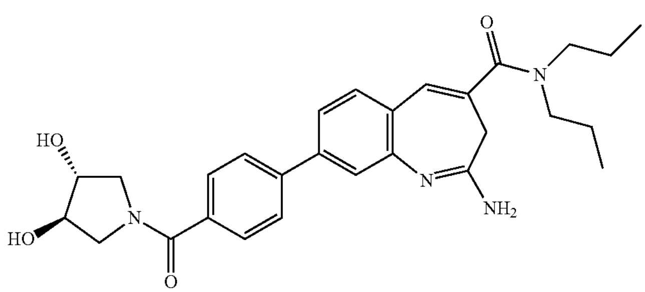 [SMILES: CCCN(CCC)C(=O)C1=Cc2ccc(-c3ccc(C(=O)N4C[C@@H](O)[C@H](O)C4)cc3)cc2N=C(N)C1] | +++ |
| 182 | 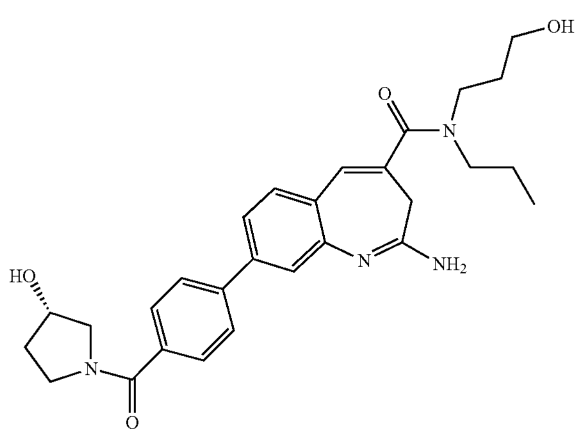 [SMILES: CCCN(CCCO)C(=O)C1=Cc2ccc(-c3ccc(C(=O)N4CC[C@H](O)C4)cc3)cc2N=C(N)C1] | ++++ |

-continued
| Cmpd # | Structure | TLR8 MC$_{50}$ |
|---|---|---|
| 115 | 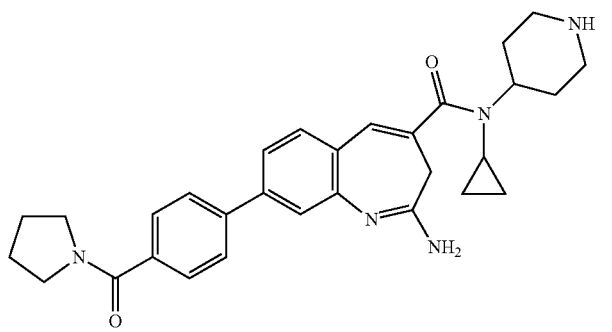 [SMILES: NC1=Nc2cc(-c3ccc(C(=O)N4CCCC4)cc3)ccc2C=C(C(=O)N(C2CCNCC2)C2CC2)C1] | ++ |
| 121 | 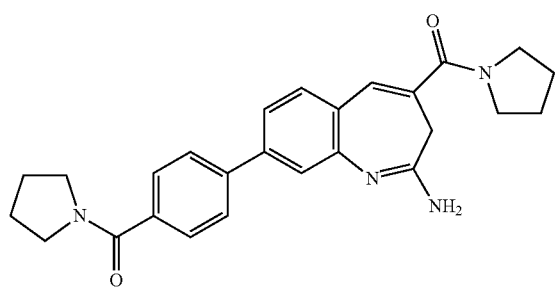 [SMILES: NC1=Nc2cc(-c3ccc(C(=O)N4CCCC4)cc3)ccc2C=C(C(=O)N2CCCC2)C1] | + |
| 122 | 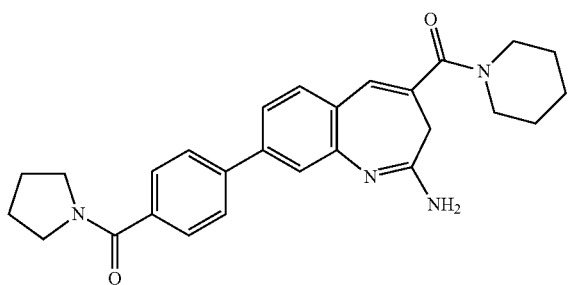 [SMILES: NC1=Nc2cc(-c3ccc(C(=O)N4CCCC4)cc3)ccc2C=C(C(=O)N2CCCCC2)C1] | ++ |
| 124 | 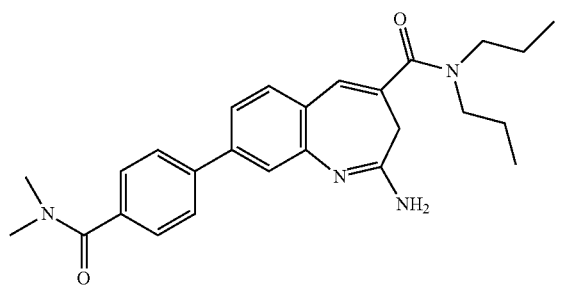 [SMILES: CCCN(CCC)C(=O)C1=Cc2ccc(-c3ccc(C(=O)N(C)C)cc3)cc2N=C(N)C1] | +++ |
| 125 | 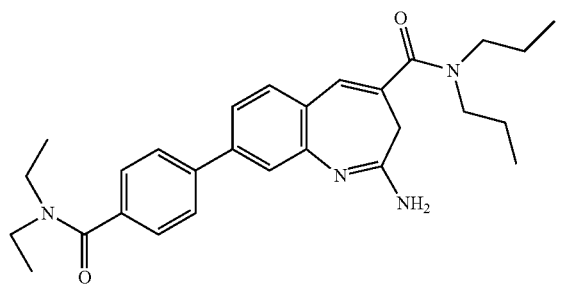 [SMILES: CCCN(CCC)C(=O)C1=Cc2ccc(-c3ccc(C(=O)N(CC)CC)cc3)cc2N=C(N)C1] | +++ |

-continued

| Cmpd # | Structure | TLR8 MC$_{50}$ |
|---|---|---|
| 126 | 2-amino-3H-benzo[b]azepine-4-carboxylic acid N,N-dipropylamide with 4-(piperidine-1-carbonyl)phenyl substituent | +++ |
| 133 | 2-amino-3H-benzo[b]azepine-4-carboxylic acid N,N-dipropylamide with pyridin-3-yl substituent | ++++ |
| 134 | 2-amino-3H-benzo[b]azepine-4-carboxylic acid N,N-dipropylamide with pyridin-4-yl substituent | +++ |
| 135 | 2-amino-3H-benzo[b]azepine-4-carboxylic acid N,N-dipropylamide with pyrimidin-5-yl substituent | ++++ |
| 136 | 2-amino-3H-benzo[b]azepine-4-carboxylic acid N,N-dipropylamide with 3-cyanophenyl substituent | ++++ |
| 137 | 2-amino-3H-benzo[b]azepine-4-carboxylic acid N,N-dipropylamide with 4-cyanophenyl substituent | ++++ |

-continued
| Cmpd # | Structure | TLR8 MC50 |
|---|---|---|
| 138 | 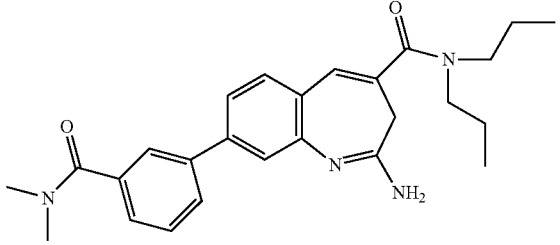 [SMILES: CCCN(CCC)C(=O)C1=Cc2ccc(-c3cccc(C(=O)N(C)C)c3)cc2N=C(N)C1] | ++++ |
| 139 | 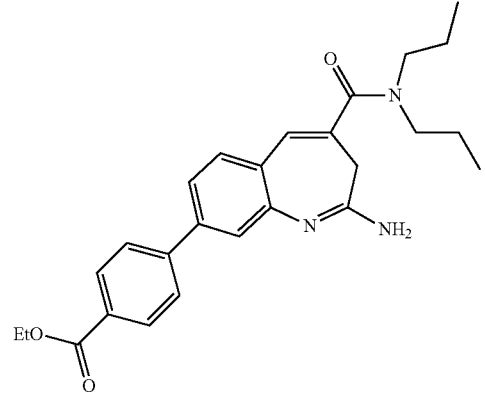 [SMILES: CCCN(CCC)C(=O)C1=Cc2ccc(-c3ccc(C(=O)OCC)cc3)cc2N=C(N)C1] | +++ |
| 186 | 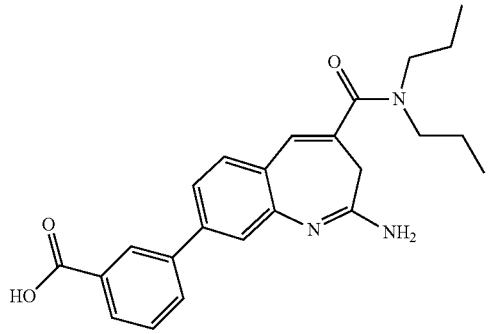 | + |
| 187 | 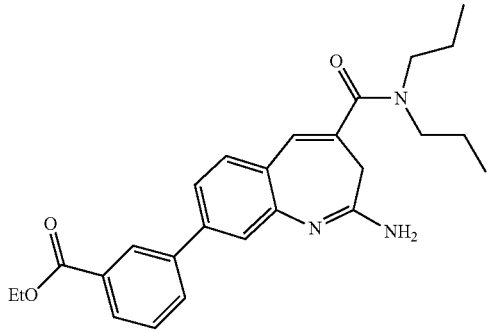 [SMILES: CCCN(CCC)C(=O)C1=Cc2ccc(-c3cccc(C(=O)O)c3)cc2N=C(N)C1] | +++ |

-continued

| Cmpd # | Structure | TLR8 MC$_{50}$ |
|---|---|---|
| 188 | (structure) | ++ |
| 190 | (structure) | +++ |
| 194 | (structure) | +++ |
| 195 | (structure) | +++ |

-continued

| Cmpd # | Structure | TLR8 MC$_{50}$ |
|---|---|---|
| 202 | (structure: 2-amino-3H-benzazepine with 8-[4-(pyrrolidin-1-ylcarbonyl)phenyl] substituent and 4-carboxamide N-propyl-N-(3-fluoropropyl)) | +++ |
| 203 | (structure: 2-amino-3H-benzazepine with 8-(2-ethoxycarbonylphenyl) substituent and 4-carboxamide N,N-dipropyl) | +++ |
| 204 | (structure: 2-amino-3H-benzazepine with 8-(2-ethoxycarbonylphenyl) substituent and 4-carboxamide N-propyl-N-(3-hydroxypropyl)) | +++ |
| 206 | (structure: 2-amino-3H-benzazepine with 8-[4-(methoxycarbonyl)phenyl] substituent and 4-carboxamide N,N-dipropyl) | +++ |
| 207 | (structure: 2-amino-3H-benzazepine with 8-[4-(ethoxymethoxycarbonyl)phenyl] substituent and 4-carboxamide N,N-dipropyl) | ++ |

| Cmpd # | Structure | TLR8 MC$_{50}$ |
|---|---|---|
| 208 | 8-[4-(ethoxycarbonyl)phenyl]-N-(3-fluoropropyl)-N-propyl-2-amino-3H-benzo[b]azepine-4-carboxamide | ++ |
| 209 | 8-[4-carboxyphenyl]-N-(3-hydroxypropyl)-N-propyl-2-amino-3H-benzo[b]azepine-4-carboxamide | + |
| 210 | 8-[4-(ethoxycarbonyl)-3-fluorophenyl]-N,N-dipropyl-2-amino-3H-benzo[b]azepine-4-carboxamide | +++ |
| 211 | 8-[4-(ethoxycarbonyl)-3-fluorophenyl]-N-(3-hydroxypropyl)-N-propyl-2-amino-3H-benzo[b]azepine-4-carboxamide | +++ |
| 212 | 8-[6-(methoxycarbonyl)pyridin-3-yl]-N,N-dipropyl-2-amino-3H-benzo[b]azepine-4-carboxamide | +++ |

-continued

| Cmpd # | Structure | TLR8 MC$_{50}$ |
|---|---|---|
| 220 | (benzazepine with 2-amino, 4-carboxamide N-propyl-N-(3-hydroxypropyl), 8-[4-(ethyl (E)-cinnamate)phenyl] substituent) | +++ |

TABLE 3

| Cmpd | Structure | TLR7 MC$_{50}$ |
|---|---|---|
| 142 | (2-amino-4-ethoxycarbonyl-8-(pyridin-3-yl)-3H-benzazepine) | ++ |
| 144 | (2-amino-4-ethoxycarbonyl-8-(pyrimidin-5-yl)-3H-benzazepine) | ++ |
| 147 | (2-amino-4-ethoxycarbonyl-8-[3-(N,N-dimethylcarbamoyl)phenyl]-3H-benzazepine) | ++ |
| 103 | (2-amino-4-(N,N-diisobutylcarbamoyl)-8-[4-(pyrrolidin-1-ylcarbonyl)phenyl]-3H-benzazepine) | ++ |

TABLE 3-continued

| Cmpd | Structure | TLR7 MC$_{50}$ |
|---|---|---|
| 104 | 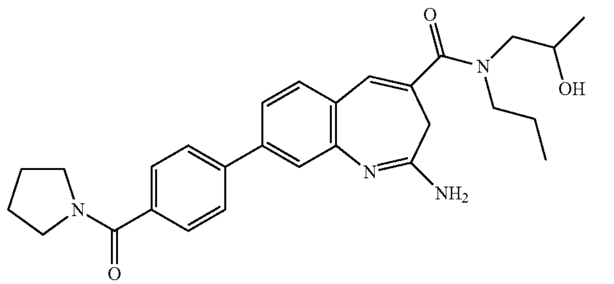 [SMILES: CCCN(CC(C)O)C(=O)C1=Cc2ccc(-c3ccc(C(=O)N4CCCC4)cc3)cc2N=C(N)C1] | ++ |
| 105 | 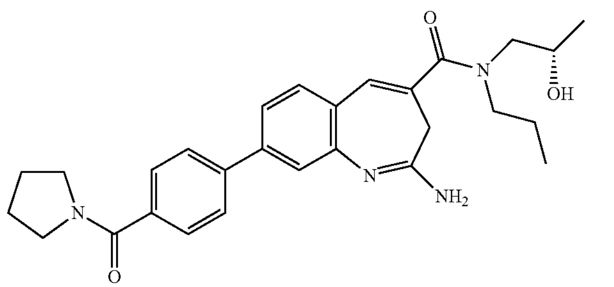 [SMILES: CCCN(C[C@H](C)O)C(=O)C1=Cc2ccc(-c3ccc(C(=O)N4CCCC4)cc3)cc2N=C(N)C1] | ++ |
| 106 | 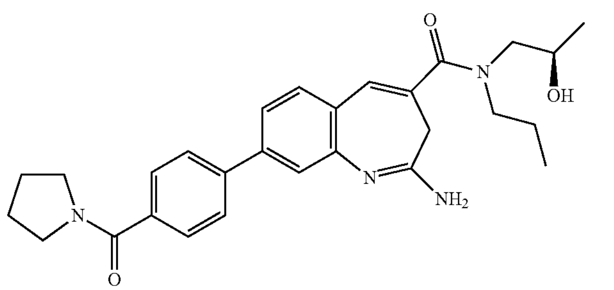 [SMILES: CCCN(C[C@@H](C)O)C(=O)C1=Cc2ccc(-c3ccc(C(=O)N4CCCC4)cc3)cc2N=C(N)C1] | ++ |
| 109 | 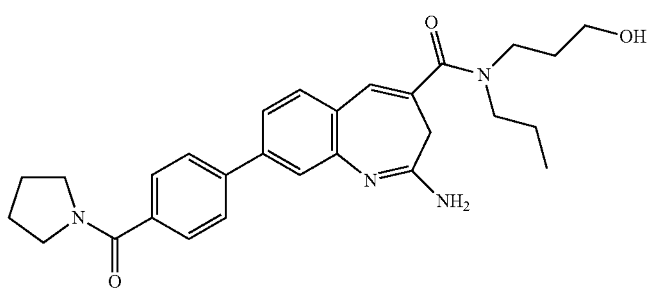 [SMILES: CCCN(CCCO)C(=O)C1=Cc2ccc(-c3ccc(C(=O)N4CCCC4)cc3)cc2N=C(N)C1] | ++ |
| 112 | 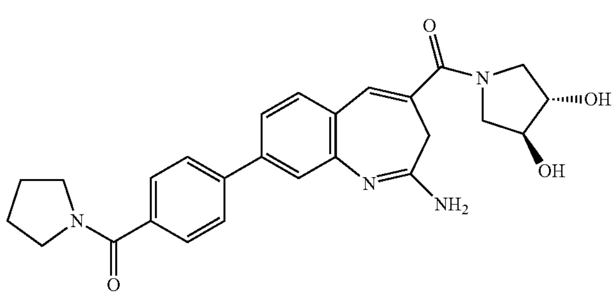 [SMILES: NC1=Nc2cc(-c3ccc(C(=O)N4CCCC4)cc3)ccc2C=C(C(=O)N2C[C@H](O)[C@@H](O)C2)C1] | + |

TABLE 3-continued
| Cmpd | Structure | TLR7 MC$_{50}$ |
|---|---|---|
| 117 | 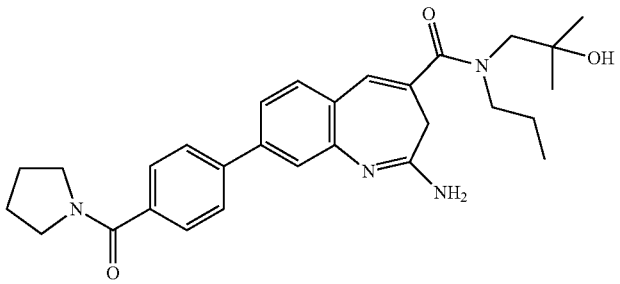 [SMILES: CCCN(CC(C)(C)O)C(=O)C1=Cc2ccc(-c3ccc(C(=O)N4CCCC4)cc3)cc2N=C(N)C1] | + |
| 119 | 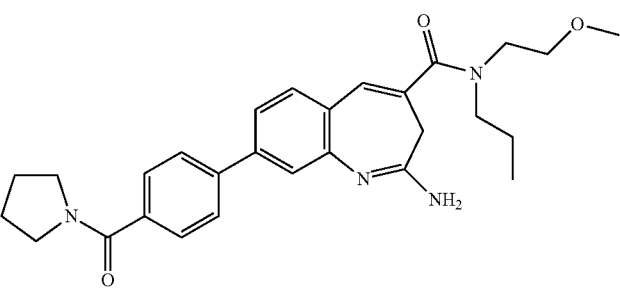 [SMILES: CCCN(CCOC)C(=O)C1=Cc2ccc(-c3ccc(C(=O)N4CCCC4)cc3)cc2N=C(N)C1] | ++ |
| 174 | 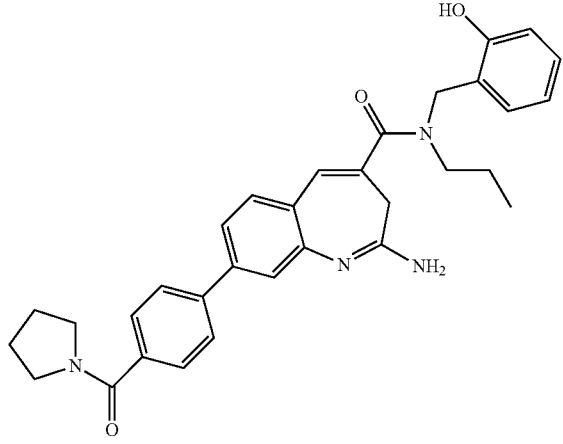 [SMILES: CCCN(Cc1ccccc1O)C(=O)C1=Cc2ccc(-c3ccc(C(=O)N4CCCC4)cc3)cc2N=C(N)C1] | ++ |
| 178 | 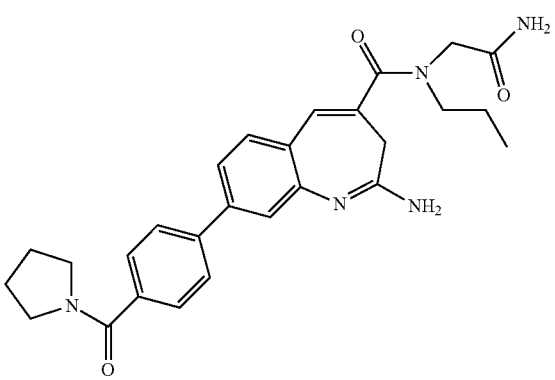 [SMILES: CCCN(CC(N)=O)C(=O)C1=Cc2ccc(-c3ccc(C(=O)N4CCCC4)cc3)cc2N=C(N)C1] | +++ |

TABLE 3-continued

| Cmpd | Structure | TLR7 MC$_{50}$ |
|---|---|---|
| 127 | 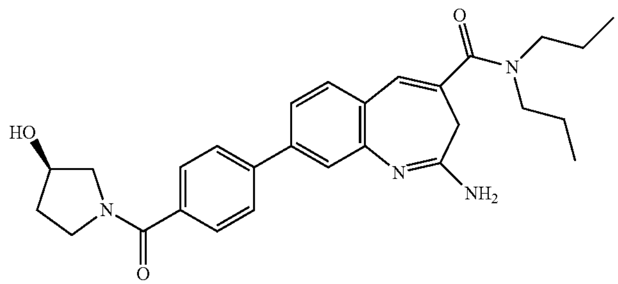 [SMILES: CCCN(CCC)C(=O)C1=Cc2ccc(-c3ccc(C(=O)N4CC[C@@H](O)C4)cc3)cc2N=C(N)C1] | ++ |
| 128 | 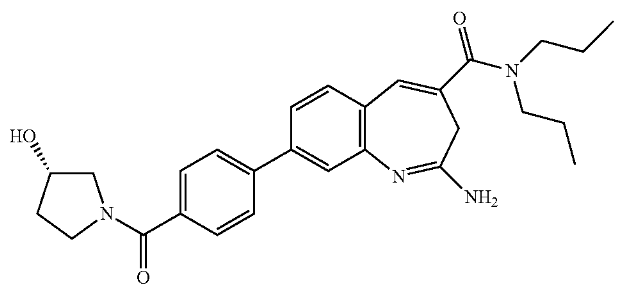 [SMILES: CCCN(CCC)C(=O)C1=Cc2ccc(-c3ccc(C(=O)N4CC[C@H](O)C4)cc3)cc2N=C(N)C1] | ++ |
| 182 | 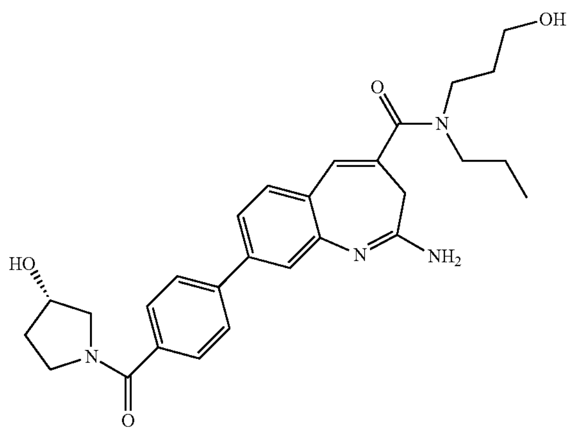 [SMILES: CCCN(CCCO)C(=O)C1=Cc2ccc(-c3ccc(C(=O)N4CC[C@H](O)C4)cc3)cc2N=C(N)C1] | ++ |
| 124 | 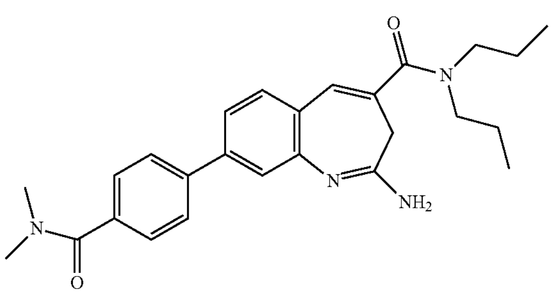 [SMILES: CCCN(CCC)C(=O)C1=Cc2ccc(-c3ccc(C(=O)N(C)C)cc3)cc2N=C(N)C1] | ++ |
| 125 | 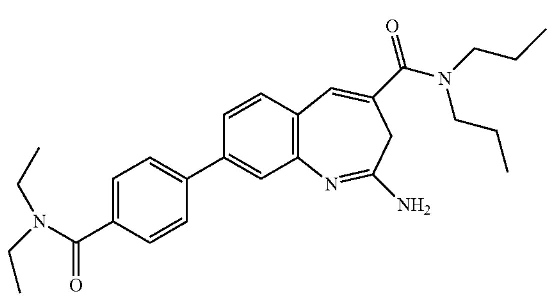 [SMILES: CCCN(CCC)C(=O)C1=Cc2ccc(-c3ccc(C(=O)N(CC)CC)cc3)cc2N=C(N)C1] | ++ |

TABLE 3-continued

| Cmpd | Structure | TLR7 MC$_{50}$ |
|---|---|---|
| 126 | 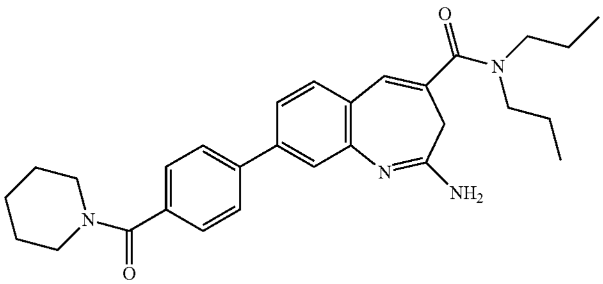 [SMILES: CCCN(CCC)C(=O)C1=Cc2ccc(-c3ccc(C(=O)N4CCCCC4)cc3)cc2N=C(N)C1] | ++ |
| 133 | 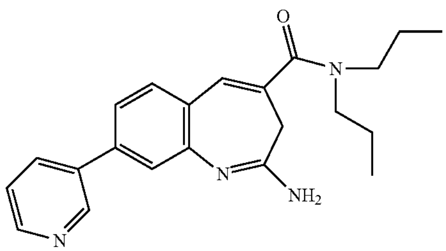 [SMILES: CCCN(CCC)C(=O)C1=Cc2ccc(-c3cccnc3)cc2N=C(N)C1] | ++ |
| 134 | 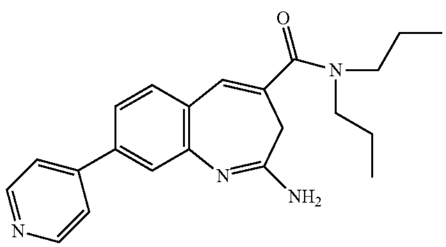 [SMILES: CCCN(CCC)C(=O)C1=Cc2ccc(-c3ccncc3)cc2N=C(N)C1] | ++ |
| 135 | 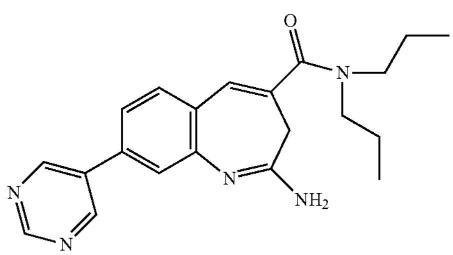 [SMILES: CCCN(CCC)C(=O)C1=Cc2ccc(-c3cncnc3)cc2N=C(N)C1] | +++ |
| 136 | 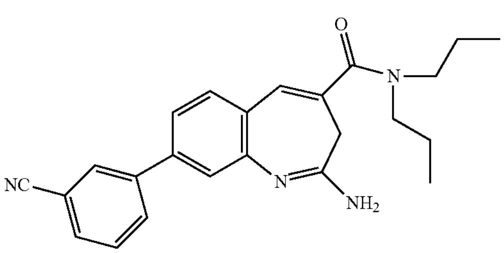 [SMILES: CCCN(CCC)C(=O)C1=Cc2ccc(-c3cccc(C#N)c3)cc2N=C(N)C1] | ++ |
| 137 | 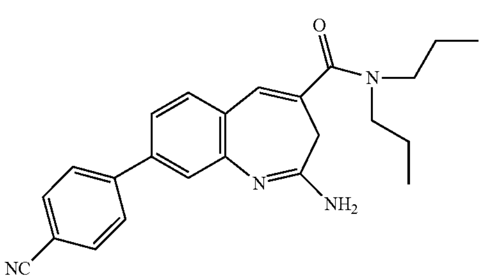 [SMILES: CCCN(CCC)C(=O)C1=Cc2ccc(-c3ccc(C#N)cc3)cc2N=C(N)C1] | + |

TABLE 3-continued

| Cmpd | Structure | TLR7 MC$_{50}$ |
|---|---|---|
| 138 | 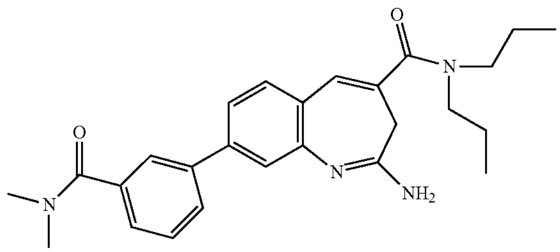 [SMILES: CCCN(CCC)C(=O)C1=Cc2ccc(-c3cccc(C(=O)N(C)C)c3)cc2N=C(N)C1] | ++ |
| 139 | 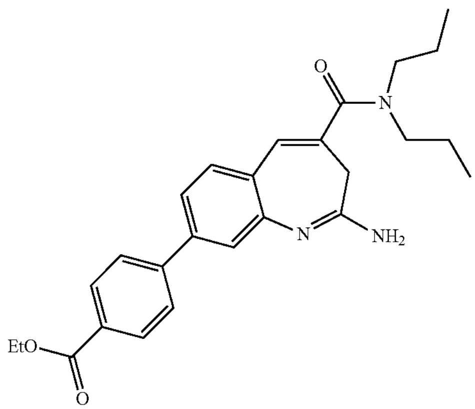 [SMILES: CCCN(CCC)C(=O)C1=Cc2ccc(-c3ccc(C(=O)OCC)cc3)cc2N=C(N)C1] | ++ |
| 190 | 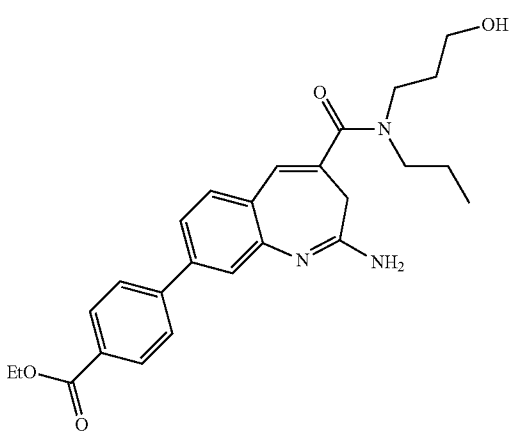 [SMILES: CCCN(CCCO)C(=O)C1=Cc2ccc(-c3ccc(C(=O)OCC)cc3)cc2N=C(N)C1] | + |
| 194 | 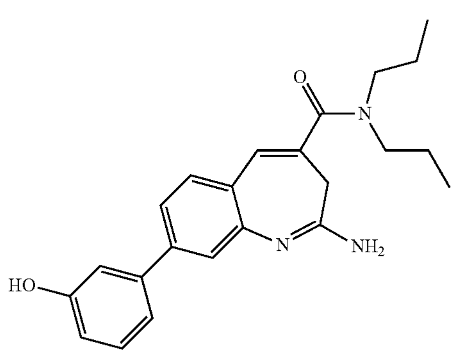 [SMILES: CCCN(CCC)C(=O)C1=Cc2ccc(-c3cccc(O)c3)cc2N=C(N)C1] | ++ |

TABLE 3-continued

| Cmpd | Structure | TLR7 MC$_{50}$ |
|---|---|---|
| 195 | 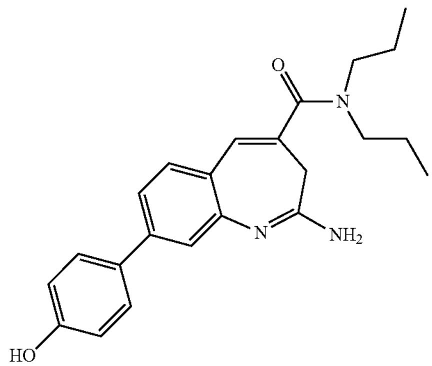 [SMILES: CCCN(CCC)C(=O)C1=Cc2ccc(-c3ccc(O)cc3)cc2N=C(N)C1] | +++ |
| 203 | 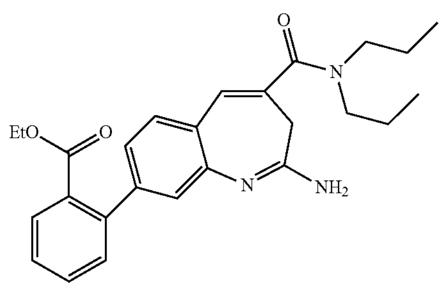 [SMILES: CCCN(CCC)C(=O)C1=Cc2ccc(-c3ccccc3C(=O)OCC)cc2N=C(N)C1] | ++ |
| 204 | 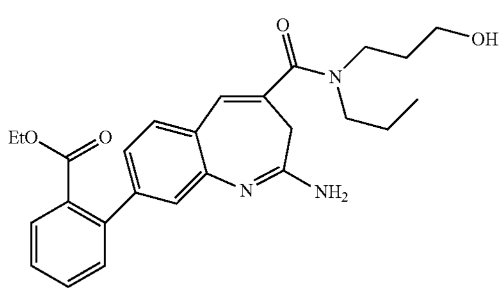 [SMILES: CCCN(CCCO)C(=O)C1=Cc2ccc(-c3ccccc3C(=O)OCC)cc2N=C(N)C1] | ++ |
| 206 | 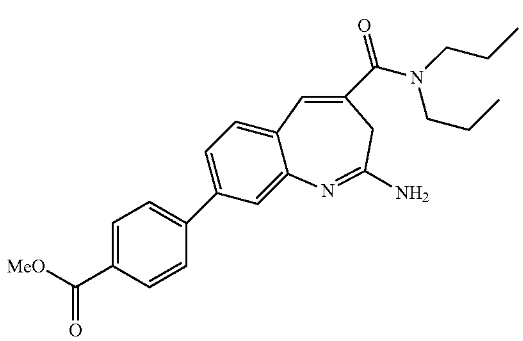 [SMILES: CCCN(CCC)C(=O)C1=Cc2ccc(-c3ccc(C(=O)OC)cc3)cc2N=C(N)C1] | ++ |

TABLE 3-continued
| Cmpd | Structure | TLR7 MC$_{50}$ |
|---|---|---|
| 207 | 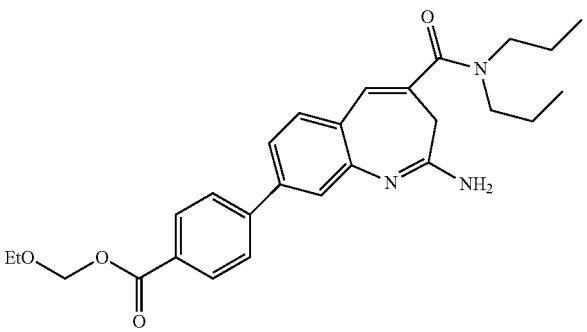 [SMILES: CCCN(CCC)C(=O)C1=Cc2ccc(-c3ccc(C(=O)OCOCC)cc3)cc2N=C(N)C1] | ++ |
| 210 | 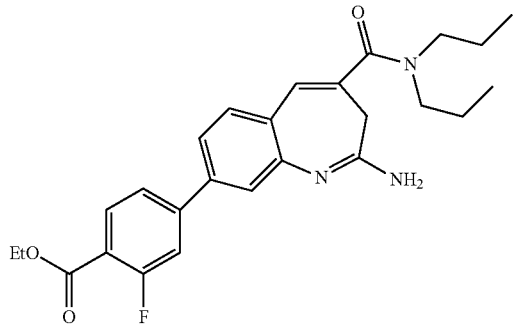 [SMILES: CCCN(CCC)C(=O)C1=Cc2ccc(-c3ccc(C(=O)OCC)c(F)c3)cc2N=C(N)C1] | ++ |
| 211 | 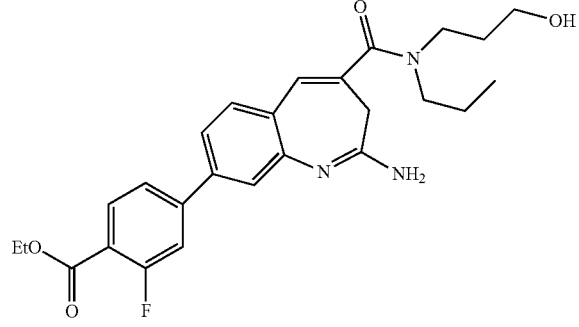 [SMILES: CCCN(CCCO)C(=O)C1=Cc2ccc(-c3ccc(C(=O)OCC)c(F)c3)cc2N=C(N)C1] | ++ |
| 212 | 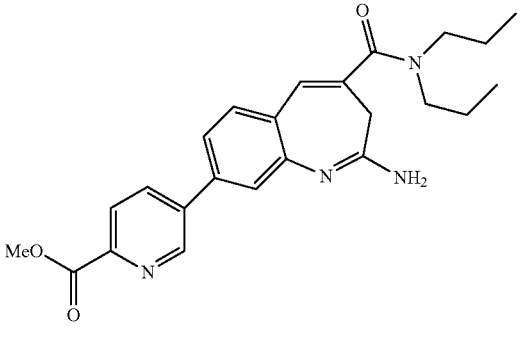 | ++ |

TABLE 3-continued

| Cmpd | Structure | TLR7 MC$_{50}$ |
|---|---|---|
| 220 | 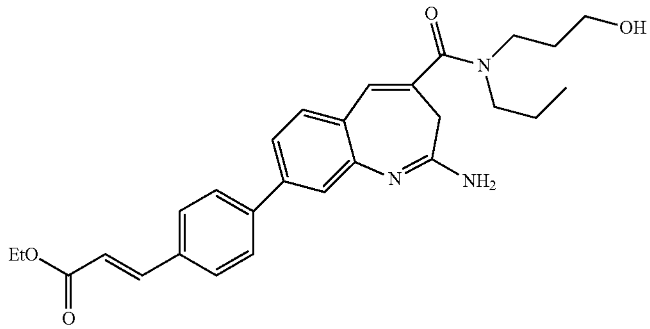 [SMILES: CCCN(CCCO)C(=O)C1=Cc2ccc(-c3ccc(/C=C/C(=O)OCC)cc3)cc2N=C(N)C1] | + |

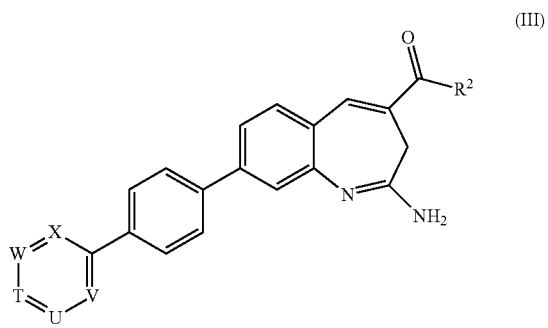

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof Unless otherwise noted, all references listed herein are specifically incorporated by reference.

What is claimed is:
1. A compound having the formula I:

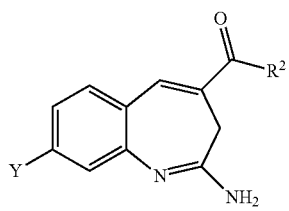

or a tautomer, enantiomer or salt thereof, wherein:
Y is heteroaryl;
$R^2$ is selected from $OR^{14}$ and $NR^6R^7$;
$R^6$ and $R^7$ are each independently selected from H, alkyl, cycloalkyl, heterocycle or benzyl, wherein said alkyl, cycloalkyl, or benzyl is optionally substituted with one or more groups independently selected from —F, —OR$^8$, —NR$^{12}$SO$_2$R$^{13}$, —C(=O)NR$^{12}$R$^{13}$ or R$^6$ and R$^7$ together with the nitrogen atom to which they are attached form a heterocyclic ring, further wherein said heterocyclic ring is optionally substituted with one or more —OH;
$R^8$ is selected from hydrogen and alkyl, and
$R^{12}$, $R^{13}$ and $R^{14}$ are each independently selected from H and alkyl, wherein said alkyl is optionally substituted with —OH.

2. A compound having the formula III:

(III)

or a tautomer, enantiomer or salt thereof, wherein
T is CH, CZ, or N;
U is CH, CZ, or N;
V is CH, CZ, or N;
X is CH, CZ, or N;
W is CH, CZ, or N;
$R^2$ is selected from $OR^{14}$ and $NR^6R^7$;
$R^6$ and $R^7$ are each independently selected from H, alkyl, cycloalkyl, heterocycle or benzyl, wherein said alkyl, cycloalkyl, or benzyl is optionally substituted with one or more groups independently selected from —F, —OR$^8$, —NR$^{12}$SO$_2$R$^{13}$, —C(=O)NR$^{12}$R$^{13}$ or R$^6$ and R$^7$ together with the nitrogen atom to which they are attached form a heterocyclic ring, further wherein said heterocyclic ring is optionally substituted with one or more —OH;
$R^8$ is selected from hydrogen and alkyl,
$R^{12}$, $R^{13}$ and $R^{14}$ are each independently selected from H and alkyl, wherein said alkyl is optionally substituted with —OH;
Z is selected from halogen, —CN, —CONR$^{16}$R$^{17}$, —COOR$^{18}$, —CH=CHCOOR$^{18}$, and —OR$^{19}$; and
$R^{16}$, $R^{17}$, $R^{18}$, and a $R^{19}$ are each independently selected from H, alkyl, and —CH$_2$O(alkyl).

3. The compound according to claim 1, having the formula IV:

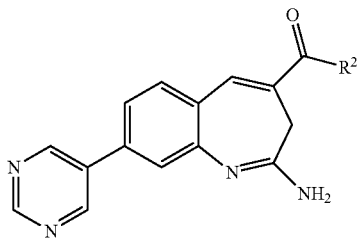

(IV)

or a tautomer, enantiomer or salt thereof.

4. A compound selected from the Group consisting of:

132
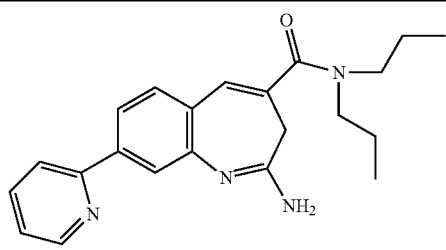

133
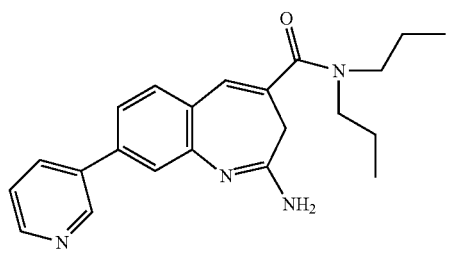 [SMILES: CCCN(CCC)C(=O)C1=Cc2ccc(-c3cccnc3)cc2N=C(N)C1]

134
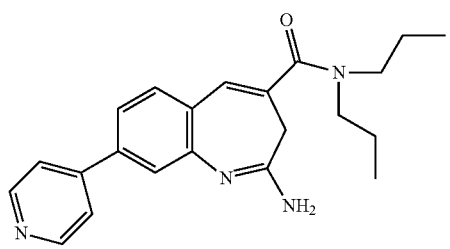 [SMILES: CCCN(CCC)C(=O)C1=Cc2ccc(-c3ccncc3)cc2N=C(N)C1]

135
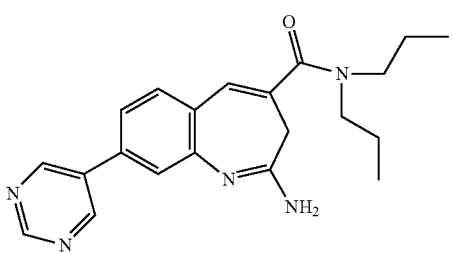 [SMILES: CCCN(CCC)C(=O)C1=Cc2ccc(-c3cncnc3)cc2N=C(N)C1]

141
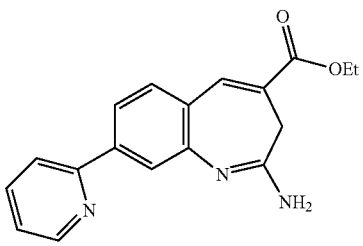 [SMILES: CCOC(=O)C1=Cc2ccc(-c3ccccn3)cc2N=C(N)C1]

142
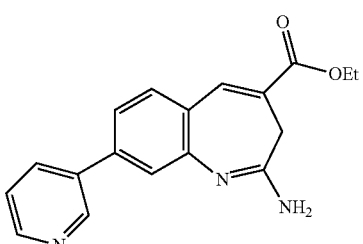

143
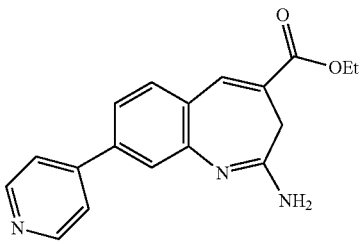 [SMILES: CCOC(=O)C1=Cc2ccc(-c3ccncc3)cc2N=C(N)C1]

144
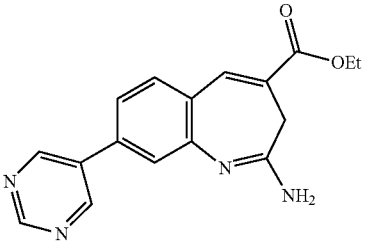 [SMILES: CCOC(=O)C1=Cc2ccc(-c3cncnc3)cc2N=C(N)C1]

and tautomers, enantiomers and salts thereof.

5. The compound according to claim 1, wherein the salt is a pharmaceutically acceptable salt.

6. A kit comprising:
   a) a container comprising a pharmaceutical composition comprising a compound of claim 1 or a tautomer, enantiomer or salt thereof; and
   b) optionally instructions for use.

7. A pharmaceutical composition, which comprises a compound of claim 1 or a tautomer, enantiomer or salt thereof together with a pharmaceutically acceptable diluent or carrier.

8. A method of treating cancer, comprising administering to a patient in need thereof an effective amount of a compound of claim 1 or a tautomer, enantiomer or salt thereof such that said cancer is treated, wherein said cancer is selected from biliary tract cancer, brain cancer, breast cancer, cervical cancer, choriocarcinoma, colon cancer, endometrial cancer, esophageal cancer, gastric cancer, intraepithelial neoplasms, leukemia, lymphoma, liver cancer, lung cancer, melanoma, neuroblastomas, oral cancer, ovarian cancer, pancreatic cancer, prostate cancer, rectal cancer, renal cancer, sarcomas, skin cancer, testicular cancer, thyroid cancer, other carcinomas and sarcomas.

9. A method of treating allergy, comprising administering to a patient in need thereof an effective amount of a compound of claim 1 or a tautomer, enantiomer or salt thereof such that said allergy is treated.

10. The method of claim 9, wherein said allergy is acquired hypersensitivity to an allergen, eczema, allergic rhinitis or coryza, hay fever, asthma, urticaria (hives), food allergies, or other atopic conditions.

11. The compound of claim 4, selected from

141
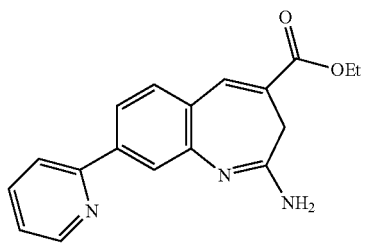 [SMILES: CCOC(=O)C1=Cc2ccc(-c3ccccn3)cc2N=C(N)C1]

142
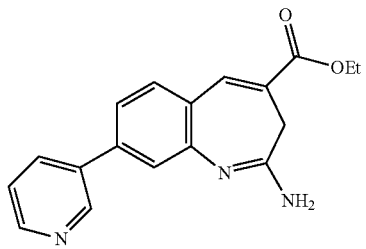 [SMILES: CCOC(=O)C1=Cc2ccc(-c3cccnc3)cc2N=C(N)C1]

143
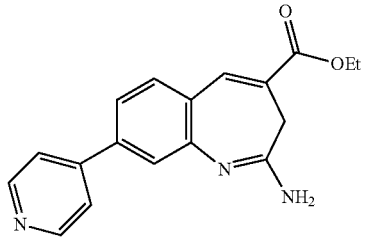 [SMILES: CCOC(=O)C1=Cc2ccc(-c3ccncc3)cc2N=C(N)C1]

144
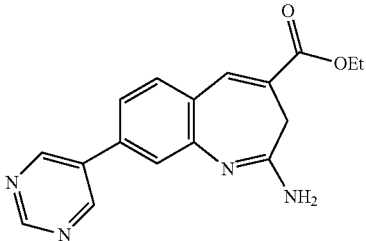 [SMILES: CCOC(=O)C1=Cc2ccc(-c3cncnc3)cc2N=C(N)C1]

133
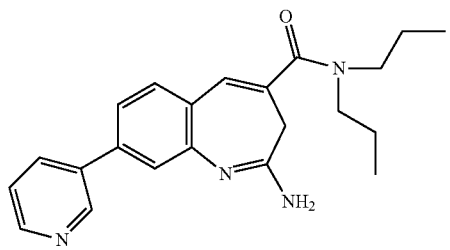 [SMILES: CCCN(CCC)C(=O)C1=Cc2ccc(-c3cccnc3)cc2N=C(N)C1]

-continued

134
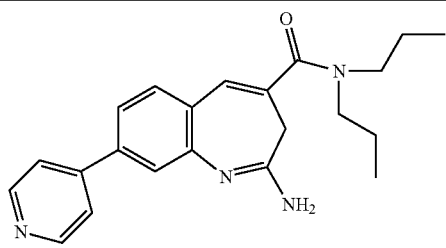

135
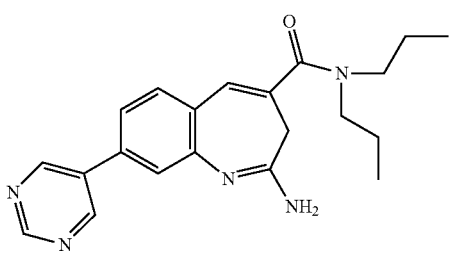 [SMILES: CCCN(CCC)C(=O)C1=Cc2ccc(-c3cncnc3)cc2N=C(N)C1]

and tautomers, enantiomers and salts thereof.

12. The compound of claim 4, selected from

141
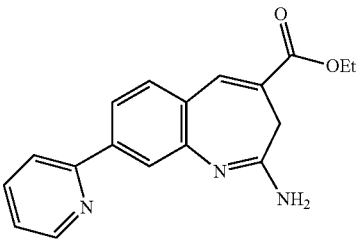 [SMILES: CCOC(=O)C1=Cc2ccc(-c3ccccn3)cc2N=C(N)C1]

143
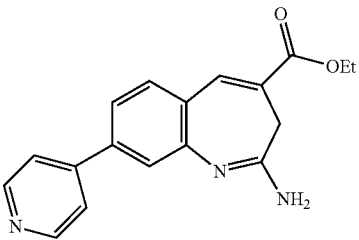 [SMILES: CCOC(=O)C1=Cc2ccc(-c3ccncc3)cc2N=C(N)C1]

144
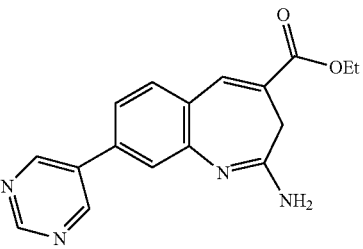 [SMILES: CCOC(=O)C1=Cc2ccc(-c3cncnc3)cc2N=C(N)C1]

133
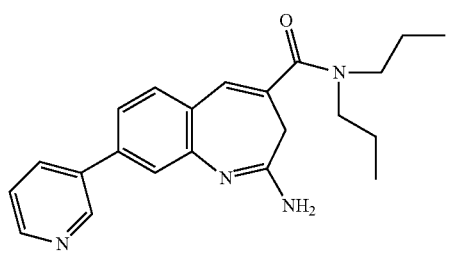 [SMILES: CCCN(CCC)C(=O)C1=Cc2ccc(-c3cccnc3)cc2N=C(N)C1]

135

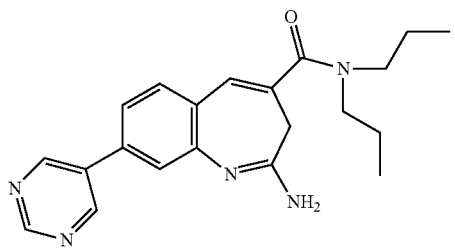 [SMILES: CCCN(CCC)C(=O)C1=Cc2ccc(-c3cncnc3)cc2N=C(N)C1]

and tautomers, enantiomers and salts thereof.

13. A pharmaceutical composition, which comprises a compound of claim 4 or a tautomer, enantiomer or salt thereof together with a pharmaceutically acceptable diluent or carrier.

14. A method of treating cancer, comprising administering to a patient in need thereof an effective amount of a compound of claim 4 or a tautomer, enantiomer or salt thereof such that said cancer is treated, wherein said cancer is selected from biliary tract cancer, brain cancer, breast cancer, cervical cancer, choriocarcinoma, colon cancer, endometrial cancer, esophageal cancer, gastric cancer, intraepithelial neoplasms, leukemia, lymphoma, liver cancer, lung cancer, melanoma, neuroblastomas, oral cancer, ovarian cancer, pancreatic cancer, prostate cancer, rectal cancer, renal cancer, sarcomas, skin cancer, testicular cancer, thyroid cancer, other carcinomas and sarcomas.

15. A method of treating allergy, comprising administering to a patient in need thereof an effective amount of a compound of claim 4 or a tautomer, enantiomer or salt thereof such that said allergy is treated.

16. The method of claim 15, wherein said allergy is acquired hypersensitivity to an allergen, eczema, allergic rhinitis or coryza, hay fever, asthma, urticaria (hives), food allergies, or other atopic conditions.

17. A pharmaceutical composition, which comprises a compound of claim 3 or a tautomer, enantiomer or salt thereof together with a pharmaceutically acceptable diluent or carrier.

18. A method of treating cancer, comprising administering to a patient in need thereof an effective amount of a compound of claim 3 or a tautomer, enantiomer or salt thereof such that said cancer is treated, wherein said cancer is selected from biliary tract cancer, brain cancer, breast cancer, cervical cancer, choriocarcinoma, colon cancer, endometrial cancer, esophageal cancer, gastric cancer, intraepithelial neoplasms, leukemia, lymphoma, liver cancer, lung cancer, melanoma, neuroblastomas, oral cancer, ovarian cancer, pancreatic cancer, prostate cancer, rectal cancer, renal cancer, sarcomas, skin cancer, testicular cancer, thyroid cancer, other carcinomas and sarcomas.

19. A method of treating allergy, comprising administering to a patient in need thereof an effective amount of a compound of claim 3 or a tautomer, enantiomer or salt thereof such that said allergy is treated.

20. The method of claim 19, wherein said allergy is acquired hypersensitivity to an allergen, eczema, allergic rhinitis or coryza, hay fever, asthma, urticaria (hives), food allergies, or other atopic conditions.

* * * * *